United States Patent [19]

Patel et al.

[11] Patent Number: 5,510,318

[45] Date of Patent: Apr. 23, 1996

[54] HERBICIDAL OXAZINE ETHERS

[75] Inventors: Kanu M. Patel, Wilmington; Thomas M. Stevenson, Newark, both of Del.

[73] Assignee: E. I. Du Pont de Nemours and Company, Wilmington, Del.

[21] Appl. No.: 64,004

[22] Filed: May 25, 1993

Related U.S. Application Data

[63] Continuation-in-part of Ser. No. 618,146, Nov. 26, 1990, abandoned.

[51] Int. Cl.[6] ........................ C07D 265/02; A01N 43/72
[52] U.S. Cl. ...................... 504/223; 504/225; 544/63
[58] Field of Search ....................... 544/63; 504/233,225

[56] References Cited

U.S. PATENT DOCUMENTS

| | | | |
|---|---|---|---|
| 4,552,585 | 11/1985 | Chang | 71/88 |
| 4,668,276 | 5/1987 | Handte et al. | 71/88 |
| 4,892,870 | 1/1990 | Lee | 514/211 |

FOREIGN PATENT DOCUMENTS

| | | | |
|---|---|---|---|
| 334120 | 9/1989 | European Pat. Off. | C07D 261/04 |
| 343859 | 11/1989 | European Pat. Off. | C07D 493/08 |

OTHER PUBLICATIONS

Chemical Abstracts vol. 117:131232 (1992).

*Primary Examiner*—Nicholas Rizzo

[57] ABSTRACT

The present invention relates to novel oxazine ether derivatives of Formula I, to compositions containing them, to methods of using the compounds or compositions to control the growth of undesired vegetation and novel intermediates for their preparation.

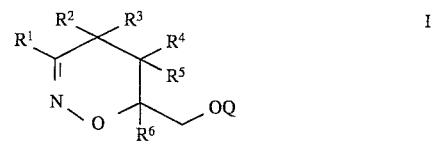

wherein:

$R^1$, $R^2$, $R^3$, $R^4$, $R^5$, $R^6$, and Q are defined in the text.

20 Claims, No Drawings

HERBICIDAL OXAZINE ETHERS

CROSS-REFERENCE TO RELATED APPLICATION

This application is the U.S. national filing of International Application No. PCT/US91/08234, filed Nov. 13, 1991, a continuation-in-part of U.S. Ser. No. 07/618,146, filed Nov. 26, 1990, now abandoned.

BACKGROUND OF THE INVENTION

The present invention relates to novel oxazine ether derivative compounds, to compositions containing them, to methods of using the compounds or compositions to control the growth of undesired vegetation and novel intermediates for their preparation.

Rheinheimer et al., EP-A-334,120 discloses herbicidal isoxazolines of the formula:

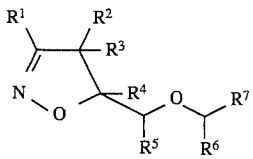

SUMMARY OF THE INVENTION

This invention comprises compounds of Formula I including stereoisomers, agriculturally suitable compositions containing them, their method-of-use as broad spectrum preemergent and postemergent herbicides:

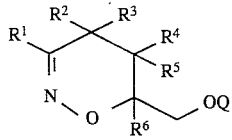

wherein:

$R^1$ is $C_1-C_6$ alkyl optionally substituted with a substituent selected from halogen, phenyl and $C_1-C_3$ alkoxy optionally substituted with 1–3 halogens; $C_2-C_6$ alkenyl optionally substituted with halogen or $C_1-C_3$ alkoxy; $C_2-C_4$ alkynyl; $C_3-C_6$ cycloalkyl; $C_5-C_6$ cycloalkenyl; CN; phenyl optionally substituted with one to two groups selected from halogen, $SCH_3$, CN, $C_1-C_2$ alkyl optionally substituted with 1–3 halogens; $C_1-C_2$ alkoxy optionally substituted with 1–3 halogens, a 5–7 membered heterocyclic ring containing one or more heteroatoms selected from the group 0–2 nitrogens, 0–2 oxygens and 0–2 sulfurs, each ring optionally substituted with one to two groups selected from halogen, $CH_3$ and $OCH_3$— a representative exemplification of such heterocycles includes but is not limited to pyridine, thiophene, furan, thiazole, oxazole, pyrrole, tetrahydrofuran, tetrahydropyran and pyrazole; and $CR^9R^{10}X$;

X is CN, $CO_2R^{13}$, $C(O)R^{14}$, CHO, $OR^{15}$ or $CR^{11}R^{12}Y$;

Y is $OR^{16}$;

$R^2$, $R^3$, $R^4$, $R^5$, $R^{13}$, $R^{14}$, $R^{15}$, $R^{16}$, $R^{20}$ and $R^{21}$ are independently H or $C_1-C_3$ alkyl;

$R^6$ is H, $C_1-C_3$ alkyl or $C_2-C_4$ alkenyl;

$R^1$ and $R^2$ may be taken together to form a 5–6 membered ring substituted with $R^{20}$ and $R^{21}$ and optionally fused to a benzene ring;

$R^9$ and $R^{11}$ are independently H or $CH_3$;

$R^{10}$ and $R^{12}$ are independently H, $CH_3$ or $OCH_3$;

Q is $CH_2W$ or

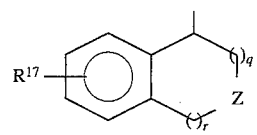

$R^{17}$ is H, halogen $C_1-C_3$ alkyl $OR^{18}$, $SR^{18}$ or CN;

$R^{18}$ is $C_1-C_3$ alkyl or $C_1-C_3$ haloalkyl;

Z is $CH_2$, $NR^{19}$, O, S or may be CH and taken to form a double bond with an adjacent carbon;

$R^{19}$ is H or $C_1-C_3$ alkyl;

q is 0–2;

r is 0–2;

W is phenyl optionally substituted with 1–3 substituents selected from halogen, $C_1-C_3$ alkyl, $C_1-C_3$ alkoxy, OH, CN, $C_1-C_3$ haloalkyl, $C_1-C_3$ haloalkoxy, $C_1-C_3$ alkylthio, $C_2-C_4$ alkenyl and $C_2-C_4$ alkynyl; or a 5-, 6-, 7-membered heterocyclic ring containing one or more heteroatoms selected from the group 0–2 nitrogens, 0–2 oxygens and 0–2 sulfurs, each ring optionally substituted with 1–2 substituents selected from halogen, $CH_3$ and $OCH_3$— a representative exemplification of such heterocycles includes but is not limited to pyrrole, furan, thiophene, tetrahydrofuran, tetrahydropyran, isoxazole, oxazole, pyrazole, imidazole, thiazole, pyridine and pyrazine;

provided that 1) the sum of q and r is 0–2; and 2) if the sum of q and r is 0 then Z is $CH_2$.

Preferred for either their biological activity and/or ease of synthesis are:

1) Compounds of Formula I, wherein:

W is phenyl optionally substituted by 1–2 substituents selected from halogen, $C_3$ and $OCH_3$; or tetrahydropyran, tetrahyrofuran, thiophene, isoxazole, pyridine or pyrazine, each ring optionally substituted with 1–2 substituents selected from F, Cl, Br, $CH_3$ and $OCH_3$;

Q is $CH_2W$ or

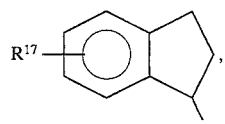 Q-1

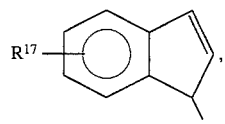 Q-2

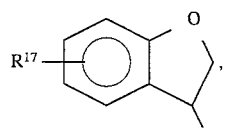 Q-3

3
-continued

Q-4: [structure with R19, N, R17]

Q-5: [structure with S, R17]

Q-6: [structure with R17]

Q-7: [structure with O, R17]

Q-8: [structure with O, R17]

Q-9: [structure with R19, N, R17]

Q-10: [structure with N-R19, R17]

Q-11: [structure with S, R17]

Q-12: [structure with S, R17]

Q-13: [structure with R17]

Q-14: [structure with R17] or

Q-15: [structure with R17]

2) Compounds of Preferred 1 wherein:

$R^1$ is $C_1$–$C_6$ alkyl; $C_3$–$C_6$ cycloalkyl; phenyl optionally substituted with one to two halogens; and $CR^9R^{10}X$; $R^2$, $R^3$, $R^4$ and $R^5$ are independently H; and $R^6$ is $C_1$–$C_3$ alkyl and $C_2$–$C_4$ alkenyl.

3) Compounds of Preferred 1 wherein:
W is phenyl optionally substituted with 1–2 halogens; and
Q is $CH_2W$ or Q-1, Q-3, Q-6, Q-7, or Q-15.

4) Compounds of Preferred 2 wherein
$R^1$ is $C_3$–$C_5$ alkyl, $C_3$–$C_6$ cycloalkyl or phenyl optionally substituted with one to two halogens.

Specifically preferred for their biological activity and/or ease of synthesis are the compounds of Preferred 4 which are:

3-(1,1-dimethylethyl)-6-[[(2-fluorophenyl)-methoxy]methyl]-5,6-dihydro-6-methyl-4H-1,2-oxazine;

6-[[(2,6-difluorophenyl)methoxy]methyl]-3-(1,1-dimethylethyl)-5,6-dihydro-6-methyl-4H-1,2-oxazine;

6-[[(2,6-difluorophenyl)methoxy]methyl]-3-(1,1-dimethylethyl)-6-ethyl-5,6-dihydro-4H-1,2-oxazine; and 6-[[(2,6-difluorophenyl)methoxy]methyl]-6-ethyl-5,6-dihydro-3-phenyl-4H-1,2-oxazine.

This invention also comprises intermediates used for the preparation of compounds of Formula I such as alcohols of Formula II.

[Structure II with $R^1$, $R^2$, $R^3$, $R^4$, $R^5$, $R^6$, N, O, OH]

wherein:

$R^1$ is $C_1$–$C_6$ alkyl optionally substituted with a substituent selected from halogen, phenyl and $C_1$–$C_3$ alkoxy optionally substituted with 1–3 halogens; $C_2$–$C_6$ alkenyl optionally substituted with halogen or $C_1$–$C_3$ alkoxy; $C_2$–$C_4$ alkynyl; $C_3$–$C_6$ cycloalkyl; $C_5$–$C_6$ cycloalkenyl; CN; phenyl optionally substituted with one to two groups selected from halogen, $SCH_3$, CN, $C_1$–$C_2$ alkyl optionally substituted with 1–3 halogens; a 5–7 membered heterocyclic ring containing one or more heteroatoms selected from the group 0–2 nitrogens, 0–2 oxygens and 0–2 sulfurs, each ring optionally substituted with one to two groups selected from halogen, $CH_3$ and $OCH_3$— a representative exemplification of such heterocycles includes but is not limited to pyridine, thiophene, furan, thiazole, oxazole, pyrrole, tetrahydrofuran, tetrahydropyran and pyrazole; and $CR^9R^{10}X$;

X is CN, $CO_2R^{13}$, $C(O)R^{14}$, CHO, $OR^{15}$ or $CR^{11}R^{12}Y$;

Y is $OR^{16}$;

$R^2$, $R^3$, $R^4$, $R^5$, $R^{13}$, $R^{14}$, $R^{15}$ and $R^{16}$ are independently H or $C_1$–$C_3$ alkyl;

$R^6$ is H, $C_1$–$C_3$ alkyl or $C_2$–$C_4$ alkenyl;

$R^1$ and $R^2$ may be taken together to form a 5–6 membered ring optionally fused to a benzene ring;

$R^9$ and $R^{11}$ are independently H or $CH_3$;

$R^{10}$ and $R^{12}$ are independently H, $CH_3$ or $OCH_3$.

Preferred for their ease of synthesis are:

1) Compounds of Formula II wherein:
$R^1$ is $C_1$–$C_6$ alkyl; $C_3$–$C_6$ cycloalkyl; phenyl optionally substituted with one to two halogens; and $CR^9R^{10}X$; $R^2$, $R^3$, $R^4$ and $R^5$ are independently H; and $R^6$ is $C_1$–$C_3$ alkyl and $C_2$–$C_4$ alkenyl.

2) Compounds of Preferred 1 wherein
$R^1$ is $C_3$–$C_5$ alkyl, $C_3$–$C_6$ cycloalkyl or phenyl optionally substituted with one to two halogens.

In the above definitions, the term "alkyl" used either alone or in compound words such as "haloalkyl" includes straight chain or branched alkyl. Alkoxy includes all isomers. Alkenyl includes straight chain or branched alkenes. The term "halogen", either alone or in compound words such as "haloalkyl" means fluorine, chlorine, bromine or iodine.

DETAILED DESCRIPTION OF THE INVENTION

The compounds of the present invention (Formula I) can be prepared by the reaction of alcohols of Formula II with activated halides or sulfonates of Formula III. This type of reaction is well known in the art and is carried out in the presence of a suitable base such as sodium hydride (NaH), potassium tert-butoxide (KOt-Bu), or other strong bases. This sequence can be carried out in a variety of solvents provided that they do not react with the base. Examples of such solvents include tetrahydrofuran, dimethylformamide, dimethylacetamide, dioxane, or mixtures thereof. Alternatively the coupling can be carried out under phase-transfer conditions using an alkali hydroxide as base and a tetraalkylammonium salt as catalyst. (See Weber and Gokel, "Phase Transfer Catalysis in Organic Synthesis", Springer Verlag, New York, 1977). The halides and sulfonates of Formula III are generally commercially available or can be readily synthesized by those skilled in the art. In some instances where less active alkylating agents such as chlorides are being used the addition of a soluble iodide salt, such as sodium iodide, in catalytic or stoichiometric amounts can speed the reaction.

Scheme 1

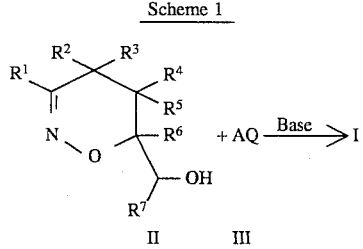

wherein:
A is halogen, or an alkyl or aryl sulfonate.

The compounds of Formula I in which the Q values are Q1–Q15 can be made by applying the methods disclosed in EP-A-343,859 to the alcohols of Formula II. For example, when the coupling procedure described above proves problematic, an alternative procedure using a Lewis acidic metal oxide, wherein the metal can remove the halide ion by forming an insoluble precipitate, may be carried out.

Compounds of Formula II can be formed by the cycloaddition of nitrosoolefins with substituted olefinic alcohols of Formula IV. The chemistry of nitrosoolefins and their cycloadditions can be found in Boger and Weinreb, "HeteroDiels-Alder Reactions in Organic Synthesis" Academic Press, New York, 1989. The nitrosoolefins are generated in the presence of the olefinic alcohols by the reaction of oximes of Formula V with base. The reactions may be carried out in a variety of solvents with dichloromethane being a preferred reaction medium. Inorganic bases which are not fully soluble in the reaction medium, such as sodium carbonate, are preferred. Bases which are soluble promote reaction of the oxime of Formula V at too fast a rate. Heterogeneous conditions give a lower concentration of the nitrosoolefin intermediate and lead to better yields and purity of alcohols of Formula II. The olefinic alcohols of Formula IV and base are preferably used in excess in comparison to the oxime of Formula V. The alcohols of Formula IV are generally commercially available or can be synthesized by means known to those skilled in the art.

Scheme 2a

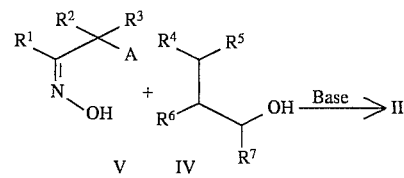

wherein:
A is halogen.

Compounds of Formula II can be made by reaction of metallated oximes of Formula (X) with epoxides of Formula (XI). The oximes are metallated by reaction with either an alkyl lithium or lithium amide base. The metallation reaction is best carried out at 0° C. due to the exothermic reaction of the deprotonation of the oxime proton. Suitable solvents for the reaction are diethyl ether, tetrahydrofuran, and other ethers. Representative bases are n-butyl lithium, methyl lithium, and lithium diisopropyl amide. The epoxides (XI) are commercially available or are known in the art.

Scheme 2b

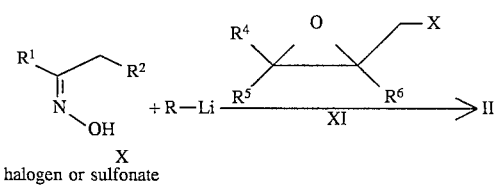

X = halogen or sulfonate

The halooximes of Formula V can be made from ketones of Formula VI by reaction with salts of hydroxylamine in mixtures of water and alcoholic solvents. Suitable conditions for the transformation can be found in Hassner and Alexanian, *J. Org. Chem.*, 1979, 44, 3861–3864. These conditions can include the use of a hydroxylamine salt, such as the hydrochloride or sulfate, in a medium in which the salt is at least partially soluble along with the haloketone VI at room temperature. In order to achieve maximum solubility of all components the solvent usually is a mixture of an alcohol, such as methanol or ethanol, and water. The ketones of Formula VI are commercially available or are generally known in the art. (Typical methods can be found in March, "Advanced Organic Chemistry", Wiley/Interscience, New York, 1985).

Scheme 3

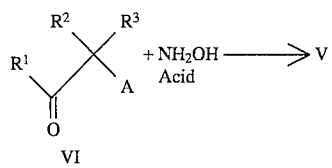

wherein:
A is halogen.

Halooximes of Formula V can also be made by the reaction of alkenes of Formula VII with nitrosoyl halides- (NOA). This reaction is well known in the art and is the subject of a review, see Kadyaukas and Zefirov, *Russ. Chem. Rev.*, 1968, 37, 543–550. The sequence works best when nitrosoyl chloride is used.

Scheme 4

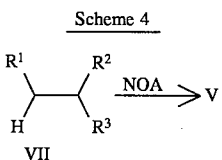

Alternatively, compounds of Formula I can also be synthesized directly from the reaction of nitrosoolefins generated from compounds of Formula V. By applying the conditions of Scheme 1 to the alcohols of Formula IV substituted olefinic ethers of Formula VIII are formed. Reaction of the ethers of Formula VIII with the oximes of Formula V in the presence of inorganic bases, such as sodium carbonate, in a solvent, such as dichloromethane, leads directly to compounds of Formula I.

Scheme 5

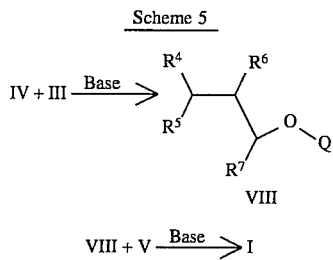

EXAMPLE 1

3-(1,1-Dimethylethyl)-5,6-dihydro-6-methyl-4H-1,2-oxazine-6-methanol

To a solution of 1-bromo-3,3-dimethyl-2-butanone oxime (4.5 g) (*J. Org. Chem.*, 1979, 44, 3861) in dichloromethane (150 mL) was added methallyl alcohol (22 mL) and sodium carbonate (16 g). The reaction mixture was stirred at room temperature for 40 h and then filtered through a pad of Celite. The solvent and excess alcohol were removed at reduced pressure. The residue was chromatographed on silica gel with 2:1 hexanes/ethyl acetate to give the title compound (3.2 g) as a low melting waxy solid. NMR (200 Mhz, CDCl$_3$) 3.5 (m, 2H, CH$_2$OH), 2.2–1.6 (m, 4H, ring CH$_2$'s), 1.2 (s, 12H, t-Bu and Me). IR (Nujol) 3240 cm$^{-1}$ (br, OH).

EXAMPLE 2

3-(1-Dimethylethyl)-6-[[(2-fluorophenyl)-methoxy]methyl]-5,6-dihydro-6-methyl- 4H-1,2-oxazine (Compound 4)

To a solution of the product from Example 1 (0.9 g) in tetrahydrofuran (7 mL) and dimethylacetamide (5 mL) was added sodium hydride (0.3 g) and the mixture was stirred for 20 minutes and then cooled in an ice bath. 2-Fluorobenzyl bromide was then added and the reaction was stirred at room temperature for 2 h. The reaction was quenched with saturated aqueous ammonium chloride solution and extracted with ether. The organic layer was dried with magnesium sulfate and evaporated. The residue was chromatographed on silica gel with 12:1 hexanes/ethyl acetate to give the title compound (1.19 g) as an oil. NMR (200 Mhz, CDCl$_3$) 7.5–7.0 (m, 4H, ArH), 4.64 (m, 2H, CH$_2$O), 3.4 (m, 2H, CH$_2$O), 2.2–1.5 (m, 4H, 2xCH$_2$), 1.24 (s, 3H, Me), 1.14 (s, 9H, t-Bu).

EXAMPLE 3

3-(1-indanol) (s)-(+)-2-methyl propene 4.8 g (60% in oil) of hexane washed sodium hydride was added to 50 mL of dimethylformamide, then a solution of 4.18 g of 1-indanol (s)-(+) in 15 mL of dimethylformamide was added dropwise over 20 minutes; an exothermic reaction to 40° C. occurred. The mixture was stirred at room temperature for 1 hour. Then 10.12 g of 3-chloro-2-methyl propene was added dropwise to the above mixture and the reaction mixture was stirred at room temperature for 18 hours. The mixture was added to excess water and extracted with 3×100 mL ethyl ether. The ethyl ether extract was washed with 1×50 mL water and 1×50 mL brine and dried over (MgSO$_4$). The ether was removed and the residual oil was flash chromatographed on silica gel with a mixture of 95:5 (v:v) hexane and diethyl ether to provide 4.65 g of the title compound as a light yellow oil. NMR (CDCl$_3$): 7.4–7.23 (m, Ar—H, 4H), 5.0 (m, 1H), 4.9 (m, CH$_2$O, 2H), 3.99 (m, 2H), 3.1–2.0 (m, 4H), 1.78 (s, CH$_3$, 3H). IR (neat): 3100, 1660, 1460 cm$^{-1}$.

EXAMPLE 4

6-[[(3,4-dihydro-2M-1-benzopyran-4-yl)oxy]methyl]-3-(1,1-dimethylethyl)-5,6-dihydro-6-methyl-4H-1,2 oxazine (Compound 52)

A mixture of 2 g of 3-(1-indanol) (s) (+)-2-methyl propene, 1.2 g bromo-methyl-t-butyl oxime and 1.5 g of sodium carbonate was stirred in 20 mL of methylene chloride at room temperature for five days. The mixture was filtered, washed with 50 mL methylene chloride and the filtrate was concentrated and flash chromatographed on silica gel with a mixture of 9:1 (v:v) hexane and diethyl ether to provide 0.89 g of Compound 52 as an oil. NMR (CDCl$_3$): 7.4–7.23 (m, Ar—M, 4H), 5.0 (m, CH, 1H), 3.46 (m, CH$_2$, 2H), 3.0 (m, 1), 2.8 (m, 1H), 2.3 (m, 1H), 2.0 (m, 4H), 1.63 (m, 1H), 1.2 (m, CH$_3$, 3H), 1.12 (m, tBu, 9H). IR (neat): 2990, 1730, 1615, 1480, 380 cm$^{-1}$.

EXAMPLE 5

3-[[(2,6-difluorophenylmethoxy)methoxy]methyl]-3,4,4a,5,6,7-hexahydro-3-methylcyclopent[c][1,2] oxazine (Compounds 29 and 30, isomers)

Cyclopentanone oxime (Aldrich, 2.2 g) was dissolved in tetrahydrofuran (30 mL) and cooled to 0° C. The mixture was treated with n-BuLi (29 mL, 1.6N) (temperature rises to 15°–20°C.). After 30 minutes, 2-chloromethyl-2-methyloxirane (2.4 mL Maybridge Chemicals) is added and the mixture stirred at room temperature for 1.5 hours. The reaction was quenched with 1N NaOH solution (50 mL). After stirring for 10 minutes, the mixture was extracted with Et$_2$O and then methylene chloride. The organic solutions were combined, dried with magnesium sulfate, and evaporated. The residue was chromatographed on silica gel in 1:1 hexanes/ethyl acetate to give an oil (0.55 g). This oil was dissolved in tetrahydrofuran ("THF") (7 mL) and dimethylacetamide (3 mL) and treated with sodium hydride (60% in oil, 0.2 g). The mixture was stirred at room temperature for 30 minutes and treated with 2,6-difluorobenzyl bromide (0.68 g). After stirring for 24 hours, the mixture was quenched with $H_2O$ (20 mL) and extracted with $Et_2O$ (2×20 mL). The coined ether layers were re-extracted with $H_2O$ (2×20 mL). The ether was dried over ($MgSO_4$) and evaporated. The residual oil was chromatographed in hexanes/ethyl acetate (7:1) to give first Compound 29 (0.28 g) as an oil. ($CDCl_3$): 7.2 (m, 1H), 6.9 (m, 2H), 4.6 (m, $CH_2O$), 2H), 3.3 (2xd, 2H, $CH_2O$), 2.5–1.2 (alkyls), 1.3 (m, s, 3H).

Then Compound 30 eluted (0.28 g) as an oil. NMR ($CDCl_3$): 7.2–6.9 (m, ArH, 3H), 4.7 ($CH_2O$), 2H), 3.5 ($CH_2O$, 2H), 2.4–1.2 (m, alkyl H), 1.18 (s, m, 3H).

By using the reactions and conditions disclosed above in Schemes 1–5 and Examples 1–2 or by obvious modifications thereof and other functional group transformations known to those skilled in the art, the compounds of Tables 1–7 may be prepared.

Tables 1–7 pertain to compounds of Formula I.

TABLE 1

$R^2 = R^3 = R^4 = R^5 = R^7 = H$ and $Q = CH_2W$

| $R^1$ | $R^6$ | W | $R^1$ | $R^6$ | W |
|---|---|---|---|---|---|
| Me | Me | Phenyl | Me | Et | Phenyl |
| Me | Me | 2-Cl-Phenyl | Me | Et | 2-Cl-Phenyl |
| Me | Me | 2-F-Phenyl | Me | Et | 2-F-Phenyl |
| Me | Me | 2-Me-Phenyl | Me | Et | 2-Me-Phenyl |
| Me | Me | 2,6-diCl-Phenyl | Me | Et | 2,6-diCl-Phenyl |
| Me | Me | 2,6-diF-Phenyl | Me | Et | 2,6-diF-Phenyl |
| Et | Me | Phenyl | Et | Et | Phenyl |
| Et | Me | 2-Cl-Phenyl | Et | Et | 2-Cl-Phenyl |
| Et | Me | 2-F-Phenyl | Et | Et | 2-F-Phenyl |
| Et | Me | 2-Me-Phenyl | Et | Et | 2-Me-Phenyl |
| Et | Me | 2,6-diCl-Phenyl | Et | Et | 2,6-diCl-Phenyl |
| Et | Me | 2,6-diF-Phenyl | Et | Et | 2,6-diF-Phenyl |
| n-Pr | Me | Phenyl | n-Pr | Et | Phenyl |
| n-Pr | Me | 2-Cl-Phenyl | n-Pr | Et | 2-Cl-Phenyl |
| n-Pr | Me | 2-F-Phenyl | n-Pr | Et | 2-F-Phenyl |
| n-Pr | Me | 2-Me-Phenyl | n-Pr | Et | 2-Me-Phenyl |
| n-Pr | Me | 2,6-diCl-Phenyl | n-Pr | Et | 2,6-diCl-Phenyl |
| n-Pr | Me | 2,6-diF-Phenyl | n-Pr | Et | 2,6-diF-Phenyl |
| n-Bu | Me | Phenyl | n-Bu | Et | Phenyl |
| n-Bu | Me | 2-Cl-Phenyl | n-Bu | Et | 2-Cl-Phenyl |
| n-Bu | Me | 2-F-Phenyl | n-Bu | Et | 2-F-Phenyl |
| n-Bu | Me | 2-Me-Phenyl | n-Bu | Et | 2-Me-Phenyl |
| n-Bu | Me | 2,6-diCl-Phenyl | n-Bu | Et | 2,6-diCl-Phenyl |
| n-Bu | Me | 2,6-diF-Phenyl | n-Bu | Et | 2,6-diF-Phenyl |
| i-Pr | Me | Phenyl | i-Pr | Et | Phenyl |
| i-Pr | Me | 2-Cl-Phenyl | i-Pr | Et | 2-Cl-Phenyl |
| i-Pr | Me | 2-F-Phenyl | i-Pr | Et | 2-F-Phenyl |
| i-Pr | Me | 2-Me-Phenyl | i-Pr | Et | 2-Me-Phenyl |
| i-Pr | Me | 2,6-diCl-Phenyl | i-Pr | Et | 2,6-diCl-Phenyl |
| i-Pr | Me | 2,6-diF-Phenyl | i-Pr | Et | 2,6-diF-Phenyl |
| i-Bu | Me | Phenyl | i-Bu | Et | Phenyl |
| i-Bu | Me | 2-Cl-Phenyl | i-Bu | Et | 2-Cl-Phenyl |
| i-Bu | Me | 2-F-Phenyl | i-Bu | Et | 2-F-Phenyl |
| i-Bu | Me | 2-Me-Phenyl | i-Bu | Et | 2-Me-Phenyl |
| i-Bu | Me | 2,6-diCl-Phenyl | i-Bu | Et | 2,6-diCl-Phenyl |
| i-Bu | Me | 2,6-diF-Phenyl | i-Bu | Et | 2,6-diF-Phenyl |
| s-Bu | Me | Phenyl | s-Bu | Et | Phenyl |
| s-Bu | Me | 2-Cl-Phenyl | s-Bu | Et | 2-Cl-Phenyl |
| s-Bu | Me | 2-F-Phenyl | s-Bu | Et | 2-F-Phenyl |
| s-Bu | Me | 2-Me-Phenyl | s-Bu | Et | 2-Me-Phenyl |
| s-Bu | Me | 2,6-diCl-Phenyl | s-Bu | Et | 2,6-diCl-Phenyl |
| s-Bu | Me | 2,6-diF-Phenyl | s-Bu | Et | 2,6-diF-Phenyl |
| t-Bu | Me | Phenyl | t-Bu | Et | Phenyl |
| t-Bu | Me | 2-Cl-Phenyl | t-Bu | Et | 2-Cl-Phenyl |
| t-Bu | Me | 2-F-Phenyl | t-Bu | Et | 2-F-Phenyl |
| t-Bu | Me | 2-Me-Phenyl | t-Bu | Et | 2-Me-Phenyl |
| t-Bu | Me | 2,6-diCl-Phenyl | t-Bu | Et | 2,6-diCl-Phenyl |
| t-Bu | Me | 2,6-diF-Phenyl | t-Bu | Et | 2,6-diF-Phenyl |
| i-Amyl | Me | Phenyl | i-Amyl | Et | Phenyl |
| i-Amyl | Me | 2-Cl-Phenyl | i-Amyl | Et | 2-Cl-Phenyl |
| i-Amyl | Me | 2-F-Phenyl | i-Amyl | Et | 2-F-Phenyl |
| i-Amyl | Me | 2-Me-Phenyl | i-Amyl | Et | 2-Me-Phenyl |
| i-Amyl | Me | 2,6-diCl-Phenyl | i-Amyl | Et | 2,6-diCl-Phenyl |
| i-Amyl | Me | 2,6-diF-Phenyl | i-Amyl | Et | 2,6-diF-Phenyl |
| t-Amyl | Me | Phenyl | t-Amyl | Et | Phenyl |
| t-Amyl | Me | 2-Cl-Phenyl | t-Amyl | Et | 2-Cl-Phenyl |
| t-Amyl | Me | 2-F-Phenyl | t-Amyl | Et | 2-F-Phenyl |
| t-Amyl | Me | 2-Me-Phenyl | t-Amyl | Et | 2-Me-Phenyl |
| t-Amyl | Me | 2,6-diCl-Phenyl | t-Amyl | Et | 2,6-diCl-Phenyl |
| t-Amyl | Me | 2,6-diF-Phenyl | t-Amyl | Et | 2,6-diF-Phenyl |
| 2-propenyl | Me | Phenyl | 2-propenyl | Et | Phenyl |

TABLE 1-continued $R^2 = R^3 = R^4 = R^5 = R^7 = H$ and $Q = CH_2W$

| $R^1$ | $R^6$ | W | $R^1$ | $R^6$ | W |
|---|---|---|---|---|---|
| 2-propenyl | Me | 2-Cl-Phenyl | 2-propenyl | Et | 2-Cl-Phenyl |
| 2-propenyl | Me | 2-F-Phenyl | 2-propenyl | Et | 2-F-Phenyl |
| 2-propenyl | Me | 2-Me-Phenyl | 2-propenyl | Et | 2-Me-Phenyl |
| 2-propenyl | Me | 2,6-diCl-Phenyl | 2-propenyl | Et | 2,6-diCl-Phenyl |
| 2-propenyl | Me | 2,6-diF-Phenyl | 2-propenyl | Et | 2,6-diF-Phenyl |
| Vinyl | Me | Phenyl | Vinyl | Et | Phenyl |
| Vinyl | Me | 2-Cl-Phenyl | Vinyl | Et | 2-Cl-Phenyl |
| Vinyl | Me | 2-F-Phenyl | Vinyl | Et | 2-F-Phenyl |
| Vinyl | Me | 2-Me-Phenyl | Vinyl | Et | 2-Me-Phenyl |
| Vinyl | Me | 2,6-diCl-Phenyl | Vinyl | Et | 2,6-diCl-Phenyl |
| Vinyl | Me | 2,6-diF-Phenyl | Vinyl | Et | 2,6-diF-Phenyl |
| Ethynyl | Me | Phenyl | Ethynyl | Et | Phenyl |
| Ethynyl | Me | 2-Cl-Phenyl | Ethynyl | Et | 2-Cl-Phenyl |
| Ethynyl | Me | 2-F-Phenyl | Ethynyl | Et | 2-F-Phenyl |
| Ethynyl | Me | 2-Me-Phenyl | Ethynyl | Et | 2-Me-Phenyl |
| Ethynyl | Me | 2,6-diCl-Phenyl | Ethynyl | Et | 2,6-diCl-Phenyl |
| Ethynyl | Me | 2,6-diF-Phenyl | Ethynyl | Et | 2,6-diF-Phenyl |
| CN | Me | Phenyl | CN | Et | Phenyl |
| CN | Me | 2-Cl-Phenyl | CN | Et | 2-Cl-Phenyl |
| CN | Me | 2-F-Phenyl | CN | Et | 2-F-Phenyl |
| CN | Me | 2-Me-Phenyl | CN | Et | 2-Me-Phenyl |
| CN | Me | 2,6-diCl-Phenyl | CN | Et | 2,6-diCl-Phenyl |
| CN | Me | 2,6-diF-Phenyl | CN | Et | 2,6-diF-Phenyl |
| Phenyl | Me | Phenyl | Phenyl | Et | Phenyl |
| Phenyl | Me | 2-Cl-Phenyl | Phenyl | Et | 2-Cl-Phenyl |
| Phenyl | Me | 2-F-Phenyl | Phenyl | Et | 2-F-Phenyl |
| Phenyl | Me | 2-Me-Phenyl | Phenyl | Et | 2-Me-Phenyl |
| Phenyl | Me | 2,6-diCl-Phenyl | Phenyl | Et | 2,6-diCl-Phenyl |
| Phenyl | Me | 2,6-diF-Phenyl | Phenyl | Et | 2,6-diF-Phenyl |
| 2-Cl-Phenyl | Me | Phenyl | 2-Cl-Phenyl | Et | Phenyl |
| 2-Cl-Phenyl | Me | 2-Cl-Phenyl | 2-Cl-Phenyl | Et | 2-Cl-Phenyl |
| 2-Cl-Phenyl | Me | 2-F-Phenyl | 2-Cl-Phenyl | Et | 2-F-Phenyl |
| 2-Cl-Phenyl | Me | 2-Me-Phenyl | 2-Cl-Phenyl | Et | 2-Me-Phenyl |
| 2-Cl-Phenyl | Me | 2,6-diCl-Phenyl | 2-Cl-Phenyl | Et | 2,6-diCl-Phenyl |
| 2-Cl-Phenyl | Me | 2,6-diF-Phenyl | 2-Cl-Phenyl | Et | 2,6-diF-Phenyl |
| 3-Cl-Phenyl | Me | Phenyl | 3-Cl-Phenyl | Et | Phenyl |
| 3-Cl-Phenyl | Me | 2-Cl-Phenyl | 3-Cl-Phenyl | Et | 2-Cl-Phenyl |
| 3-Cl-Phenyl | Me | 2-F-Phenyl | 3-Cl-Phenyl | Et | 2-F-Phenyl |
| 3-Cl-Phenyl | Me | 2-Me-Phenyl | 3-Cl-Phenyl | Et | 2-Me-Phenyl |
| 3-Cl-Phenyl | Me | 2,6-diCl-Phenyl | 3-Cl-Phenyl | Et | 2,6-diCl-Phenyl |
| 3-Cl-Phenyl | Me | 2,6-diF-Phenyl | 3-Cl-Phenyl | Et | 2,6-diF-Phenyl |
| 4-Cl-Phenyl | Me | Phenyl | 4-Cl-Phenyl | Et | Phenyl |
| 4-Cl-Phenyl | Me | 2-Cl-Phenyl | 4-Cl-Phenyl | Et | 2-Cl-Phenyl |
| 4-Cl-Phenyl | Me | 2-F-Phenyl | 4-Cl-Phenyl | Et | 2-F-Phenyl |
| 4-Cl-Phenyl | Me | 2-Me-Phenyl | 4-Cl-Phenyl | Et | 2-Me-Phenyl |
| 4-Cl-Phenyl | Me | 2,6-diCl-Phenyl | 4-Cl-Phenyl | Et | 2,6-diCl-Phenyl |
| 4-Cl-Phenyl | Me | 2,6-diF-Phenyl | 4-Cl-Phenyl | Et | 2,6-diF-Phenyl |
| 2-Thienyl | Me | Phenyl | 2-Thienyl | Et | Phenyl |
| 2-Thienyl | Me | 2-Cl-Phenyl | 2-Thienyl | Et | 2-Cl-Phenyl |
| 2-Thienyl | Me | 2-F-Phenyl | 2-Thienyl | Et | 2-F-Phenyl |
| 2-Thienyl | Me | 2-Me-Phenyl | 2-Thienyl | Et | 2-Me-Phenyl |
| 2-Thienyl | Me | 2,6-diCl-Phenyl | 2-Thienyl | Et | 2,6-diCl-Phenyl |
| 2-Thienyl | Me | 2,6-diF-Phenyl | 2-Thienyl | Et | 2,6-diF-Phenyl |
| cyclopropyl | Me | Phenyl | cyclopropyl | Et | Phenyl |
| cyclopropyl | Me | 2-Cl-Phenyl | cyclopropyl | Et | 2-Cl-Phenyl |
| cyclopropyl | Me | 2-F-Phenyl | cyclopropyl | Et | 2-F-Phenyl |
| cyclopropyl | Me | 2-Me-Phenyl | cyclopropyl | Et | 2-Me-Phenyl |
| cyclopropyl | Me | 2,6-diCl-Phenyl | cyclopropyl | Et | 2,6-diCl-Phenyl |
| cyclopropyl | Me | 2,6-diF-Phenyl | cyclopropyl | Et | 2,6-diF-Phenyl |
| cyclopentyl | Me | Phenyl | cyclopentyl | Et | Phenyl |
| cyclopentyl | Me | 2-Cl-Phenyl | cyclopentyl | Et | 2-Cl-Phenyl |
| cyclopentyl | Me | 2-F-Phenyl | cyclopentyl | Et | 2-F-Phenyl |
| cyclopentyl | Me | 2-Me-Phenyl | cyclopentyl | Et | 2-Me-Phenyl |
| cyclopentyl | Me | 2,6-diCl-Phenyl | cyclopentyl | Et | 2,6-diCl-Phenyl |
| cyclopentyl | Me | 2,6-diF-Phenyl | cyclopentyl | Et | 2,6-diF-Phenyl |
| cyclohexyl | Me | Phenyl | cyclohexyl | Et | Phenyl |
| cyclohexyl | Me | 2-Cl-Phenyl | cyclohexyl | Et | 2-Cl-Phenyl |
| cyclohexyl | Me | 2-F-Phenyl | cyclohexyl | Et | 2-F-Phenyl |
| cyclohexyl | Me | 2-Me-Phenyl | cyclohexyl | Et | 2-Me-Phenyl |
| cyclohexyl | Me | 2,6-diCl-Phenyl | cyclohexyl | Et | 2,6-diCl-Phenyl |
| cyclohexyl | Me | 2,6-diF-Phenyl | cyclohexyl | Et | 2,6-diF-Phenyl |
| cyclopentenyl | Me | Phenyl | cyclopentenyl | Et | Phenyl |
| cyclopentenyl | Me | 2-Cl-Phenyl | cyclopentenyl | Et | 2-Cl-Phenyl |
| cyclopentenyl | Me | 2-F-Phenyl | cyclopentenyl | Et | 2-F-Phenyl |
| cyclopentenyl | Me | 2-Me-Phenyl | cyclopentenyl | Et | 2-Me-Phenyl |

TABLE 1-continued

| | | $R^2 = R^3 = R^4 = R^5 = R^7 = H$ and $Q = CH_2W$ | | | |
|---|---|---|---|---|---|
| $R^1$ | $R^6$ | W | $R^1$ | $R^6$ | W |
| cyclopentenyl | Me | 2,6-diCl-Phenyl | cyclopentenyl | Et | 2,6-diCl-Phenyl |
| cyclopentenyl | Me | 2,6-diF-Phenyl | cyclopentenyl | Et | 2,6-diF-Phenyl |
| Et | Me | 2-CN-Phenyl | i-Pr | Me | 2-CN-Phenyl |
| Et | Me | 2-Br-Phenyl | i-Pr | Me | 2-Br-Phenyl |
| Et | Me | 2-I-Phenyl | i-Pr | Me | 2-I-Phenyl |
| Et | Me | 2-CF$_3$-Phenyl | i-Pr | Me | 2-CF$_3$-Phenyl |
| Et | Me | 2-OMe-Phenyl | i-Pr | Me | 2-OMe-Phenyl |
| Et | Me | 2-OH-Phenyl | i-Pr | Me | 2-OH-Phenyl |
| Et | Me | 2-OCHF$_2$-Phenyl | i-Pr | Me | 2-OCHF$_2$-Phenyl |
| Et | Me | 2-Ethynyl-Phenyl | i-Pr | Me | 2-Ethynyl-Phenyl |
| Et | Me | 2-Ethenyl-Phenyl | i-Pr | Me | 2-Ethenyl-Phenyl |
| Et | Me | 2-SMe-Phenyl | i-Pr | Me | 2-SMe-Phenyl |
| Et | Me | 2-Pyridyl | i-Pr | Me | 2-Pyridyl |
| Et | Me | 2-Thienyl | i-Pr | Me | 2-Thienyl |
| Et | Me | 4-Thiazolyl | i-Pr | Me | 4-Thiazolyl |
| Et | Me | 2-Pyrazinyl | i-Pr | Me | 2-Pyrazinyl |
| Et | Me | 5-Isoxazolyl | i-Pr | Me | 5-Isoxazolyl |
| Et | Me | 2-(3-Chlorothienyl) | i-Pr | Me | 2-(3-Chlorothienyl) |
| Et | Me | 1-Cyclohexenyl | i-Pr | Me | 1-Cyclohexenyl |
| Et | Me | 1-Cyclopentenyl | i-Pr | Me | 1-Cyclopentenyl |
| Et | Me | 2-Tetrahydropyranyl | i-Pr | Me | 2-Tetrahydropyranyl |
| Et | Me | 2-Tetrahydrofuryl | i-Pr | Me | 2-Tetrahydrofuryl |
| Et | Me | 3-F-Phenyl | i-Pr | Me | 3-F-Phenyl |
| Et | Me | 4-F-Phenyl | i-Pr | Me | 4-F-Phenyl |
| Et | Me | 2,4-diF-Phenyl | i-Pr | Me | 2,4-diF-Phenyl |
| Et | Me | 2,5-diF-Phenyl | i-Pr | Me | 2,5-diF-Phenyl |
| Et | Me | 2-Cl, 4-F-Phenyl | i-Pr | Me | 2-Cl, 4-F-Phenyl |
| Et | Me | 2,4,6-triF-Phenyl | i-Pr | Me | 2,4,6-triF-Phenyl |
| Phenyl | Me | 2-CN-Phenyl | t-Bu | Me | 2-CN-Phenyl |
| Phenyl | Me | 2-Br-Phenyl | t-Bu | Me | 2-Br-Phenyl |
| Phenyl | Me | 2-I-Phenyl | t-Bu | Me | 2-I-Phenyl |
| Phenyl | Me | 2-CF$_3$-Phenyl | t-Bu | Me | 2-CF$_3$-Phenyl |
| Phenyl | Me | 2-OMe-Phenyl | t-Bu | Me | 2-OMe-Phenyl |
| Phenyl | Me | 2-OH-Phenyl | t-Bu | Me | 2-OH-Phenyl |
| Phenyl | Me | 2-OCHF$_2$-Phenyl | t-Bu | Me | 2-OCHF$_2$-Phenyl |
| Phenyl | Me | 2-Ethynyl-Phenyl | t-Bu | Me | 2-Ethynyl-Phenyl |
| Phenyl | Me | 2-Ethenyl-Phenyl | t-Bu | Me | 2-Ethenyl-Phenyl |
| Phenyl | Me | 2-SMe-Phenyl | t-Bu | Me | 2-SMe-Phenyl |
| Phenyl | Me | 2-Pyridyl | t-Bu | Me | 2-Pyridyl |
| Phenyl | Me | 2-Thienyl | t-Bu | Me | 2-Thienyl |
| Phenyl | Me | 4-Thiazolyl | t-Bu | Me | 4-Thiazolyl |
| Phenyl | Me | 2-Pyrazinyl | t-Bu | Me | 2-Pyrazinyl |
| Phenyl | Me | 5-Isoxazolyl | t-Bu | Me | 5-Isoxazolyl |
| Phenyl | Me | 2-(3-Chlorothienyl) | t-Bu | Me | 2-(3-Chlorothienyl) |
| Phenyl | Me | 1-Cyclohexenyl | t-Bu | Me | 1-Cyclohexenyl |
| Phenyl | Me | 1-Cyclopentenyl | t-Bu | Me | 1-Cyclopentenyl |
| Phenyl | Me | 2-Tetrahydropyranyl | t-Bu | Me | 2-Tetrahydropyranyl |
| Phenyl | Me | 2-Tetrahydrofuryl | t-Bu | Me | 2-Tetrahydrofuryl |
| Phenyl | Me | 3-F-Phenyl | t-Bu | Me | 3-F-Phenyl |
| Phenyl | Me | 4-F-Phenyl | t-Bu | Me | 4-F-Phenyl |
| Phenyl | Me | 2,4-diF-Phenyl | t-Bu | Me | 2,4-diF-Phenyl |
| Phenyl | Me | 2,5-diF-Phenyl | t-Bu | Me | 2,5-diF-Phenyl |
| Phenyl | Me | 2-Cl, 4-F-Phenyl | t-Bu | Me | 2-Cl, 4-F-Phenyl |
| Phenyl | Me | 2,4,6-triF-Phenyl | t-Bu | Me | 2,4,6-triF-Phenyl |
| t-Bu | Et | 2-CN-Phenyl | t-Bu | Et | 2-Pyrazinyl |
| t-Bu | Et | 2-Br-Phenyl | t-Bu | Et | 5-Isoxazolyl |
| t-Bu | Et | 2-I-Phenyl | t-Bu | Et | 2-(3-Chlorothienyl) |
| t-Bu | Et | 2-CF$_3$-Phenyl | t-Bu | Et | 1-Cyclohexenyl |
| t-Eu | Et | 2-OMe-Phenyl | t-Bu | Et | 1-Cyclopentenyl |
| t-Bu | Et | 2-OH-Phenyl | t-Bu | Et | 2-Tetrahydropyranyl |
| t-Bu | Et | 2-OCHF$_2$-Phenyl | t-Bu | Et | 2-Tetrahydrofuryl |
| t-Bu | Et | 2-Ethynyl-Phenyl | t-Bu | Et | 3-F-Phenyl |
| t-Bu | Et | 2-Ethenyl-Phenyl | t-Bu | Et | 4-F-Phenyl |
| t-Bu | Et | 2-SMe-Phenyl | t-Bu | Et | 2,4-diF-Phenyl |
| t-Bu | Et | 2-Pyridyl | t-Bu | Et | 2,5-diF-Phenyl |
| t-Bu | Et | 2-Thienyl | t-Bu | Et | 2-Cl, 4-F-Phenyl |
| t-Bu | Et | 4-Thiazolyl | t-Bu | Et | 2,4,6-triF-Phenyl |

TABLE 2

$R^2 = R^3 = R^4 = R^5 = R^7 = H$; $Q = CH_2W$; $R^1 = CR^9R^{10}X$

| $R^6$ | $R^9$ | $R^{10}$ | X | W |
|---|---|---|---|---|
| Me | Me | Me | CN | Phenyl |
| Me | Me | Me | CN | 2-Cl-Phenyl |
| Me | Me | Me | CN | 2-F-Phenyl |
| Me | Me | Me | CN | 2-Me-Phenyl |
| Me | Me | Me | CN | 2,6-diCl-Phenyl |
| Me | Me | Me | CN | 2,6-diF-Phenyl |
| Me | Me | Me | $CO_2Me$ | Phenyl |
| Me | Me | Me | $CO_2Me$ | 2-Cl-Phenyl |
| Me | Me | Me | $CO_2Me$ | 2-F-Phenyl |
| Me | Me | Me | $CO_2Me$ | 2-Me-Phenyl |
| Me | Me | Me | $CO_2Me$ | 2,6-diCl-Phenyl |
| Me | Me | Me | $CO_2Me$ | 2,6-diF-Phenyl |
| Me | Me | Me | $CO_2Et$ | Phenyl |
| Me | Me | Me | $CO_2Et$ | 2-Cl-Phenyl |
| Me | Me | Me | $CO_2Et$ | 2-F-Phenyl |
| Me | Me | Me | $CO_2Et$ | 2-Me-Phenyl |
| Me | Me | Me | $CO_2Et$ | 2,6-diCl-Phenyl |
| Me | Me | Me | $CO_2Et$ | 2,6-diF-Phenyl |
| Me | Me | Me | $OCH_3$ | Phenyl |
| Me | Me | Me | $OCH_3$ | 2-Cl-Phenyl |
| Me | Me | Me | $OCH_3$ | 2-F-Phenyl |
| Me | Me | Me | $OCH_3$ | 2-Me-Phenyl |
| Me | Me | Me | $OCH_3$ | 2,6-diCl-Phenyl |
| Me | Me | Me | $OCH_3$ | 2,6-diF-Phenyl |
| Me | Me | Me | $OCH_2CH_3$ | Phenyl |
| Me | Me | Me | $OCH_2CH_3$ | 2-Cl-Phenyl |
| Me | Me | Me | $OCH_2CH_3$ | 2-F-Phenyl |
| Me | Me | Me | $OCH_2CH_3$ | 2-Me-Phenyl |
| Me | Me | Me | $OCH_2CH_3$ | 2,6-diCl-Phenyl |
| Me | Me | Me | $OCH_2CH_3$ | 2,6-diF-Phenyl |
| Me | Me | Me | $CH_2OCH_2CH_3$ | Phenyl |
| Me | Me | Me | $CH_2OCH_2CH_3$ | 2-Cl-Phenyl |
| Me | Me | Me | $CH_2OCH_2CH_3$ | 2-F-Phenyl |
| Me | Me | Me | $CH_2OCH_2CH_3$ | 2-Me-Phenyl |
| Me | Me | Me | $CH_2OCH_2CH_3$ | 2,6-diCl-Phenyl |
| Me | Me | Me | $CH_2OCH_2CH_3$ | 2,6-diF-Phenyl |
| Me | Me | Me | $CH_2OCH_3$ | Phenyl |
| Me | Me | Me | $CH_2OCH_3$ | 2-Cl-Phenyl |
| Me | Me | Me | $CH_2OCH_3$ | 2-F-Phenyl |
| Me | Me | Me | $CH_2OCH_3$ | 2-Me-Phenyl |
| Me | Me | Me | $CH_2OCH_3$ | 2,6-diCl-Phenyl |
| Me | Me | Me | $CH_2OCH_3$ | 2,6-diF-Phenyl |
| Me | H | H | CN | Phenyl |
| Me | H | H | CN | 2-Cl-Phenyl |
| Me | H | H | CN | 2-F-Phenyl |
| Me | H | H | CN | 2-Me-Phenyl |
| Me | H | H | CN | 2,6-diCl-Phenyl |
| Me | H | H | CN | 2,6-diF-Phenyl |
| Me | H | H | $CO_2Me$ | Phenyl |
| Me | H | H | $CO_2Me$ | 2-Cl-Phenyl |
| Me | H | H | $CO_2Me$ | 2-F-Phenyl |
| Me | H | H | $CO_2Me$ | 2-Me-Phenyl |
| Me | H | H | $CO_2Me$ | 2,6-diCl-Phenyl |
| Me | H | H | $CO_2Me$ | 2,6-diF-Phenyl |
| Me | H | H | $CO_2Et$ | Phenyl |
| Me | H | H | $CO_2Et$ | 2-Cl-Phenyl |
| Me | H | H | $CO_2Et$ | 2-F-Phenyl |
| Me | H | H | $CO_2Et$ | 2-Me-Phenyl |
| Me | H | H | $CO_2Et$ | 2,6-diCl-Phenyl |
| Me | H | H | $CO_2Et$ | 2,6-diF-Phenyl |
| Me | H | H | $OCH_3$ | Phenyl |
| Me | H | H | $OCH_3$ | 2-Cl-Phenyl |
| Me | H | H | $OCH_3$ | 2-F-Phenyl |
| Me | H | H | $OCH_3$ | 2-Me-Phenyl |
| Me | H | H | $OCH_3$ | 2,6-diCl-Phenyl |
| Me | H | H | $OCH_3$ | 2,6-diF-Phenyl |
| Me | H | H | $OCH_2CH_3$ | Phenyl |
| Me | H | H | $OCH_2CH_3$ | 2-Cl-Phenyl |
| Me | H | H | $OCH_2CH_3$ | 2-F-Phenyl |
| Me | H | H | $OCH_2CH_3$ | 2-Me-Phenyl |
| Me | H | H | $OCH_2CH_3$ | 2,6-diCl-Phenyl |
| Me | H | H | $OCH_2CH_3$ | 2,6-diF-Phenyl |
| Me | H | H | $CH_2OCH_2CH_3$ | Phenyl |
| Me | H | H | $CH_2OCH_2CH_3$ | 2-Cl-Phenyl |
| Me | H | H | $CH_2OCH_2CH_3$ | 2-F-Phenyl |
| Me | H | H | $CH_2OCH_2CH_3$ | 2-Me-Phenyl |
| Me | H | H | $CH_2OCH_2CH_3$ | 2,6-diCl-Phenyl |
| Me | H | H | $CH_2OCH_2CH_3$ | 2,6-diF-Phenyl |
| Me | H | H | $CH_2OCH_3$ | Phenyl |
| Me | H | H | $CH_2OCH_3$ | 2-Cl-Phenyl |
| Me | H | H | $CH_2OCH_3$ | 2-F-Phenyl |
| Me | H | H | $CH_2OCH_3$ | 2-Me-Phenyl |
| Me | H | H | $CH_2OCH_3$ | 2,6-diCl-Phenyl |
| Me | H | H | $CH_2OCH_3$ | 2,6-diF-Phenyl |

TABLE 3

$Q = CHW$ with $R^8$

| $R^1$ | $R^2$ | $R^3$ | $R^4$ | $R^5$ | $R^6$ | $R^7$ | $R^8$ | W |
|---|---|---|---|---|---|---|---|---|
| Et | Me | H | H | H | Me | H | H | Phenyl |
| Et | Me | Me | H | H | Me | H | H | Phenyl |
| Et | H | H | Me | H | Me | H | H | Phenyl |
| Et | H | H | Me | Me | Me | H | H | Phenyl |
| Et | H | H | H | H | Me | Me | H | Phenyl |
| Et | Me | Me | Me | Me | Me | H | H | Phenyl |
| i-Pr | Me | H | H | H | Me | H | H | Phenyl |
| i-Pr | Me | Me | H | H | Me | H | H | Phenyl |
| i-Pr | Me | H | Me | H | Me | H | H | Phenyl |
| i-Pr | H | H | H | H | Me | Me | H | Phenyl |
| t-Bu | Me | H | H | H | Me | H | H | Phenyl |
| t-Bu | Me | Me | H | H | Me | H | H | Phenyl |
| t-Bu | H | H | Me | H | Me | H | H | Phenyl |
| t-Bu | Me | Me | Me | Me | Me | H | H | Phenyl |
| t-Bu | H | H | H | H | Me | Me | H | Phenyl |
| Phenyl | Me | H | H | H | Me | H | H | Phenyl |
| Phenyl | Me | Me | H | H | Me | H | H | Phenyl |
| Phenyl | Me | Me | Me | Me | Me | H | H | Phenyl |
| Phenyl | H | H | Me | Me | Me | H | H | Phenyl |
| Phenyl | H | H | Me | H | Me | H | H | Phenyl |
| Phenyl | H | H | H | H | Me | Me | H | Phenyl |

TABLE 4

$R^2–R^5 = H$  $R^7 = H$
$R^{17} = R^{18} = R^{19} = H$

| $R^1$ | $R^6$ | Q | $R^1$ | $R^6$ | Q |
|---|---|---|---|---|---|
| Et | Me | Q-1 | t-Bu | Me | Q-1 |
| Et | Me | Q-2 | t-Bu | Me | Q-2 |
| Et | Me | Q-3 | t-Bu | Me | Q-3 |
| Et | Me | Q-4 | t-Bu | Me | Q-4 |
| Et | Me | Q-5 | t-Bu | Me | Q-5 |
| Et | Me | Q-6 | t-Bu | Me | Q-6 |
| Et | Me | Q-7 | t-Bu | Me | Q-7 |
| Et | Me | Q-8 | t-Bu | Me | Q-8 |
| Et | Me | Q-9 | t-Bu | Me | Q-9 |
| Et | Me | Q-10 | t-Bu | Me | Q-10 |
| Et | Me | Q-11 | t-Bu | Me | Q-11 |
| Et | Me | Q-12 | t-Bu | Me | Q-12 |
| Et | Me | Q-13 | t-Bu | Me | Q-13 |
| Et | Me | Q-14 | t-Bu | Me | Q-14 |
| i-Pr | Me | Q-1 | Phenyl | Me | Q-1 |
| i-Pr | Me | Q-2 | Phenyl | Me | Q-2 |
| i-Pr | Me | Q-3 | Phenyl | Me | Q-3 |
| i-Pr | Me | Q-4 | Phenyl | Me | Q-4 |
| i-Pr | Me | Q-5 | Phenyl | Me | Q-5 |
| i-Pr | Me | Q-6 | Phenyl | Me | Q-6 |
| i-Pr | Me | Q-7 | Phenyl | Me | Q-7 |
| i-Pr | Me | Q-8 | Phenyl | Me | Q-8 |

TABLE 4-continued $R^2$–$R^5$ = H  $R^7$ = H
$R^{17}$ = $R^{18}$ = $R^{19}$ = H

| $R^1$ | $R^6$ | Q | $R^1$ | $R^6$ | Q |
| --- | --- | --- | --- | --- | --- |
| i-Pr | Me | Q-9 | Phenyl | Me | Q-9 |
| i-Pr | Me | Q-10 | Phenyl | Me | Q-10 |
| i-Pr | Me | Q-11 | Phenyl | Me | Q-11 |
| i-Pr | Me | Q-12 | Phenyl | Me | Q-12 |
| i-Pr | Me | Q-13 | Phenyl | Me | Q-13 |
| i-Pr | Me | Q-14 | Phenyl | Me | Q-14 |
| Et | Et | Q-1 | t-Bu | Et | Q-1 |
| Et | Et | Q-2 | t-Bu | Et | Q-2 |
| Et | Et | Q-3 | t-Bu | Et | Q-3 |
| Et | Et | Q-4 | t-Bu | Et | Q-4 |
| Et | Et | Q-5 | t-Bu | Et | Q-5 |
| Et | Et | Q-6 | t-Bu | Et | Q-6 |
| Et | Et | Q-7 | t-Bu | Et | Q-7 |
| Et | Et | Q-8 | t-Bu | Et | Q-8 |
| Et | Et | Q-9 | t-Bu | Et | Q-9 |
| Et | Et | Q-10 | t-Bu | Et | Q-10 |
| Et | Et | Q-11 | t-Bu | Et | Q-11 |
| Et | Et | Q-12 | t-Bu | Et | Q-12 |
| Et | Et | Q-13 | t-Bu | Et | Q-13 |
| Et | Et | Q-14 | t-Bu | Et | Q-14 |
| i-Pr | Et | Q-1 | Phenyl | Et | Q-1 |
| i-Pr | Et | Q-2 | Phenyl | Et | Q-2 |
| i-Pr | Et | Q-3 | Phenyl | Et | Q-3 |
| i-Pr | Et | Q-4 | Phenyl | Et | Q-4 |
| i-Pr | Et | Q-5 | Phenyl | Et | Q-5 |
| i-Pr | Et | Q-6 | Phenyl | Et | Q-6 |
| i-Pr | Et | Q-7 | Phenyl | Et | Q-7 |
| i-Pr | Et | Q-8 | Phenyl | Et | Q-8 |
| i-Pr | Et | Q-9 | Phenyl | Et | Q-9 |
| i-Pr | Et | Q-10 | Phenyl | Et | Q-10 |
| i-Pr | Et | Q-11 | Phenyl | Et | Q-11 |
| i-Pr | Et | Q-12 | Phenyl | Et | Q-12 |
| i-Pr | Et | Q-13 | Phenyl | Et | Q-13 |
| i-Pr | Et | Q-14 | Phenyl | Et | Q-14 |

TABLE 5

Q = CH$_2$W

| $R^1$ | $R^2$ | $R^3$ | $R^4$ | n | W |
| --- | --- | --- | --- | --- | --- |
| t-Bu | H | H | H | 1 | Phenyl |
| t-Bu | H | H | H | 2 | Phenyl |
| i-Pr | H | H | H | 1 | Phenyl |
| i-Pr | H | H | H | 2 | Phenyl |
| Phenyl | H | H | H | 1 | Phenyl |
| Phenyl | H | H | H | 2 | Phenyl |
| t-Bu | H | H | H | 1 | 2-F Phenyl |
| t-Bu | H | H | H | 2 | 2-F Phenyl |
| i-Pr | H | H | H | 1 | 2-F Phenyl |
| i-Pr | H | H | H | 2 | 2-F Phenyl |
| Phenyl | H | H | H | 1 | 2-F Phenyl |
| Phenyl | H | H | H | 2 | 2-F Phenyl |
| t-Bu | H | H | H | 1 | 2,6-di-F-Phenyl |
| t-Bu | H | H | H | 1 | 2,6-di-Cl-Phenyl |
| t-Bu | H | H | H | 1 | 2-Cl,6-F-Phenyl |
| t-Bu | H | H | H | 1 | 2-Cl-Phenyl |
| t-Bu | H | H | H | 1 | 2-Me-Phenyl |
| t-Bu | H | H | H | 2 | 2,6-di-F-Phenyl |
| t-Bu | H | H | H | 2 | 2,6-di-Cl-Phenyl |
| t-Bu | H | H | H | 2 | 2-Cl,6-F-Phenyl |
| t-Bu | H | H | H | 2 | 2-Cl-Phenyl |
| t-Bu | H | H | H | 2 | 2-Me-Phenyl |
| t-Bu | Me | H | H | 2 | Phenyl |
| t-Bu | Me | Me | H | 2 | Phenyl |

TABLE 5-continued

Q = CH$_2$W

| $R^1$ | $R^2$ | $R^3$ | $R^4$ | n | W |
| --- | --- | --- | --- | --- | --- |
| t-Bu | H | H | Me | 2 | Phenyl |

TABLE 6

Q = CH$_2$W

| $R^3$ | $R^4$ | $R^5$ | $R^6$ | $R^7$ | n | W |
| --- | --- | --- | --- | --- | --- | --- |
| H | H | H | H | H | 1 | Phenyl |
| H | H | H | Me | H | 1 | Phenyl |
| H | H | H | Et | H | 1 | Phenyl |
| H | H | H | Me | H | 2 | Phenyl |
| H | H | H | Et | H | 2 | Phenyl |
| H | H | H | Me | H | 1 | 2-F-Phenyl |
| H | H | H | Et | H | 1 | 2,6-di-F-Phenyl |
| H | H | H | Me | H | 1 | 2,6-di-Cl-Phenyl |
| H | H | H | Me | H | 1 | 2-Cl-6-F Phenyl |
| H | H | H | Me | H | 1 | 2-Cl-Phenyl |
| H | H | H | Me | H | 1 | 2-Me-Phenyl |
| H | H | H | Me | H | 2 | 2-F Phenyl |
| H | H | H | Me | H | 2 | 2,6-di-F-Phenyl |
| H | H | H | Me | H | 2 | 2,6-di-Cl-Phenyl |
| H | H | H | Me | H | 2 | 2-Cl,6-F-Phenyl |
| H | H | H | Me | H | 2 | 2-Cl-Phenyl |
| H | H | H | Me | H | 2 | 2-Me-Phenyl |

TABLE 7

Q = CH$_2$W

| $R^6$ | $R^{20}$ | $R^{21}$ | n | W |
| --- | --- | --- | --- | --- |
| Me | Me | Me | 1 | Phenyl |
| Me | Me | Me | 2 | Phenyl |
| Et | Me | Me | 1 | Phenyl |
| Et | Me | Me | 2 | Phenyl |
| n-Pr | Me | Me | 1 | Phenyl |
| n-Pr | Me | Me | 2 | Phenyl |
| Me | Me | Me | 1 | 2-F-Phenyl |
| Me | Me | Me | 2 | 2-F-Phenyl |
| Et | Me | Me | 1 | 2-F-Phenyl |
| Et | Me | Me | 2 | 2-F-Phenyl |
| n-Pr | Me | Me | 1 | 2-F-Phenyl |
| n-Pr | Me | Me | 2 | 2-F-Phenyl |
| Me | Me | Me | 1 | 2,6-di-F-Phenyl |
| Me | Me | Me | 2 | 2,6-di-F-Phenyl |
| Et | Me | Me | 1 | 2,6-di-F-Phenyl |
| Et | Me | Me | 2 | 2,6-di-F-Phenyl |
| n-Pr | Me | Me | 1 | 2,6-di-F-Phenyl |
| n-Pr | Me | Me | 2 | 2,6-di-F-Phenyl |

TABLE 8

[Structure: bicyclic indane-oxazine with substituents (Q)n on aromatic ring, N-O ring, R⁶ and O-Q group; Q = CH₂W]

| R⁶ | n | W |
|---|---|---|
| Me | 1 | Phenyl |
| Me | 2 | Phenyl |
| Et | 1 | Phenyl |
| Et | 2 | Phenyl |
| n-Pr | 1 | Phenyl |
| n-Pr | 2 | Phenyl |
| Me | 1 | 2-F-Phenyl |
| Me | 2 | 2-F-Phenyl |
| Et | 1 | 2-F-Phenyl |
| Et | 2 | 2-F-Phenyl |
| n-Pr | 1 | 2-F-Phenyl |
| n-Pr | 2 | 2-F-Phenyl |
| Me | 1 | 2,6-di-F-Phenyl |
| Me | 2 | 2,6-di-F-Phenyl |
| Et | 1 | 2,6-di-F-Phenyl |
| Et | 2 | 2,6-di-F-Phenyl |
| n-Pr | 1 | 2,6-di-F-Phenyl |
| n-Pr | 2 | 2,6-di-F-Phenyl |

Formulations

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid diluent(s). More specifically, they will contain these ingredients in the following approximate proportions:

TABLE 5

| | Weight Percent* Active | | |
|---|---|---|---|
| | Ingredient | Diluent(s) | Surfactant(s) |
| Wettable Powders | 5–60 | 39–94 | 1–10 |
| Emulsifiable Concentrates | 3–80 | 20–95 | 0–20 |
| Dusts | 1–25 | 70–99 | 0–5 |
| Granules and Pellets | 0.1–50 | 50–99.9 | 0–15 |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are some times desirable, and are achieved by incorporation into the formulation or by tank mixing.

Typical solid diluents are described in Watkins, et al., "Handbook of Insecticide Dust Diluents and Carriers", 2nd Ed Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide, " 2nd Ed., Interscience, New York, 1950. Solubility under 0.1% is preferred for suspension concentrates; solution concentrates are preferably stable against phase separation at 0°C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration" *Chemical Engineering*, Dec. 4, 1967, pp. 147ff. and "Perry's Chemical Engineer's Handbook", 5th Ed., McGraw-Hill, New York, 1973, pp. 8–57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138–140, 162–164, 166, 167 and 169–182;

H. Gysin and E. Knusli, U.S. Pat. No. 2,891,855, Jun. 23, 1959, Col. 3, line 66 through Col. 5, line 17 and Examples 1–4;

G. C. Klingman, "Weed Control as a Science", John Wiley and Sons, Inc., New York, 1961, pp. 81–96; and J. D. Fryer and S. A. Evans, "Weed Control Handbook", 5th Ed., Blackwell Scientific Publications, Oxford, 1968, pp. 101–103.

In the following examples, all parts are by weight unless otherwise indicated.

EXAMPLE A

Wettable Powder

| | |
|---|---|
| 3-(1,1-dimethylethyl)-6-[[(2-fluorophenyl)methoxy]methyl]-5,6-dihydro-6-methyl-4H-1,2-oxazine | 60% |
| sodium alkylnaphthalenesulfonate | 2% |
| sodium ligninsulfonate | 2% |
| synthetic amorphous silica | 36% |

The active ingredient is first sprayed onto the amorphous silica, then the ingredients are blended, hammer-milled until all the solids are essentially under 50 microns, reblended, and packaged.

EXAMPLE B

Wettable Powder

| | |
|---|---|
| 3-(1,1-dimethylethyl)-6-[[(2-fluorophenyl)methoxy]methyl]-5,6-dihydro-6-methyl-4H-1,2-oxazine | 50% |
| sodium alkylnaphthalenesulfonate | 2% |
| low viscosity methyl cellulose | 2% |
| diatomaceous earth | 46% |

The active ingredient is first sprayed onto the diatomaceous earth then the ingredients are blended, coarsely hammer-milled and then air-milled to produce particles essentially all below 10 microns in diameter. The product is reblended before packaging.

EXAMPLE C

Granule

| | |
|---|---|
| Wettable Powder of Example B | 5% |
| attapulgite granules (U.S.S. 20–40 mesh; 0.84–0.42 mm) | 95% |

A slurry of wettable powder containing 25% solids is sprayed on the surface of attapulgite granules in a double-cone blender. The granules are dried and packaged.

EXAMPLE D

Emulsifiable Concentrate

| | |
|---|---|
| 3-(1,1-dimethylethyl)-6-[[(2-fluorophenyl)methoxy]methyl]-5,6-dihydro-6-methyl-4H-1,2-oxazine | 40% |
| Atlox 3403F | 3% |
| Atlox 3404F | 3% |
| xylene | 54% |

The active ingredient and Atlox emulsifiers are dissolved in the solvent, filtered and packaged. Atlox 3403F and 3404F are blends of anionic and ionic emulsifiers from ICI Americas, Inc.

EXAMPLE E

Low Strength Granule

| | |
|---|---|
| 3-(1,1-dimethylethyl)-6-[[(2-fluorophenyl)methoxy]methyl]-5,6-dihydro-6-methyl-4H-1,2-oxazine | 5% |
| attapulgite granules (U.S.S. 20–40 mesh) | 95% |

The active ingredient is dissolved in a solvent and the solution is sprayed upon dedusted granules in a double-cone blender. After spraying of the solution has been completed, the material is warmed to evaporate the solvent. The material is allowed to cool and then packaged.

EXAMPLE F

Granule

| | |
|---|---|
| 3-(1,1-dimethylethyl)-6-[[(2-fluorophenyl)methoxy]methyl]-5,6-dihydro-6-methyl-4H-1,2-oxazine | 50% |
| wetting agent | 1% |
| crude ligninsulfonate salt (containing 5–20% of the natural sugars) | 10% |
| attapulgite clay | 39% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14–100 mesh (1410–149 microns), and packaged for use.

EXAMPLE G

Concentrated Emulsion

| | |
|---|---|
| 3-(1,1-dimethylethyl)-6-[[(2-fluorophenyl)methoxy]methyl]-5,6-dihydro-6-methyl-4H-1,2-oxazine | 25% |
| xylene | 25% |
| Atlox 3404F | 5% |
| G1284 | 5% |
| ethylene glycol | 8% |
| water | 32% |

The active ingredient, solvent and emulsifiers are blended together. This solution is added to a mixture of the ethylene glycol and water with stirring.

EXAMPLE H

Solution

| | |
|---|---|
| 3-(1,1-dimethylethyl)-6-[[(2-fluorophenyl)methoxy]methyl]-5,6-dihydro-6-methyl-4H-1,2-oxazine | 5% |
| water | 95% |

The compound is added directly to the water with stirring to produce the solution, which may then be packaged for use.

EXAMPLE I

Dust

| | |
|---|---|
| 3-(1,1-dimethylethyl)-6-[[(2-fluorophenyl)methoxy]methyl]-5,6-dihydro-6-methyl-4H-1,2-oxazine | 10% |
| attapulgite | 10% |
| Pyrophyllite | 80% |

The active ingredient is sprayed onto the attapulgite and then passed through a hammer-mill to produce particles substantially all below 200 microns. The ground concentrate is then blended with powdered pyrophyllite until homogeneous.

UTILITY

Test results indicate compounds of this invention are active postemergence and, in particular, preemergence herbicides. Many compounds in this invention are useful for the control of selected grass and broadleaf weeds with tolerance to important agronomic crops such as barley (*Hordeum vulgare*), corn (*Zea mays*), cotton (*Gossypium hirsutum*), rape (*Brassica napus*), rice (*Oryza sativa*), sorghum (*Sorghum bicolor*), soybean (*Glycine max*), sugar beet (*Beta vulgaris*), and wheat (*Triticum aestiyum*), and to vegetable crops. Grass and broadleaf weed species controlled include, but are not limited to, barnyardgrass (*Echinochloa crusgalli*), blackgrass (*Alopecurus myosuroides*), crabgrass (*Digitaria* spp.), duck salad (*Heteranthera limosa*), foxtail (*Setaria* spp.), velvetleaf (*Afutilon theophrasti*), lambsquarters (*Chenopodium* spp.), and umbrella sedge (*Cyperus difformis*). Several compounds in this invention are particularly useful for the control of barnyardgrass in upland and paddy rice. Several compounds of this invention are particularly useful to control blackgrass in wheat and barley.

These compounds also have utility for weed control of selected vegetation in specified areas such as around storage tanks, parking lots, highways, and railways; in fallow crop areas; and in citrus and plantation crops such as banana, coffee, oil palm, and rubber. Alternatively, these compounds are useful to modify plant growth.

Rates of application for compounds of this invention are determined by a number of factors. These factors include: formulation selected, method of application, amount and type of vegetation present, growing conditions, etc. In general terms, the subject compounds should be applied at rates from 0.01 to 20 kg/ha with a preferred rate range of 0.03 to 1 kg/ha. Although a small number of compounds show no herbicidal activity at the rates tested, it is anticipated these compounds are herbicidally active at higher application rates. One skilled in the art can easily determine application rates necessary for desired level of weed control.

Compounds of this invention may be used alone or in combination with other commercial herbicides, insecticides, or fungicides. The following list exemplifies some of the herbicides suitable for use in mixtures. A combination of a compound from this invention with one or more of the following herbicides may be particularly useful for weed control.

| Common Name | Chemical Name |
| --- | --- |
| acetochlor | 2-chloro-N-(ethoxymethyl)-N-(2-ethyl-6-methylphenyl)acetamide |
| acifluorfen | 5-[2-chloro-4-(trifluoromethyl)-phenoxy]-2-nitrobenzoic acid |
| aclonifen | 2-chloro-6-nitro-3-phenoxy-benzenamine |
| acrolein | 2-propenal |
| alachlor | 2-chloro-N-(2,6-diethylphenyl)-N-(methoxymethyl)acetamide |
| alloxydim | methyl 2,2-dimethyl-4,6-dioxo-5-[1-[(2-propenyloxy)amino]butylidene]cyclohexanecarboxylate |
| ametryn | N-ethyl-N'-(1-methylethyl)-6-(methylthio)-1,3,5-triazine-2,4-diamine |
| amitrole | 1H-1,2,4-triazol-3-amine |
| AMS | ammonium sulfamate |
| anilofos | S-[2-[(4-chlorophenyl)(1-methylethyl)amino]-2-oxoethyl) O,O-dimethyl phosphorodithioate |
| asulam | methyl [(4-aminophenyl)sulfonyl]carbamate |
| atrazine | 6-chloro-N-ethyl-N'-(1-methylethyl)-1,3,5-triazine-2,4-diamine |
| aziprotryne | 4-azido-N-(1-methylethyl)-6-methylthio-1,3,5-triazin-2-amine |
| azoluron | N-(1-ethyl-1H-pyrazol-5-yl)-N'-phenylurea |
| barban | 4-chloro-2-butynyl 3-chlorocarbamate |
| benazolin | 4-chloro-2-oxo-3(2H)-benzothiazoleacetic acid |
| benfluralin | N-butyl-N-ethyl-2,6-dinitro-4-(trifluoromethyl)benzenamine |
| bensulfuron | 2-[[[[(4,6-dimethoxy-2-pyrimidinyl)amino]methylcarbonyl]amino]sulfonyl]methyl]benzoic acid, methyl ester |
| bensulide | O,O-bis(1-methylethyl) S-[2-[(phenylsulfonyl)amino]ethyl]-phosphorodithioate |
| bentazon | 3-(1-methylethyl)-(1H)-2,1,3-benzothiadiazin-4(3H)-one, 2,2-dioxide |
| benzofluor | N-[4-(ethylthio)-2-(trifluoromethyl)phenyl]methanesulfonamide |
| benzoylprop | N-benzoyl-N-(3,4-dichlorophenyl)-DL-alanine |
| benzthiazuron | N-2-benzothiazolyl-N'-methylurea |
| bialaphos | 4-(hydroxymethylphosphinyl)-L-2-aminobutanoyl-L-alanyl-L-alanine |
| bifenox | methyl 5-(2,4-dichlorophenoxy)-2-nitrobenzoate |
| bromacil | 5-bromo-6-methyl-3-(1-methylpropyl)-2,4(1H,3H)pyrimidinedione |
| *bromobutide | (+)2-bromo-3,3-dimethyl-N-(1-methyl-1-phenylethyl)butanamide |
| bromofenoxim | 3,5-dibromo-4-hydroxybenzaldhyde-O-(2,4-dinitrophenyl)oxime |
| bromoxynil | 3,5-dibromo-4-hydroxybenzonitrile |
| bromuron | N'-(4-bromophenyl)-N,N-dimethylurea |
| buminafos | dibutyl [1-(butylamino)cyclohexyl]phosphonate |
| butachlor | N-(butoxymethyl)-2-chloro-N-(2,6-diethylphenyl)acetamide |
| butamifos | O-ethyl O-(5-methyl-2-nitrophenyl)(1methylpropyl)phosphoramidothioate |
| buthidazole | 3-[5-(1,1-dimethylethyl)-1,3,4-thiadiazol-2-yl]-4-hydroxy-1-methyl-2-imidazolidinone |
| butralin | 4-(1,1-dimethylethyl)-N-(1-methylpropyl)-2,6-dinitrobenzenamine |
| butylate | S-ethyl bis(2-methylpropyl)carbamothioate |
| cacodylic acid | dimethyl arsinic oxide |
| carbetamide | (R)-N-ethyl-2-[[(phenylamino)carbonyl]oxy]propanamide |
| CDAA | 2-chloro-N,N-di-2-propenylacetamide |
| CDEC | 2-chloroallyl diethyldithiocarbamate |
| chlomethoxyfen | 4-(2,4-dichlorophenoxy)-2-methoxy-1-nitrobenzene |
| chloramben | 3-amino-2,5-dichlorobenzoic acid |
| chlorbromuron | 3-(4-bromo-3-chlorophenyl)-1-methoxy-1-methylurea |
| chlorbufam | 1-methyl-2-propynl(3-chlorophenyl)carbamate |
| chlorfenac | 2,3,6-trichlorobenzeneacetic acid |
| chlorflurecol-methyl | methyl 2-chloro-9-hydroxy-9H-fluorene-9-carboxylate |
| chloridazon | 5-amino-4-chloro-2-phenyl-3(2H)-pyridazinone |
| chlorimuron | 2-[[[[(4-chloro-6-methoxy-2-pyrimidinyl)ethylamino]carbonyl]amino]-sulfonyl]benzoic acid, ethyl ester |
| chlornitrofen | 1,3,5-trichloro-2-(4-nitrophenoxy)-benzene |
| chloropicrin | trichloronitromethane |
| chloroxuron | N'-[4-(4-chlorophenoxy)phenyl]-N,N-dimethylurea |
| chlorpropham | 1-methylethyl 3-chlorophenylcarbamate |
| chlorsulfuron | 2-chloro-N-[[(4-methoxy-6-methyl-1,3,5-triazin-2-yl)amino]carbonyl]benzenesulfonamide |
| chlorthal-dimethyl | dimethyl 2,3,5,6-tetrachloro-1,4-benzenedicarboxylate |
| chlorthiamid | 2,6-dichlorobenzene carbothioamide |
| chlortoluron | N'-(3-chloro-4-methylphenyl)-N,N-dimethylurea |
| cinmethylin | exo-1-methyl-4-(1-methylethyl)-2-[(2-methylphenyl)methoxy]-7-oxabicyclo-[2.2.1]heptane |
| clethodim | (E,E)-(+)-2-[1-[[(3-chloro-2-propenyl)oxy]imino]propyl]-5-[2-(ethylthio)propyl]-3-hydroxy-2-cyclohexen-1-one |
| clomazone | 2-[(2-chlorophenyl)methyl]-4,4-dimethyl-3-isoxazolidinone |
| cloproxydim | (E,E)-2-[1-[[(3-chloro-2-propenyl)oxy)imino]butyl]-5-[2-(ethylthio)-propyl]-3-hydroxy-2-cyclohexen-1-one |
| clopyralid | 3,6-dichloro-2-pyridinecarboxylic acid |
| CMA | calcium salt of MAA |
| cyanazine | 2-[[4-chloro-6-(ethylamino)-1,3,5-triazin-2-yl]amino]-2-methylpropanenitrile |
| cycloate | S-ethyl cyclohexylethylcarbamothioate |
| cycloxydim | 2-[1-ethoxyimino)butyl]-3-hydroxy- |

| Common Name | Chemical Name |
|---|---|
| | 5-(tetrahydro-2H-thiopyran-3-yl)-2-cyclohexene-1-one |
| cycluron | 3-cyclooctyl-1,1-dimethylurea |
| cyperquat | 1-methyl-4-phenylpyridinium |
| cyprazine | 2-chloro-4-(cyclopropylamino)-6-(isopropylamino)-s-triazine |
| cyprazole | N-[5-(2-chloro-1,1-dimethylethyl)-1,3,4-thiadiazol-2-yl]-cyclopropanecarboxamide |
| cypromid | 3',4'-dichlorocyclopropanecarboxanilide |
| dalapon | 2,2-dichloropropanoic acid |
| dazomet | tetrahydro-3,5-dimethyl-2H-1,3,5-thiadiazine-2-thione |
| DCPA | dimethyl 2,3,5,6-tetrachloro-1,4-benzenedicarboxylate |
| desmedipham | ethyl [3-[[(phenylamino)carbonyl]oxy]phenyl]carbamate |
| desmetryn | 2-(isopropylamino)-4-(methylamino)-6-(methylthio)-s-triazine |
| diallate | S-(2,3-dichloro-2-propenyl)bis(1-methylethyl)carbamothioate |
| dicamba | 3,6-dichloro-2-methoxybenzoic acid |
| dichlobenil | 2,6-dichlorobenzonitrile |
| dichlorprop | (+)-2-(2,4-dichlorophenoxy)propanoic acid |
| *diclofopmethyl | (+)-2-[4-(2,4-dichlorophenoxy)-phenoxy]propanoic acid, methyl ester |
| diethatyl | N-(chloroacetyl)-N-(2,6-diethylphenyl)glycine |
| difenoxuron | N'-[4-(4-methoxyphenoxy)phenyl]-N,N-dimethylurea |
| difenzoquat | 1,2-dimethyl-3,5-diphenyl-1H-pyrazolium ion |
| diflufenican | N-(2,4-difluorophenyl)-2-(3-trifluoromethylphenoxy)pyridine-3-carboxamide |
| dimefuron | N'-[3-chloro-4-[5-(1,1-dimethylethyl)-2-oxo-1,3,4-oxadiazol-3(2H)-yl]phenyl]-N,N-dimethylurea |
| dimethachlor | 2-chloro-N-(2,6-dimethylphenyl)-N-(2-methoxyethyl)acetamide |
| dimethametryn | N-(1,2-dimethylpropyl)-N'-ethyl-6-(methylthio)-1,3,5-triazine-2,4-diamine |
| dimethipin | 2,3-dihydro-5,6-dimethyl-1,4-dithiin 1,1,4,4-tetraoxide |
| dimethylarsinic | dimethylarsinic acid |
| dinitramine | N3,N3-diethyl-2,4-dinitro-6-(trifluoromethyl)-1,3-benzenediamine |
| dinoseb | 2-(1-methylpropyl)-4,6-dinitrophenol |
| dinoterb | 2-(1,1-dimethylethyl)-4,6-dinitrophenol |
| diphenamid | N,N-dimethyl-α-phenylbenzeneacetamide |
| dipropetryn | 6-(ethylthio)-N,N'-bis(1-methylethyl)-1,3,5-triazine-2,4-diamine |
| diquat | 6,7-dihydrodipyrido[1,2-a:2',1'-c]-pyrazinediium ion |
| diuron | N'-(3,4-dichlorophenyl)-N,N-dimethylurea |
| DNOC | 2-methyl-4,6-dinitrophenol |
| DPX-V9360 | 2-[[(4,6-dimethoxypyrimidin-2-yl)-aminocarbonyl]aminosulfonyl]-N,N-dimethyl 3-pyridinecarboxamide |
| DSMA | disodium salt of MAA |
| dymron | N-(4-methylphenyl)-N'-(1-methyl-1-phenylethyl)urea |
| eglinazine-ethyl | N-[4-chloro-6-(ethylamino)-1,3,5-triazin-2-yl]glycine ethyl ester |
| endothall | 7-oxabicyclo[2.2.1]heptane-2,3-dicarboxylic acid |
| EPTC | S-ethyl dipropylcarbamothioate |
| ethalfluralin | N-ethyl-N-(2-methyl-2-propenyl)-2,6-dinitro-4-(trifluoromethyl)-benzenamine |
| ethidimuron | N-[5-(ethylsulfonyl)-1,3,4-thiadiazol-2-yl]-N,N'-dimethylurea |
| *ethofumesate | (+)-2-ethoxy-2,3-dihydro-3,3-dimethyl-5-benzofuranyl methanesulfonate |
| fenac | 2,3,6-trichlorobenzeneacetic acid |
| *fenoprop | (+)-2-(2,4,5-trichlorophenoxy)propanoic acid |
| *fenoxaprop | (+)-2-[4-[(6-chloro-2-benzoxazolyl)oxy]phenyl]propanoic acid |
| fenuron | N,N-dimethyl-N'-phenylurea |
| fenuron TCA | Salt of fenuron and TCA |
| flamprop-M-isopropyl | 1-methylethyl N-benzoyl-N-(3-chloro-4-fluorophenyl)-D-alanine |
| flamprop-methyl | methyl N-benzoyl-N-(3-chloro-4-fluorophenyl)-DL-alaninate |
| *fluazifop | (+)-2-[4-[[5-(trifluoromethyl)-2-pyridinyl]oxy]phenyl]propanoic acid |
| fluazifop-P | (R)-2-[4-[[5-(trifluoromethyl)-2-pyridinyl]oxy]phenyl]propanoic acid |
| fluchloralin | N-(2-chloroethyl)-2,6-dinitro-N-propyl-4-(trifluoromethyl)benzenamine |
| fluometuron | N,N-dimethyl-N'-[3-(trifluoromethyl)phenyl]urea |
| fluralin | N-butyl-N-ethyl-2,6-dinitro-4-(trifluoromethyl)benzenamine |
| fluorodifen | p-nitrophenyl a,a,a-trifluoro-2-nitro-p-tolyl ether |
| fluoroglycofen | carboxymethyl 5-[2-chloro-4-(trifluoromethyl)phenoxy]-2-nitrobenzoate |
| flurecol-butyl | butyl 9-hydroxy-9H-fluorene-9-carboxylate |
| fluridone | 1-methyl-3-phenyl-5-[3-(trifluoromethyl)phenyl]-4(1H)-pyridinone |
| flurochloridone | 3-chloro-4-(chloromethyl)-1-[3-(trifluoromethyl)phenyl]-2-pyrrolidinone |
| fluroxypyr | [(4-amino-3,5-dichloro-6-fluoro-2-pyridinyl)oxy]acetic acid |
| fomesafen | 5-[2-chloro-4-(trifluoromethyl)-phenoxy]-N-(methylsulfonyl)-2-nitrobenzamide |
| fosamine-ammonium | ethyl hydrogen (aminocarbonyl)-phosphonate ammonium ethyl |
| glufosinate-ammonium | ammonium 2-amino-4-(hydroxymethylphosphinyl)butanoate |
| glyphosate | N-(phosphonomethyl)glycine |
| haloxyfop | 2-[4-[[3-chloro-5-(trifluoromethyl)-2-pyridinyl]oxy]phenyl]-propanoic acid |
| hexaflurate | potassium hexafluoroarsenate |
| hexazinone | 3-cyclohexyl-6-(dimethylamino)-1-methyl-1,3,5-triazine-2,4(1H,3H)-dione |
| imazamethabenz | 6-(4-isopropyl-4-methyl-5-oxo-2-imidazolin-2-yl)-m-toluic acid, methyl ester and 6-(4-isopropyl-4-methyl-5-oxo-2-imidazolin-2-yl)-p-toluic acid, methyl ester |
| imazapyr | (+)-2-[4,5-dihydro-4-methyl-4-(1-methylethyl)-5-oxo-1H-imidazol-2-yl]-3-pyridinecarboxylic acid |
| imazaquin | 2-[4,5-dihydro-4-methyl-4-(1-methylethyl)-5-oxo-1H-imidazol-2-yl]-3-quinolinecarboxylic acid |
| imazethapyr | (+)-2-[4,5-dihydro-4-methyl-4-(1-methylethyl)-5-oxo-1H-imidazol-2-yl]-5-ethyl-3-pyridinecarboxylic acid |
| ioxynil | 4-hydroxy-3,5-diiodobenzonitrile |
| isocarbamid | N-(2-methylpropyl)-2-oxo-1-imidazolidinecarboxamide |
| isopropalin | 4-(1-methylethyl)-2,6-dinitro-N,N-dipropylbenzenamine |

-continued

| Common Name | Chemical Name |
|---|---|
| isoproturon | N-(4-isopropylphenyl)-N',N'-dimethylurea |
| isouron | N'-[5-(1,1-dimethylethyl)-3-isoxazolyl]-N,N-dimethylurea |
| isoxaben | N-[3-(1-ethyl-1-methylpropyl)-5-isoxazolyl]-2,6-dimethoxybenzamide |
| karbutilate | 3-[[(dimethylamino)carbonyl]amino]phenyl-(1,1-dimethylethyl)-carbamate |
| lactofen | (+)-2-ethoxy-1-methyl-2-oxoethyl 5-[2-chloro-4-(trifluoromethyl)-phenoxy]-2-nitrobenzoate |
| lenacil | 3-cyclohexyl-6,7-dihydro-1H-cyclopentapyrimidine-2,4(3H,5H)-dione |
| linuron | N'-(3,4-dichlorophenyl)-N-methoxy-N-methylurea |
| MAA | methylarsonic acid |
| MAMA | monoammonium salt of MAA |
| MCPA | (4-chloro-2-methylphenoxy)acetic acid |
| MCPA-thioethyl | S-ethyl (4-chloro-2-methylphenoxy)ethanethioate |
| MCPB | 4-(4-chloro-2-methylphenoxy)-butanoic acid |
| mecoprop | (+)-2-(4-chloro-2-methylphenoxy)-propanoic acid |
| mefenacet | 2-(2-benzothiazolyloxy)-N-methyl-N-phenyl acetamide |
| mefluidide | N-[2,4-dimethyl-5-[[(trifluoromethyl)sulfonyl]amino]phenyl]-acetamide |
| metamitron | 4-amino-3-methyl-6-phenyl-1,2,4-triazin-5(4H)-one |
| metazachlor | 2-chloro-N-(2,6-dimethylphenyl)-N-(1(H)-pyrazol-1-ylmethyl)-acetamide |
| methabenzthiazuron | 2,3-dimethyl-3-(2-benzothiazolyl)urea |
| methalpropalin | N-(2-methyl-2-propenyl)-2,6-dinitro-N-propyl-4-(trifluoromethyl)benzenamide |
| metham | methylcarbamodithioic acid |
| methazole | 2-(3,4-dichlorophenyl)-4-methyl-1,2,4-oxadiazolidine-3,5-dione |
| methoxuron | N'-(3-chloro-4-methoxyphenyl)-N,N-dimethylurea |
| methoxyphenone | (4-methoxy-3-methylphenyl)(3-methylphenyl)methanone |
| methyldymron | N-methyl-N'-(1-methyl-1-phenylethyl)-N-phenylurea |
| metobromuron | N'-(4-bromophenyl)-N-methoxy-N-methylurea |
| metolachlor | 2-chloro-N-(2-ethyl-6-methylphenyl)-N-(2-methoxy-1-methylethyl)acetamide |
| metoxuron | N'-(3-chloro-4-methoxyphenyl)-N,N-dimethylurea |
| metribuzin | 4-amino-6-(1,1-dimethylethyl)-3-(methylthio)-1,2,4-triazin-5(4H)-one |
| metsulfuronmethyl | 2-[[[[(4-methoxy-6-methyl-1,3,5-triazin-2-yl)amino]carbonyl]amino]sulfonyl]benzoic acid, methyl ester |
| MH | 1,2-dihydro-3,6-pyridazinedione |
| molinate | S-ethyl hexahydro-1H-azepine-1-carbothioate |
| monalide | N-(4-chlorophenyl)-2,2-dimethylpentanamide |
| monolinuron | 3-(p-chlorophenyl)-1-methoxy-1-methylurea |
| monuron | N'-(4-chlorophenyl)-N,N-dimethylurea |
| MSMA | monosodium salt of MAA |
| naproanilide | 2-(2-naphthalenyloxy)-N-phenylpropanamide |
| napropamide | N,N-diethyl-2-(1-naphthalenyloxy)-propanamide |
| naptalam | 2-[(1-naphthalenylamino)carbonyl]benzoic acid |

-continued

| Common Name | Chemical Name |
|---|---|
| neburon | 1-butyl-3-(3,4-dichlorophenyl)-1-methylurea |
| nitralin | 4-methylsulfonyl-2,6-dinitro-N,N-dipropylaniline |
| nitrofen | 2,4-dichloro-1-(4-nitrophenoxy)-benzene |
| nitrofluorfen | 2-chloro-1-(4-nitrophenoxy)-4-(trifluoromethyl)benzene |
| norea | N,N-dimethyl-N'-(octahydro-4,7-methano-1H-inden-5-yl)urea 3α, 4α,5α,7α,7αa-isomer |
| norflurazon | 4-chloro-5-(methylamino)-2-[3-(trifluoromethyl)phenyl]-3(2H)-pyridazinone |
| orbencarb | S-[2-(chlorophenyl)methyl]diethyl-carbamothioate |
| oryzalin | 4-(dipropylamino)-3,5-dinitro-benzenesulfonamide |
| oxadiazon | 3-[2,4-dichloro-5-(1-methylethoxy)-phenyl]-5-(1,1-dimethylethyl)-1,3,4-oxadiazol-2(3H)-one |
| oxyfluorfen | 2-chloro-1-(3-ethoxy-4-nitrophenoxy)-4-(trifluoromethyl)benzene |
| paraquat | 1,1'-dimethyl-4,4'-dipyridinium ion |
| pebulate | S-propyl butylethylcarbamothioate |
| pendimethalin | N-(1-ethylpropyl)-3,4-dimethyl-2,6-dinitrobenzenamine |
| perfluidone | 1,1,1-trifluoro-N-[2-methyl-4-(phenylsulfonyl)phenyl]methane-sulfonamide |
| phenisopham | 3-[[(1-methylethoxy)carbonyl]amino]phenyl ethylphenylcarbamate |
| phenmedipham | 3-[(methoxycarbonyl)amino]phenyl (3-methylphenyl)carbamate |
| picloram | 4-amino-3,5,6-trichloro-2-pyridine-carboxylic acid |
| piperophos | S-[2-(2-methyl-1-piperidinyl)-2-oxoethyl]O,O-dipropyl phosphorodithioate |
| pretilachlor | 2-chloro-N-(2,6-diethylphenyl)-N-(2-propoxyethyl)acetamide |
| procyazine | 2-[[4-chloro-6-(cyclopropylamino)-1,3,5-triazin-2-yl]amino]-2-methyl-propanenitrile |
| prodiamine | 2,4-dinitro-$N^3,N^3$-dipropyl-6-(trifluoromethyl)-1,3-benzenediamine |
| profluralin | N-(cyclopropylmethyl)-2,6-dinitro-N-propyl-4-(trifluoromethyl)-benzenamine |
| proglinazine-ethyl | N-[4-chloro-6-[(1-methylethyl)-amino]-1,3,5-triazin-2-yl]glycine ethyl ester |
| prometon | 6-methoxy-N,N'-bis(1-methylethyl)-1,3,5-triazine-2,4-diamine |
| prometryn | N,N'-bis(1-methylethyl)-6-(methylthio)-1,3,5-triazine-2,4-diamine |
| pronamide | 3,5-dichloro-N-(1,1-dimethyl-2-propynyl)benzamide |
| propachlor | 2-chloro-N-(1-methylethyl)-N-phenylacetamide |
| propanil | N-(3,4-dichlorophenyl)propanamide |
| propaquizafop | 2-[[(1-methylethylidene)amino]oxy]-ethyl 2-[4-[(6-chloro-2-quinoxalinyl)oxy]phenoxy]propanoate |
| propazine | 6-chloro-N,N'-bis(1-methylethyl)-1,3,5-triazine-2,4-diamine |
| propham | 1-methylethyl phenylcarbamate |
| propyzamide | 3,5-dichloro-N-(1,1-dimethyl-2-propynl)benzamide |
| prosulfalin | N-[[4-(dipropylamino)-3,5-dinitrophenyl]sulfonyl]-S,S-dimethyl-sulfilimine |
| prosulfocarb | S-benzyldipropylthiocarbamate |
| prynachlor | 2-chloro-N-(1-methyl-2-propynyl)-acetanilide |
| pyrazon | 5-amino-4-chloro-2-phenyl-3(2H)- |

| Common Name | Chemical Name |
|---|---|
| pyrazosulfuron-ethyl | pyridazinone<br>ethyl 5-[[[[(4,6-dimethoxy-2-pyrimidinyl)amino]carbonyl]-amino]sulfonyl]-1-methyl-1H-pyrazole-4-carboxylate |
| pyrazoxyfen | 2-[[4-(2,4-dichlorobenzoyl)-1,3-dimethyl-1H-pyrazol-5-yl]oxy]-1-phenylethanone |
| pyridate | O-(6-chloro-3-phenyl-4-pyridazinyl) S-octyl carbonothioate |
| quizalofop ethyl | (+)-2-[4-[(6-chloro-2-quinoxalinyl)-oxy]phenoxy]propanoic acid, ethyl ester |
| secbumeton | N-ethyl-6-methoxy-N'-(1-methylpropyl)-1,3,5-triazine-2,4-diamine |
| sethoxydim | 2-[1-(ethoxyimino)butyl]-5-[2-(ethylthio)propyl]-3-hydroxy-2-cyclohexen-1-one |
| siduron | N-(2-methylcyclohexyl)-N'-phenylurea |
| simazine | 6-chloro-N,N'-diethyl-1,3,5-triazine-2,4-diamine |
| simetryn | N,N'-diethyl-6-(methylthio)-1,3,5-triazine-2,4-diamine |
| sodium chlorate | sodium chlorate |
| sodium monochloroacetate | chloroacetic acid, sodium salt |
| sulfometuron methyl | 2-[[[[(4,6-dimethyl-2-pyrimidinyl)-amino]carbonyl]amino]sulfonyl] benzoic acid, methyl ester |
| 2,4,5-T | (2,4,5-trichlorophenoxy)acetic acid |
| 2,3,6-TBA | 2,3,6-trichlorobenzoic acid |
| TCA | trichloroacetic acid |
| tebutam | 2,2-dimethyl-N-(1-methylethyl)-N-(phenylmethyl)propanamide |
| tebuthiuron | N-[5-(1,1-dimethylethyl)-1,3,4-thiadiazol-2-yl]-N,N'-dimethylurea |
| terbacil | 5-chloro-3-(1,1-dimethylethyl)-6-methyl-2,4(1H,3H)-pyrimidinedione |
| terbuchlor | N-(butoxymethyl)-2-chloro-N-[2-(1,1-dimethylethyl)-6-methylphenyl]-acetamide |
| terbumeton | N-(1,1-dimethylethyl)-N'-ethyl-6-methoxy-1,3,5-triazine-2,4-diamine |
| terbuthylazine | 2-(tert-butylamino)-4-chloro-6-(ethylamino)-s-triazine |
| terbutol | 2,6-di-tert-butyl-p-tolyl methylcarbamate |
| terbutryn | N-(1,1-dimethylethyl)-N'-ethyl-6-(methylthio)-1,3,5-triazine-2,4-diamine |
| thifensulfuron | 3-[[[[(4-methoxy-6-methyl-1,3,5-triazin-2-yl)amino]carbonyl]amino]-sulfonyl]-2-thiophenecarboxylic acid, methyl ester |
| thiameturonmethyl | methyl 3-[[[[(4-methoxy-6-methyl-1,3,5-triazin-2-yl)amino]carbonyl]-amino]sulfonyl]2-thiophenecarboxylate |
| thiazafluron | N,N'-dimethyl-N-[5-(trifluoromethyl)-1,3,4-thiadiazol-2-yl]urea |
| thiobencarb | S-[(4-chlorophenyl)methyl]diethylcarbamothioate |
| tiocarbazil | S-(phenylmethyl) bis(1-methylpropyl)carbamothioate |
| tralkoxydim | 2-[1-(ethoxyimino)propyl]-3-hydroxy-5-(2,4,6-trimethylphenyl)-2-cyclohexen-1-one |
| triallate | S-(2,3,3-trichloro-2-propenyl) bis-(1-methylethyl)carbamothioate |
| triasulfuron | 2-(2-chloroethoxy)-N-[[(4-methoxy-6-methyl-1,3,5-triazin-2-yl)amino]-carbonyl]benzenesulfonamide |
| tribenuron methyl | 2-[[[[N-(4-methoxy-6-methyl-1,3,5-triazine-2-yl)-N-methylamino]-carbonyl]amino]sulfonyl]benzoic acid, methyl ester |
| triclopyr | [(3,5,6-trichloro-2-pyridinyl)oxy]-acetic acid |
| *tridiphane | (+)2-(3,5-dichlorophenyl)-2-(2,2,2-trichloroethyl)oxirane |
| trietazine | 6-chloro-N,N,N'-triethyl-1,3,5-triazine-2,4-diamine |
| trifluralin | 2,6-dinitro-N,N-dipropyl-4-(trifluoromethyl)benzenamine |
| trimeturon | 1-(p-chlorophenyl)-2,3,3-trimethylpseudourea |
| 2,4-D | (2,4-dichlorophenoxy)acetic acid |
| 2,4-DB | 4-(2,4-dichlorophenoxy)butanoic acid |
| vernolate | S-propyl dipropylcarbamothioate |
| xylachlor | 2-chloro-N-(2,3-dimethylphenyl)-N-(1-methylethyl)acetamide |

BIOLOGICAL TABLE
(Formula I, Q = CH$_2$W)

| Compd. No. | R$^1$ | R$^2$ | R$^3$ | R$^4$ | R$^5$ | R$^6$ | W |
|---|---|---|---|---|---|---|---|
| 1 | Ph | H | H | H | H | Me | 2-F-Phenyl |
| 2 | Ph | H | H | H | H | Me | 2,6-diF-Phenyl |
| 3 | Ph | H | H | H | H | Me | Phenyl |
| 4 | t-Bu | H | H | H | H | Me | 2-F-Phenyl |
| 5 | t-Bu | H | H | H | H | Me | Phenyl |
| 6 | t-Bu | H | H | H | H | Me | 2,6-diF-Phenyl |
| 7 | t-Bu | H | H | H | H | Et | 2,6-diF-Phenyl |
| 8 | t-Bu | H | H | H | H | Et | 2-F-Phenyl |
| 9 | t-Bu | H | H | H | H | Et | Phenyl |
| 10 | t-Bu | H | H | H | H | Et | 2-Cl, 6-F-Phenyl |
| 11 | t-Bu | H | H | H | H | Et | 2-Me-Phenyl |
| 12 | t-Bu | H | H | H | H | Me | 2-Me-Phenyl |
| 13 | t-Bu | H | H | H | H | Me | 2-tetrahydropyranyl |
| 14 | t-Bu | H | H | H | H | Me | 2-pyridinyl |
| 15 | t-Bu | H | H | H | H | Me | 2-Cl-Phenyl |
| 16 | t-Bu | H | H | H | H | Me | 2-Cl, 6-F-Phenyl |
| 17 | t-Bu | H | H | H | H | Me | 2-Br-Phenyl |
| 18 | t-Bu | H | H | H | H | Me | 2,6-diCl-Phenyl |

(R$^2$=R$^3$=R$^4$=R$^5$=H)

| Compd. No. | R$^1$ | R$^6$ | W |
|---|---|---|---|
| 19 | Ph | Et | 2,6-diF-Phenyl |
| 20 | Ph | Me | 2-Cl-Phenyl |
| 21 | t-Bu | H | Phenyl |
| 22 | t-Bu | H | 2-F-Phenyl |
| 23 | t-Bu | H | 2,6-diF-Phenyl |
| 24 | t-Bu | H | 2-Cl, 6-F-Phenyl |
| 25 | i-Pr | Me | 2-F-Phenyl |
| 26 | i-Pr | Me | 2,6-diF-Phenyl |
| 29 | See Following Table | | |
| 30 | See Following Table | | |
| 31 | See Following Table | | |
| 32 | See Following Table | | |
| 33 | i-Bu | Me | 2,6-diF-Phenyl |
| 34 | i-Bu | Me | 2-F-Phenyl |
| 35 | Me | Me | 2,6-diF-Phenyl |
| 36 | t-Bu | Me | 5-thiazolyl |
| 37 | See Following Table | | |
| 38 | t-Bu | i-Pr | 2-F-Phenyl |
| 39 | t-Bu | i-Pr | 2,6-diF-Phenyl |
| 40 | t-Bu | i-Pr | 2-Cl, 6-F-Phenyl |
| 41 | t-Bu | n-Pr | 2-Cl, 6-F-Phenyl |
| 42 | t-Bu | n-Pr | 2,6-diF-Phenyl |
| 43 | t-Bu | n-Pr | 2-F-Phenyl |
| 44 | t-Bu | i-Pr | Phenyl |
| 45 | See Following Table | | |
| 46 | t-Bu | i-Pr | 2,6-diCl-Phenyl |
| 47 | See Following Table | | |
| 48 | See Following Table | | |
| 49 | See Following Table | | |
| 50 | See Following Table | | |

-continued

| 51 | See Following Table | | |
| 52 | See Following Table | | |
| 53 | 4-F-Phenyl | Me | 2,6-diF-Phenyl |
| 54 | Phenyl | Et | 2-F-Phenyl |
| 55 | 4-Cl-Phenyl | Me | 2,6-diF-Phenyl |
| 56 | 3-Cl-Phenyl | Me | 2,6-diF-Phenyl |
| 57 | Phenyl | Et | 2-Cl, 6-F-Phenyl |
| 58 | See Following Table | | |
| 59 | See Following Table | | |
| 60 | See Following Table | | |
| 61 | t-Bu | Me | 4,6-dimethoxypyrimid-2-yl |
| 62 | See Following Table | | |
| 63 | 1,1-dimethylbenzyl | Me | 2,6-diF-Phenyl |
| 64 | See Following Table | | |
| 65 | See Following Table | | |
| 66 | 1-methylbenzyl | Me | 2,6-diF-Phenyl |

COMPOUND STRUCTURES TABLE

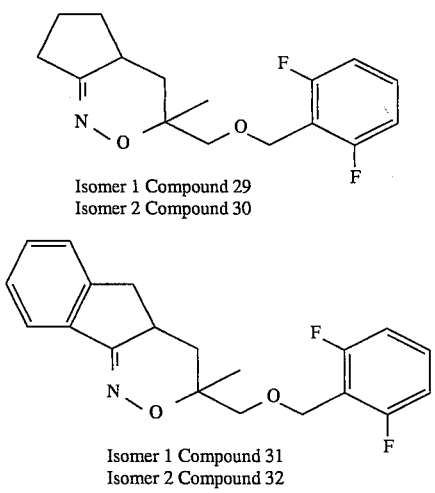

Isomer 1 Compound 29
Isomer 2 Compound 30

Isomer 1 Compound 31
Isomer 2 Compound 32

Racemic Compound 37
R-isomer Compound 51
S-isomer Compound 52

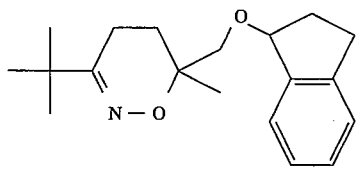

Compound 45

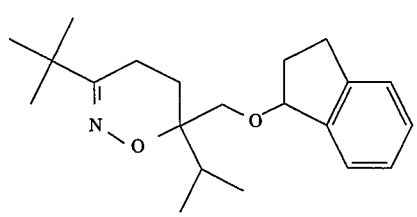

Compound 47

-continued
COMPOUND STRUCTURES TABLE

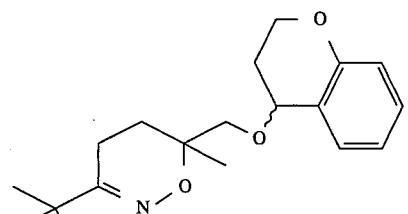

Compound 48

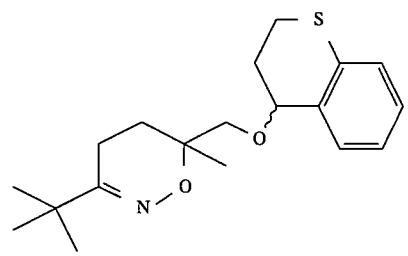

Compound 49

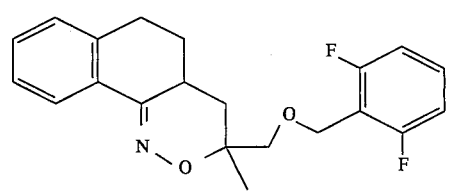

Isomer 1 Compound 58
Isomer 2 Compound 60

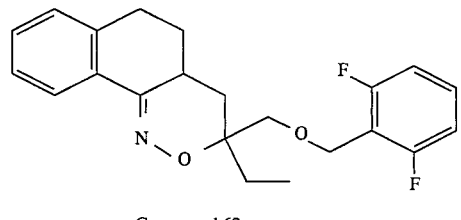

Compound 62

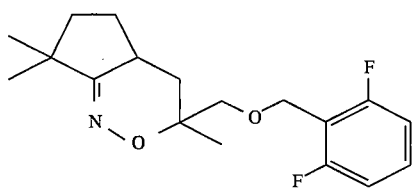

Isomer 1 Compound 64
Isomer 2 Compound 65

NMR DATA FOR BIOLOGICAL TABLE COMPOUNDS AT 200 MHz IN CDCl₃

| CMPD. | |
|---|---|
| 1 | 7.8–7.0 (m, ArH, 9H), 4.6 (s, CH₂O, 2H), 3.5 (m, CH₂O, 2H), 2.5 (m, 2H), 2.1 (m, 1H), 1.9 (m, 1H), 1.34 (s, CH₃, 3H) |
| 2 | 7.7–6.9 (m, ArH, 8H), 4.6 (m, CH₂O, 2H), 3.5 (m, CH₂O, 2H), 2.5–1.7 (m, 4H, CH₂), 1.3 (s, Me, 3H) |
| 3 | 7.7–7.2 (m, ArH, 10H), 4.6 (m, CH₂O, 2H), 3.5 (m, CH₂O, 2H), 2.5–1.8 (m, CH₂, 4H), 1.3 (s, Me, 3H) |
| 4 | 7.5–7.0 (m, ArH, 4H), 4.6 (m, CH₂O, 2H), 3.4 (m, |

NMR DATA FOR BIOLOGICAL TABLE COMPOUNDS AT 200 MHz IN CDCl₃

| CMPD. | |
|---|---|
| | OCH₂, 2H), 2.2–1.5 (m, CH₂, 4H), 1.24 (s, Me, 3H), 1.14 (t, t-Bu, 9H) |
| 5 | 7.3 (m, ArH, 5H), 4.6 (m, CH₂O, 2H), 3.4 (m, CH₂O, 2H), 2.2–1.5 (m, CH₂, 4H), 1.2 (s, Me, 3H), 1.1 (s, t-Bu, 9H) |
| 6 | 7.4–6.8 (m, ArH, 3H), 4.6 (m, CH₂O, 2H), 3.4 (m, CH₂O, 2H), 2.2–1.4 (m, CH₂, 4H), 1.2 (s, Me, 3H), 1.1 (s, t-Bu, 9H) |
| 7 | 7.2–6.9 (m, ArH, 3H), 4.6 (m, CH₂O, 2H), 3.4 (m, CH₂O, 2H), 2.1–1.6 (m, CH₂, 6H), 1.1 (s, t-Bu, 9H), 0.9 (t, Me, 3H) |
| 8 | 7.4–7.0 (m, ArH, 4H), 4.6 (m, CH₂O, 2H), 3.4 (m, CH₂O, 2H), 2.1–1.6 (m, CH₂, 6H), 1.1 (s, t-Bu, 9H), 0.9 (t, Me, 3H) |
| 9 | 7.3 (m, ArH, 5H), 4.55 (m, CH₂O, 2H), 3.36 (m, CH₂O, 2H), 2.1–1.6 (m, CH₂, 6H), 1.1 (s, t-Bu, 9H), 0.9 (t, Me, 3H) |
| 10 | 7.2–6.9 (m, ArH, 3H), 4.7 (m, CH₂O, 2H), 3.39 (m, CH₂O, 2H), 2.1–1.6 (m, CH₂, 6H), 1.1 (s, t-Bu, 9H) |
| 11 | 7.35–7.15 (m, ArH, 4H), 4.5 (m, CH₂O, 2H), 3.38 (m, CH₂O, 2H), 2.33 (s, Me, 3H), 2.1–1.6 (m, CH₂, 6H), 1.1 (s, t-Bu, 9H), 0.9 (t, Me, 3H) |
| 12 | 7.3–7.15 (m, ArH, 4H), 4.6 (m, CH₂O, 2H), 3.4 (m, CH₂O, 2H), 2.3 (s, Me, 3H), 2.1–1.5 (m, CH₂, 6H), 1.24 (s, Me, 3H), 1.1 (s, t-Bu, 9H) |
| 13 | 4.1 (m, 1H), 3.5 (m, CH₂O, 6H), 2.2–1.0 (m, CH₂ and CH₃, 22H) |
| 14 | 8.6 (1H, pyridyl H), 7.7 (1H, ArH), 7.45 (1H, ArH), 7.2 (1H, ArH), 4.7 (m, CH₂O, 2H), 3.5 (m, CH₂O, 2H), 2.2–1.6 (m, CH₂, 4H), 1.27 (s, Me, 3H), 1.14 (s, t-Bu, 9H) |
| 15 | 7.5–7.15 (m, ArH, 4H), 4.6 (m, CH₂O, 2H), 3.5 (m, CH₂O, 2H), 2.2–1.6 (m, CH₂, 4H), 1.3 (s, Me, 3H), 1.1 (s, t-Bu, 9H) |
| 16 | 7.3–6.9 (m, ArH, 3H), 4.7 (m, CH₂O, 2H), 3.4 (m, CH₂O, 2H), 2.1–1.6 (m, CH₂, 4H), 1.2 (s, Me, 3H), 1.1 (s, t-Bu, 9H) |
| 17 | No data |
| 18 | 7.4–7.15 (m, ArH, 3H), 4.82 (m, CH₂O, 2H), 3.5 (m, CH₂O, 2H), 2.1–1.5 (m, CH₂, 4H), 1.2 (s, Me, 3H), 1.1 (s, t-Bu, 9H) |
| 19 | 7.7–6.8 (m, ArH, 8H), 4.6 (m, 2H, CH₂O), 3.5 (s, 2H), 2.5–1.6 (m, 6H, alkyl), 0.9 (t, 3H, Me) |
| 20 | 7.7–7.2 (m, ArH, 9H), 4.7 (m, 2H, CH₂O), 3.6 (2H), 2.6 (2H), 2.2 (1H), 1.8 (1H), 1.3 (Me) |
| 21 | 7.3 (5H), 4.6 (2H), 3.8 (1H), 3.6 (2H), 2.3–1.6 (4H), 1.1 (9H) |
| 22 | 7.5–7.0 (m, ArH, 4H, alkyl), 4.6 (s, 2H, CH₂O), 3.8 (m, 1H), 3.6 (m, 2H), 2.2 (m, 2H), 2.0–1.7 (m, 2H), 1.1 (s, 9H) |
| 23 | 7.2–6.9 (m, 3H, ArH), 4.7 (s, 2H, CH₂O), 3.8 (m, 1H), 3.7 (m, 2H), 2.2 (m, 2H), 2.0–1.7 (m, 2H), 1.1 (s, 9H) |
| 24 | 7.2–6.9 (m, 3H, ArH), 4.7 (m, 2H, CH₂O), 3.8 (1H), 3.7 (m, 2H), 2.2 (m, 2H), 2.0–1.7 (m, 2H), 1.15 (s, 9H) |
| 25 | 7.6–6.9 (m, ArH, 4H), 4.65 (s, 2H), 3.4 (m, 2H), 2.4–1.3 (m, alkyl), 1.2 (s, Me), 1.05 (d, 6H, Me) |
| 26 | 7.3–6.9 (3H, m, ArH), 4.66 (m, 2H), 3.4 (m, 2H), 2.5–1.6 (m, alkyl), 1.2 (s, Me), 1.0 (d, 6H, Me) |
| 29 | 7.2 (1H, m), 6.9 (m, 2H), 4.6 (m, CH₂O, 2H), 3.3 (2xd, 2H, CH₂O), 2.5–1.2 (m, alkyl), 1.3 (Me, s) |
| 30 | 7.2–6.9 (m, ArH), 4.7 (CH₂O, 2H), 3.5 (m, CH₂O, 2H), 2.4–1.2 (m, alkyl), 1.18 (s, Me, 3H) |
| 31 | 7.8–6.8 (m, ArH), 4.7 (CH₂O), 3.5 (CH₂O), 3.2–1.3 (alkyls), 1.3 (s, 3H) |
| 32 | 7.8–6.9 (m, ArH), 4.7 (CH₂O), 3.5 (CH₂O), 3.3–1.2 (alkyl), 1.3 (s, 3H) |
| 33 | 7.2 (m, 1H), 6.9 (m, 2H), 4.5 (m, CH₂O), 4.0 (2H), 3.6 (m, 2H), 3.0 (m, 1H), 2.1–1.5 (m, alkyl), 1.25 (Me), 0.9 (2xm, 6H, Me) |
| 34 | 7.5 (m, 1H), 7.35 (m, 1H), 7.15 (m, 1H), 7.0 (m, 1H), 4.57 (CH₂O), 4.1 and 3.6 (OCH₂), 3.0 (m, CH), 2.15 (d, CH₂), 2.1–1.5 (m, alkyls), 1.2 (s, CH₃), 0.9 (2x Me, 6H) |
| 35 | 7.25 (m, 1H), 6.9 (m, 2H), 4.5 (m, 2H, CH₂O), 4.0 and 3.6 (CH₂O, 2H), 3.0 (m, 1H), 2.1 (m, 1H), 1.99 (3H, Me), 1.9 (m, 1H), 1.55 (1H), 1.26 (s, Me) |
| 36 | 8.8–7.3 (m, ArH, 2H), 4.6 (d, CH₂O, 2H), 3.5 (m, CH₂O, 2H), 2.0 (m, 1H), 1.7 (m, 1H), 1.2 (s, CH₃, 3H), 1.1 (s, t-Bu, 9H) |
| 37 | 7.4–7.23 (m, ArH, 4H), 5.0 (m, CH₃, 1H), 3.45 (m, CH₂O, 2H), 3.0 (m, 1H), 2.8 (m, 1H), 2.4 (m, 1H), 2.0 (m, 3H), 1.24 (s, CH₃, 3H), 1.1 (m, 2H), 1.12 (s, t-Bu, 9H) |
| 38 | 7.5–6.95 (m, ArH, 4H), 4.53 (m, CH₂O, 2H), 3.4 (m, CH₂O, 2H), 2.0 (m, 4H), 1.8 (m, 1H), 1.1 (s, t-Bu, 9H), 0.949 (m, (CH₃)₂, 6H) |
| 39 | 7.26–6.9 (m, ArH, 3H), 4.6 (m, CH₂O, 2H), 3.43 (m, CH₂O, 2H), 2.0 (m, 4H), 1.6 (m, 1H), 1.0 (s, t-Bu, 9H), 0.918 (m, (CH₃)₂, 6H) |
| 40 | 7.2–7.0 (m, ArH, 3H), 4.6 (m, CH₂O, 2H), 3.45 (m, CH₂O, 2H), 2.0 (m, 4H), 1.6 (m, 1H), 1.1 (s, t-Bu, 9H), 0.92 (m, (CH₃)₂, 6H) |
| 41 | 7.26–7.0 (m, ArH, 3H), 4.68 (m, CH₂O, 2H), 3.37 (s, CH₂O, 2H), 2.0 (m, 3H), 1.58 (m, 3H), 1.5 (m, 2H), 1.0 (s, t-Bu, 9H), 0.881 (t, CH₃, 3H) |
| 42 | 7.3–6.88 (m, ArH, 3H), 4.63 (m, CH₂O, 2H), 3.36 (s, CH₂O, 2H), 2.0 (m, 3H), 1.58 (m, 3H), 1.5 (m, 2H), 1.0 (s, t-Bu, 9H), 0.88 (t, CH₃, 3H) |
| 43 | 7.5–7.0 (m, ArH, 4H), 4.61 (m, CH₂O, 2H), 3.38 (s, CH₂O, 2H), 2.0 (m, 3H), 1.6 (m, 3H), 1.4 (m, 2H), 1.2 (s, t-Bu, 9H), 0.9 (t, CH₃, 3H) |
| 44 | 7.3 (s, ArH, 5H), 4.5 (m, CH₂O, 2H), 3.4 (m, CH₂O, 2H), 2.1–1.8 (m, 4H), 17 (m, 1H), 1.2 (s, t-Bu, 9H), 2.0 (m, (CH₃)₂, 6H) |
| 45 | 7.4–7.0 (m, ArH, 4H), 4.9 (m, CH, 1H), 3.4 (m, CH₂O, 2H), 3.0 (m, 1H), 2.8 (m, 1H), 2.4 (m, 1H), 2.0 (m, 4H), 1.6 (m, 1H), 1.2 (d, t-Bu, 9H), 0.95 (m, (CH₃)₂, 6H), (isomers) |
| 46 | 7.4–7.1 (m, ArH, 3H), 4.76 (m, CH₂O, 2H), 3.4 (m, CH₂O, 2H), 2.0 (m, 4H), 1.7 (m, 1H), 1.09 (m, t-Bu, 9H), 0.95 (m, (CH₃)₂, 6H) |
| 47 | 7.4–7.0 (m, ArH, 4H), 4.4 (m, CH, 1H), 3.4 (m, CH₂O, 2H), 2.85 (m, 2H), 2.2–1.6 (m, 8H), 1.28 (d, CH₃, 3H), 1.12 (m, t-Bu, 9H), (isomers) |
| 48 | 7.2–6.8 (m, ArH, 4H), 4.4 (m, CH, 1H), 4.2 (m, CH₂O, 2H), 3.4 (m, 2H), 2.0 (m, 4H), 1.6 (m, 1H), 1.25 (m, 4H), 1.12 (m, t-Bu, 9H), (isomers) |
| 49 | 7.2–7.0 (m, ArH, 4H), 4.4 (m, CH, 1H), 4.0–3.0 (m, 3H), 2.8 (m, 1H), 2.4 (m, 1H), 2.2–1.5 (m, 5H), 1.4–1.2 (m, 4H), 1.0 (m, t-Bu, 9H), (isomers) |
| 51 | 7.4–7.23 (m, ArH, 4H), 5.0 (m, CH, 1H), 3.45 (m, CH₂O, 2H), 3.0 (m, 1H), 2.8 (m, 1H), 2.3 (m, 1H), 2.0 (m, 4H), 1.63 (m, 1H), 1.24 (m, CH₃, 3H), 1.12 (d, t-Bu, 9H), ["R" isomers] |
| 52 | 7.4–7.23 (m, ArH, 4H), 5.0 (m, CH, 1H), 3.46 (m, CH₂O, 2H), 3.0 (m, 1H), 2.8 (m, 1H), 2.3 (m, 1H), 2.0 (m, 4H), 1.63 (m, 1H), 1.2 (m, CH₃, 3H), 1.12 (m, t-Bu, 9H), ["S" isomers] |
| 53 | 7.7–6.9 (m, ArH, 7H), 4.7 (s, CH₂O, 2H), 3.5 (m, CH₂O, 2H), 2.5–1.7 (m, 4H), 1.29 (s, CH₃, 3H) |
| 54 | 7.6–7.0 (m, ArH, 9H), 4.62 (s, CH₂O, 2H), 3.5 (m, CH₂O, 2H), 2.6 (m, 2H), 2.1–1.9 (m, 4H), 1.0 (m, CH₃, 3H) |
| 55 | 7.6–6.9 (m, ArH, 7H), 4.4 (m, CH₂O, 2H), 3.5 (m, CH₂O, 2H), 2.5–1.8 (m, 4H), 1.29 (s, CH₃, 3H) |
| 56 | 7.8–6.9 (m, ArH, 7H), 4.6 (s, CH₂O, 2H), 3.5 (m, CH₂O, 2H), 2.4–1.8 (m, 4H), 1.3 (s, CH₃, 3H) |
| 57 | 7.7–7.0 (m, ArH, 8H), 4.71 (m, CH₂O, 2H), 3.51 (s, CH₂O, 2H), 2.5 (m, 2H), 2.2–1.6 (m, 4H), 0.926 (t, CH₃, 3H) |
| 58 | 8.0–6.8 (m, ArH, 7H), 4.62 (m, CH₂O, 2H), 3.55–3.3 (m, CH₂O, 2H), 2.88 (m, 2H), 2.28 (m, 2H), 2.0 (m, 1H), 1.57 (m, 2H), 1.37 (s, CH₃, 3H), (isomer B) |
| 59 | 8.0–6.9 (m, ArH, 7H), 4.73 (m, CH₂O, 2H), 3.57 (m, CH₂O, 2H), 2.9 (m, 2H), 2.5 (m, 1H), 2.1–1.6 (m, 4H), 1.2 (s, CH₃, 3H), (isomer A) |
| 60 | 8.1–6.9 (m, ArH, 7H), 4.63 (m, CH₂O, 2H), 3.55–3.3 (m, CH₂O, 2H), 2.86 (m, 2H), 2.23 (m, 2H), 2.0 (m, 1H), 1.57 (m, 2H), 1.37 (s, CH₃, 3H), (isomer B) |
| 61 | 5.9 (s, ArH, 1H), 4.6 (s, CH₂O, 2H), 3.94 (s, OCH₃, 6H), 3.6 (m, CH₂O, 2H), 2.2–1.7 (m, 4H), 1.28 (s, CH₃, 3H), 1.13 (s, t-Bu, 9H) |

-continued

NMR DATA FOR BIOLOGICAL TABLE
COMPOUNDS AT 200 MHz IN CDCl₃

| CMPD. | |
|---|---|
| 62 | 8.0–6.9 (m, ArH, 7H), 4.6 (m, CH₂O, 2H), 3.47 (m, CH₂O, 2H), 2.8 (m, 2H), 2.4–1.7 (m, 4H), 1.6 (m, 3H), 0.936 (m, 3H), (isomer A) |
| 63 | 7.29–6.8 (m, ArH, 8H), 4.65 (m, CH₂O, 2H), 3.4 (m, CH₂O, 2H), 1.47 (d, 2CH₃, 6H), 2–1.45 (m, 4H), 1.21 (s, CH₃, 3H) |
| 64 | 7.2–6.8 (m, ArH, 3H), 4.69 (m, CH₂O, 2H), 3.46 (m, CH₂O, 2H), 2.4–1.9 (m, 4H), 1.8–1.2 (m, 3H), 1.28 (s, CH₃, 3H), 1.21 (d, 2CH₃, 6H), (isomer A) |
| 65 | 7.23–6.8 (m, ArH, 3H), 4.6 (q, CH₂O, 2H), 3.3–3.1 (m, CH₂O, 2H), 2.4–1.9 (m, 4H), 1.8–1.3 (m, 3H), 1.28 (s, CH₃, 3H), 1.16 (d, 2CH₃, 6H) |
| 66 | 7.3–6.8 (m, ArH, 8H), 4.62 (m, CH₂O, 2H), 3.6 (m, CH, 1H), 3.37 (m, CH₂O, 2H), 1.82 (m, 3H), 1.44 (m, 4H), 1.19 (d, 3H) |

TEST A

Seeds of barley (*Hordeum vulgare*), barnyardgrass (*Echinochloa crus-galli*), bedstraw (*Galium aparine*), blackgrass (*Alopecurus myosuroides*), cheatgrass (*Bromus secalinus*), chickweed (*Stellaria media*), cocklebur (*Xanthium pensylvanicum*), corn (*Zea mays*), cotton (*Gossypium hirsutum*), crabgrass (*Digitaria* spp.), giant foxtail (*Setaria faberii*), lambsquarters (*Chenopodium album*), morningglory (*Ipomoea hederacea*), rape (*Brassica napus*), rice (*Oryza sativa*), sorghum (*Sorghum bicolor*), soybean (*Glycine max*), sugar beet (*Beta vulgaris*), velvetleaf (*Abutilon theophrasti*), wheat (*Triticum aestiyum*), wild buckwheat (*Polygonum convolvulus*), and wild oat (*Avena fatua*) and purple nutsedge (*Cyperus rotundus*) tubers were planted and treated preemergence with test chemicals dissolved in a non-phytotoxic solvent. At the same time, these crop and weed species were also treated with postemergence applications of test chemicals. Plants ranged in height from two to eighteen cm (one to four leaf stage) for postemergence treatments. Treated plants and controls were maintained in a greenhouse for twelve to sixteen days, after which all species were compared to controls ad visually evaluated. Plant response ratings, summarized in Table A, are based on a scale of 0 to 10 where 0 is no effect and 10 is complete control. A dash (–) response means no test result.

TABLE A

POSTEMERGENCE

| | Rate (1000 g/ha) | | Rate (400 g/ha) | | | | | | | | | | Rate (200 g/ha) | | | | | | | | | | | | |
|---|---|---|---|---|---|---|---|---|---|---|---|---|---|---|---|---|---|---|---|---|---|---|---|---|---|
| COMPOUND | 2 | 3 | 1 | 4 | 5 | 6 | 19 | 20 | 21 | 22 | 23 | 24 | 2 | 3 | 7 | 8 | 9 | 10 | 11 | 12 | 13 | 14 | 15 | 16 |
| Barley | 0 | 0 | 0 | 0 | 0 | 0 | 0 | 0 | 0 | 0 | 0 | 0 | 0 | 0 | 0 | 0 | 0 | 0 | 2 | 0 | 0 | 0 | 0 | 0 |
| Barnyardgrass | 9 | 0 | 0 | 7 | 8 | 9 | 9 | 7 | 0 | 0 | 0 | 2 | 1 | 0 | 9 | 7 | 6 | 7 | 3 | 2 | 2 | 0 | 2 | 8 |
| Bedstraw | 7 | 1 | 0 | 0 | 0 | 0 | 3 | 0 | 3 | 5 | 0 | 2 | 0 | 0 | 0 | 0 | 0 | 4 | 7 | 3 | 0 | 0 | 0 | 2 |
| Blackgrass | 5 | 1 | 0 | 3 | 3 | 7 | 2 | 0 | 3 | 2 | 0 | 3 | 0 | 0 | 5 | 0 | 0 | 0 | 0 | 0 | 0 | 0 | 0 | 0 |
| Cheatgrass | 0 | 0 | 3 | 0 | 0 | 1 | 0 | 0 | 0 | 2 | 0 | 0 | 0 | 0 | 2 | 0 | 2 | 0 | 0 | 0 | 0 | 0 | 0 | 0 |
| Chickweed | 8 | 1 | 0 | 0 | 2 | 0 | 2 | 0 | 0 | 2 | 2 | 0 | 0 | 0 | 0 | 2 | 0 | 8 | 8 | 0 | — | — | 0 | — |
| Cocklebur | 1 | 1 | 1 | — | — | — | — | — | 0 | — | — | — | 1 | 1 | 2 | 1 | 6 | 7 | 8 | 3 | — | 0 | — | — |
| Corn | 0 | 0 | 0 | 0 | 0 | 3 | 0 | 0 | 0 | 0 | 0 | 0 | 0 | 0 | 1 | 0 | 0 | 0 | 0 | 0 | 0 | 0 | 0 | 0 |
| Cotton | — | 0 | 0 | 0 | 0 | 2 | 10 | 6 | 0 | 0 | 0 | 0 | 0 | 0 | 0 | 8 | 0 | 0 | 0 | 0 | 0 | 0 | 0 | 5 |
| Crabgrass | 2 | 0 | 3 | 1 | 3 | 7 | 2 | 0 | 0 | 0 | 0 | 0 | 0 | 0 | 2 | 1 | 0 | 0 | 0 | 0 | 0 | 0 | 0 | 3 |
| Giant foxtail | 3 | 0 | 0 | 2 | 0 | 3 | 2 | 0 | 0 | 0 | 2 | 0 | 0 | 0 | 0 | 1 | 0 | 0 | 0 | 0 | 0 | 0 | 2 | 2 |
| Lambsquarters | 5 | 3 | 0 | 0 | 0 | 0 | 0 | 0 | — | — | — | 6 | 2 | 3 | 3 | 0 | 0 | 3 | 3 | 0 | 3 | 0 | 0 | 0 |
| Morningglory | 1 | 1 | 0 | 0 | 0 | 0 | 0 | 1 | 0 | 0 | 0 | 0 | 0 | 0 | 0 | 1 | 0 | 0 | 0 | 0 | 1 | 0 | 3 | 0 |
| Nutsedge | 0 | 0 | 0 | — | — | 0 | 0 | — | 0 | 0 | 0 | 0 | 0 | 0 | 0 | 0 | 0 | 8 | 0 | 0 | — | — | 0 | — |
| Rape | 2 | 0 | 3 | 0 | 0 | 0 | 0 | 0 | 2 | 0 | 2 | 2 | 0 | 0 | 2 | 0 | 0 | 0 | 0 | 0 | 0 | 0 | 0 | 0 |
| Rice | 0 | 0 | 0 | 0 | 0 | 8 | 2 | 2 | 0 | 0 | 0 | 0 | 0 | 0 | 0 | 0 | 0 | 0 | 0 | 0 | 0 | 0 | 0 | 0 |
| Sorghum | 1 | 0 | 0 | 0 | 0 | 2 | 0 | 0 | 0 | 0 | 0 | 0 | 0 | 0 | 0 | 0 | 0 | 0 | 0 | 0 | 0 | 0 | 0 | 0 |
| Soybean | 0 | 0 | 0 | 0 | 0 | 1 | 5 | 0 | 0 | 0 | 0 | 0 | 0 | 0 | 3 | 1 | 0 | 0 | 0 | 3 | 0 | 0 | 0 | 1 |
| Sugar beet | 4 | 0 | 6 | 0 | 3 | 3 | 0 | 0 | 2 | 0 | 2 | 2 | 0 | 0 | 4 | 2 | 1 | 1 | 2 | 1 | 0 | 0 | 0 | 0 |
| Velvetleaf | 3 | 1 | 1 | 0 | 0 | 2 | 6 | 4 | 0 | 0 | 0 | 0 | 1 | 0 | 3 | 0 | 0 | 5 | 0 | 0 | 0 | 0 | 4 | 3 |
| Wheat | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Wild buckwheat | 5 | 1 | 0 | 0 | 2 | 0 | 1 | 0 | 0 | 4 | 3 | 3 | 0 | 0 | 0 | 3 | 5 | 2 | 7 | 0 | 0 | 0 | 0 | 0 |
| Wild oat | 0 | 0 | 0 | 0 | 0 | 0 | 0 | 0 | 0 | 2 | 3 | 0 | 0 | 0 | 0 | 0 | 0 | 0 | 0 | 0 | 0 | 0 | 0 | 0 |

| | Rate (200 g/ha) | | | | | | | | | | | | | | | | | | | | | | | |
|---|---|---|---|---|---|---|---|---|---|---|---|---|---|---|---|---|---|---|---|---|---|---|---|---|
| COMPOUND | 17 | 18 | 25 | 26 | 9 | 30 | 31 | 32 | 33 | 34 | 35 | 36 | 37 | 38 | 39 | 40 | 41 | 42 | 43 | 44 | 45 | 46 | 47 | 48 | 49 |
| Barley | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 1 | 0 |
| Barnyardgrass | 1 | 4 | 1 | 6 | 0 | 0 | 0 | 0 | 1 | 2 | 0 | 0 | 0 | 0 | 0 | 2 | 1 | 7 | 7 | 0 | 0 | 0 | 0 | 0 | 0 |
| Bedstraw | 0 | 2 | 0 | 0 | 0 | 0 | 0 | 0 | 0 | 0 | 0 | 4 | 0 | 0 | 0 | 0 | 0 | 0 | 0 | 0 | 0 | 0 | 0 | 0 | 0 |
| Blackgrass | 1 | 0 | 0 | 3 | 0 | 0 | 0 | 0 | 0 | 0 | 0 | 0 | 0 | 0 | 0 | 2 | 0 | 0 | 0 | 0 | 0 | 0 | 0 | 3 | 0 |
| Cheatgrass | 0 | 0 | 0 | 2 | 0 | 0 | 0 | 0 | 0 | 0 | 0 | 0 | 0 | 0 | 0 | 2 | — | 0 | 0 | 0 | 0 | 0 | 0 | 0 | 0 |
| Chickweed | — | — | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Cocklebur | — | 7 | 2 | 1 | 1 | 0 | 0 | 2 | 0 | 5 | 0 | — | — | 0 | 2 | 2 | 1 | 1 | 0 | 0 | 0 | 1 | 4 | 2 | |
| Corn | 0 | 0 | 0 | 0 | 0 | 1 | 0 | 0 | 0 | 1 | 0 | 0 | 0 | 0 | 0 | 3 | 0 | 0 | 0 | 0 | 0 | 0 | 0 | 0 | 0 |
| Cotton | 5 | 2 | 0 | 0 | 2 | 2 | 2 | 0 | 0 | 2 | 0 | 0 | 0 | 0 | 2 | 0 | 0 | 1 | 0 | 0 | 0 | 0 | 0 | 0 | 0 |
| Crabgrass | 0 | 0 | 3 | 3 | 2 | 0 | 0 | 3 | 0 | 7 | 0 | 0 | 0 | 0 | 0 | 3 | 2 | 2 | 0 | 0 | 0 | 0 | 3 | 0 | |
| Giant foxtail | 0 | 0 | 1 | 1 | 3 | 0 | 0 | 0 | 1 | 2 | 0 | 0 | 0 | 0 | 0 | 0 | 0 | 0 | 0 | 0 | 0 | 0 | 0 | 0 | 0 |
| Lambsquarters | 0 | 2 | 0 | 0 | 2 | 0 | 5 | 0 | 0 | 0 | — | 5 | 0 | 0 | 0 | 0 | 0 | 0 | 0 | 0 | 0 | 0 | 0 | 0 | 0 |
| Morningglory | 0 | 0 | 0 | 0 | 4 | 0 | 0 | 0 | 0 | 4 | 0 | 0 | 0 | 0 | 0 | 2 | 0 | 0 | 0 | 0 | 0 | 0 | 0 | 0 | 0 |
| Nutsedge | — | — | 7 | 4 | 0 | — | 0 | 0 | 9 | 0 | 0 | 0 | 0 | 0 | 0 | 0 | 0 | 0 | 0 | 0 | 0 | 0 | 0 | 0 | 0 |

TABLE A-continued

| | | | | | | | | | | | | | | | | | | | | | | | | | |
|---|---|---|---|---|---|---|---|---|---|---|---|---|---|---|---|---|---|---|---|---|---|---|---|---|---|
| Rape | 0 | 0 | 0 | 0 | 3 | 0 | 2 | 0 | 0 | 0 | 0 | 0 | 0 | 0 | 0 | 0 | 0 | 0 | 0 | 0 | 0 | 0 | 0 | 0 | 0 |
| Rice | 0 | 0 | 2 | 5 | 0 | 0 | 0 | 2 | 2 | 3 | 0 | 0 | 0 | 0 | 0 | 0 | 0 | 0 | 0 | 0 | 0 | 0 | 0 | 0 | 0 |
| Sorghum | 2 | 0 | 0 | 0 | 0 | 0 | 0 | 2 | 0 | 0 | 0 | 0 | 0 | 0 | 0 | 0 | 0 | 2 | 0 | 0 | 0 | 0 | 0 | 0 | 0 |
| Soybean | 0 | 0 | 2 | 0 | 0 | 3 | 0 | 1 | 0 | 6 | 0 | 0 | 0 | 0 | 0 | 1 | 0 | 2 | 0 | 0 | 0 | 0 | 0 | 0 | 0 |
| Sugar beet | 0 | 0 | 0 | 0 | 2 | 0 | 3 | 0 | 0 | 0 | 0 | 0 | 0 | 0 | 0 | 0 | 0 | 0 | 0 | 0 | 0 | 0 | 0 | 2 | 0 |
| Velvetleaf | 3 | 3 | 2 | 0 | 0 | 0 | 0 | 1 | 7 | 0 | 4 | 0 | 0 | 0 | 0 | 0 | 0 | 5 | 1 | 0 | 0 | 0 | 0 | 0 | 0 |
| Wheat | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 2 | 0 |
| Wild buckwheat | 1 | 0 | — | — | — | — | — | — | — | — | 0 | — | 7 | 0 | 0 | 0 | — | — | — | 0 | 0 | 0 | 0 | 0 | 0 |
| Wild oat | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |

| | Rate (200 g/ha) | | | | | | | | | | | | | | | | Rate (100 g/ha) | | | | | | | | |
|---|---|---|---|---|---|---|---|---|---|---|---|---|---|---|---|---|---|---|---|---|---|---|---|---|---|
| COMPOUND | 51 | 52 | 53 | 54 | 55 | 56 | 57 | 58 | 59 | 60 | 61 | 62 | 63 | 64 | 65 | 66 | 1 | 4 | 5 | 6 | 19 | 20 | 21 | 22 | 23 | 24 |
| Barley | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Barnyardgrass | 1 | 0 | 0 | 2 | 2 | 0 | 0 | 9 | 3 | 6 | 0 | 7 | 2 | 0 | 4 | 2 | 0 | 3 | 0 | 0 | 9 | 0 | 0 | 0 | 0 | 0 |
| Bedstraw | 0 | 0 | 0 | 0 | 0 | 0 | 0 | 0 | 0 | 0 | 0 | 0 | 0 | 0 | 0 | — | 0 | 0 | 0 | 0 | 0 | 0 | 0 | 2 | 0 | 0 |
| Blackgrass | 3 | 0 | 0 | 0 | 0 | 0 | 0 | 0 | 2 | 0 | 0 | 0 | 0 | 2 | 0 | 0 | 0 | 0 | 0 | 5 | 0 | 0 | 3 | 2 | 3 | 2 |
| Cheatgrass | 0 | 0 | 0 | 0 | 0 | 0 | 0 | 0 | 0 | 0 | 0 | 0 | 0 | 0 | 0 | 0 | 2 | 0 | 0 | 0 | 0 | 0 | 0 | 0 | 2 | 0 |
| Chickweed | 0 | 0 | 0 | 0 | 0 | 0 | 0 | 0 | 0 | 0 | 1 | 0 | 0 | 0 | 0 | — | 0 | 0 | 0 | 0 | 0 | 0 | 0 | 0 | 0 | 0 |
| Cocklebur | 1 | 0 | 1 | 1 | 1 | 0 | 0 | 2 | 1 | 0 | 0 | 1 | 2 | 2 | 0 | 1 | 1 | — | — | — | — | — | — | — | — | — |
| Corn | 0 | 0 | 1 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Cotton | 0 | 0 | 0 | 2 | 2 | 0 | 0 | 3 | 0 | 2 | 0 | 0 | 3 | 0 | 0 | 0 | 0 | 0 | 0 | 0 | 7 | 0 | 0 | 0 | 0 | 0 |
| Crabgrass | 0 | 0 | 0 | 0 | 0 | 0 | 0 | 3 | 0 | 1 | 0 | 0 | 0 | 3 | 0 | 0 | 0 | 0 | 0 | 0 | 0 | 0 | 0 | 0 | 0 | 0 |
| Giant foxtail | 0 | 0 | 0 | 0 | 0 | 0 | 0 | 0 | 0 | 0 | 0 | 0 | 0 | 0 | 0 | 0 | 0 | 0 | 1 | 7 | 2 | 0 | 0 | 0 | 0 | 0 |
| Lambsquarters | 0 | 0 | 0 | 0 | 0 | 0 | 3 | 3 | 4 | — | 0 | 6 | 0 | — | 0 | 0 | 0 | 0 | — | 0 | 0 | 5 | — | 2 | 2 |  |
| Morningglory | 0 | 0 | 0 | 0 | 0 | 2 | 0 | 0 | 0 | 0 | 0 | 0 | 0 | 0 | 0 | 2 | 0 | 0 | 0 | 0 | 0 | 0 | 0 | 0 | 0 | 0 |
| Nutsedge | — | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Rape | 0 | 0 | 0 | 1 | 2 | 0 | 0 | 0 | 2 | 0 | 0 | 2 | 0 | 0 | 0 | 0 | 0 | 0 | 0 | 0 | 0 | 0 | 0 | 0 | 2 | 0 |
| Rice | 0 | 0 | 0 | 2 | 2 | 0 | 0 | 0 | 0 | 0 | 0 | 0 | 2 | 0 | 0 | 0 | 0 | 0 | 0 | 0 | 0 | 0 | 0 | 0 | 0 | 0 |
| Sorghum | 0 | 0 | 0 | 0 | 0 | 0 | 0 | 1 | 0 | 0 | 0 | 0 | 0 | 0 | 0 | 0 | 0 | 0 | 0 | 0 | 0 | 0 | 0 | 0 | 0 | 0 |
| Soybean | 0 | 0 | 0 | 1 | 3 | 0 | 0 | 1 | 0 | 0 | 0 | 0 | 1 | 0 | 1 | 2 | 0 | 0 | 0 | 0 | 2 | 0 | 0 | 0 | 0 | 0 |
| Sugar beet | 0 | 0 | 0 | 0 | 0 | 0 | 3 | 3 | 3 | 0 | 0 | 3 | 3 | 0 | 0 | 0 | 3 | 0 | 0 | 0 | 0 | 0 | 0 | 0 | 2 | 0 |
| Velvetleaf | 0 | 0 | 2 | 6 | 0 | 0 | 0 | 3 | 1 | 2 | 0 | 0 | 2 | 0 | 0 | 2 | 1 | 0 | 0 | 1 | 5 | 3 | 0 | 0 | 0 | 0 |
| Wheat | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Wild buckwheat | 0 | 0 | — | — | — | — | 0 | 0 | 9 | 0 | 2 | — | — | — | — | 0 | 0 | 0 | 0 | 0 | 0 | 0 | 0 | 0 | 2 | 0 |
| Wild oat | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |

| | Rate (50 g/ha) | | | | | | | | | | | | | | | | | | | | | | | | |
|---|---|---|---|---|---|---|---|---|---|---|---|---|---|---|---|---|---|---|---|---|---|---|---|---|---|
| COMPOUND | 7 | 8 | 9 | 10 | 11 | 12 | 13 | 14 | 15 | 16 | 17 | 18 | 25 | 26 | 29 | 30 | 31 | 32 | 33 | 34 | 35 | 36 | 37 | 38 | 39 | 40 | 41 |
| Barley | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Barnyardgrass | 4 | 2 | 1 | 0 | 0 | 0 | 0 | 0 | 0 | 0 | 0 | 2 | 0 | 1 | 0 | 0 | 0 | 0 | 0 | 0 | 0 | 0 | 0 | 0 | 0 | 0 |
| Bedstraw | 0 | 0 | 0 | 2 | 0 | 0 | 0 | 0 | 0 | 1 | 0 | 0 | 0 | 0 | 0 | 0 | 0 | 0 | 0 | 0 | 0 | 0 | 0 | 0 | 0 | 0 |
| Blackgrass | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Cheatgrass | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Chickweed | 0 | 0 | 0 | 3 | 2 | 0 | — | — | — | — | 0 | — | 0 | 0 | 0 | 0 | 0 | 0 | 0 | 0 | 0 | 0 | 0 | 0 | 0 | 0 |
| Cocklebur | 2 | 1 | 0 | 2 | 5 | 1 | — | — | — | 0 | — | 5 | 1 | 1 | 1 | 0 | 0 | 0 | 0 | 3 | 0 | — | — | 0 | 0 | 0 |
| Corn | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Cotton | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Crabgrass | 0 | 0 | 0 | 0 | 0 | 0 | 0 | 0 | 0 | 0 | 0 | 0 | 1 | 0 | 0 | 0 | 0 | 0 | 2 | 0 | 0 | 0 | 0 | 0 | 0 | 0 |
| Giant foxtail | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Lambsquarters | 0 | 0 | 0 | 0 | 0 | 0 | 0 | 0 | 0 | 0 | 0 | 0 | 0 | 0 | 0 | 0 | 0 | — | 0 | 0 | 4 | 0 | 0 | 0 | 0 | 0 |
| Morningglory | 0 | 0 | 0 | 0 | 0 | 0 | 0 | 0 | 0 | 0 | 0 | 0 | 0 | 2 | 0 | 0 | 0 | 0 | 0 | 0 | 0 | 0 | 0 | 0 | 0 | 0 |
| Nutsedge | — | 0 | 0 | 0 | 0 | 0 | 0 | 0 | — | — | 7 | 4 | 0 | 0 | 0 | 0 | 0 | — | 0 | 0 | 0 | 0 | 0 | 0 | 0 | 0 |
| Rape | 0 | 0 | 0 | 2 | 2 | 0 | 0 | 0 | 0 | 0 | 0 | 0 | 0 | 2 | 0 | 0 | 0 | 0 | 0 | 0 | 0 | 0 | 0 | 0 | 0 | 0 |
| Rice | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Sorghum | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Soybean | 0 | 0 | 0 | 0 | 0 | 1 | 0 | 0 | 0 | 0 | 0 | 0 | 0 | 0 | 0 | 0 | 0 | 0 | 0 | 0 | 0 | 0 | 0 | 0 | 0 | 0 |
| Sugar beet | 0 | 0 | 0 | 1 | 3 | 0 | 0 | 0 | 0 | 0 | 0 | 0 | 0 | 0 | 0 | 0 | 0 | 0 | 0 | 0 | 0 | 0 | 0 | 0 | 0 | 0 |
| Velvetleaf | 3 | 0 | 0 | 3 | 0 | 0 | 0 | 0 | 2 | 0 | 0 | 2 | 0 | 0 | 0 | 0 | 0 | 0 | — | 0 | 0 | 0 | 0 | 0 | 0 | 0 |
| Wheat | 0 | 0 | 0 | 0 | 2 | 0 | 0 | 0 | 0 | 0 | 0 | 0 | 0 | 0 | 0 | 0 | 0 | 0 | 0 | 0 | 0 | 0 | 0 | 0 | 0 | 0 |
| Wild buckwheat | 0 | 0 | 0 | 3 | 2 | 0 | 0 | 0 | 0 | 0 | 0 | — | — | — | — | — | — | — | — | 0 | — | 3 | 0 | 0 | 0 | — |
| Wild oat | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |

| | Rate (50 g/ha) | | | | | | | | | | | | | | | | | | | | | | | |
|---|---|---|---|---|---|---|---|---|---|---|---|---|---|---|---|---|---|---|---|---|---|---|---|---|
| COMPOUND | 42 | 43 | 44 | 45 | 46 | 47 | 48 | 49 | 51 | 52 | 53 | 54 | 55 | 56 | 57 | 58 | 59 | 60 | 61 | 62 | 63 | 64 | 65 | 66 |
| Barley | 0 | 0 | 0 | 0 | 0 | 0 | 0 | 0 | 0 | 0 | 0 | 0 | 0 | 0 | 0 | 0 | 0 | 0 | — | 0 | 0 | 0 | 0 | 0 |
| Barnyardgrass | 0 | 0 | 0 | 0 | 0 | 0 | 0 | 0 | 0 | 0 | 0 | 0 | 0 | 0 | 0 | 1 | 0 | 0 | 0 | 0 | 0 | 0 | 0 | 0 |
| Bedstraw | 0 | 0 | 0 | 0 | 0 | 0 | 0 | 0 | 0 | 0 | 0 | 0 | 0 | 0 | 0 | 0 | 0 | 0 | — | 0 | 0 | 0 | 0 | 0 |
| Blackgrass | 0 | 0 | 0 | 0 | 0 | 0 | 0 | 0 | 2 | 0 | 0 | 0 | 0 | 0 | 0 | 0 | 0 | 0 | — | 0 | 0 | 0 | 0 | 0 |
| Cheatgrass | 0 | 0 | 0 | 0 | 0 | 0 | 0 | 0 | 0 | 0 | 0 | 0 | 0 | 0 | 0 | 0 | 0 | 0 | — | 0 | 0 | 0 | 0 | 0 |
| Chickweed | 0 | 0 | 0 | 0 | 0 | 0 | 0 | 0 | 0 | 0 | — | 0 | 0 | 0 | 0 | 0 | 0 | 0 | — | 0 | 0 | 0 | 0 | 0 |
| Cocklebur | 0 | 0 | 0 | 0 | 0 | 0 | 0 | 0 | 0 | 0 | 1 | 1 | 0 | 0 | 0 | 2 | 0 | — | 0 | 1 | 1 | 1 | 0 | 1 |
| Corn | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Cotton | 0 | 0 | 0 | 0 | 0 | 0 | 0 | 0 | 0 | 0 | 0 | 2 | 1 | 0 | 0 | 0 | 0 | 0 | 0 | 0 | 0 | 0 | 0 | 0 |

TABLE A-continued

| | | | | | | | | | | | | | | | | | | | | | | | | |
|---|---|---|---|---|---|---|---|---|---|---|---|---|---|---|---|---|---|---|---|---|---|---|---|---|
| Crabgrass | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Giant foxtail | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Lambsquarters | 0 | 0 | 0 | 0 | 0 | 0 | 0 | 0 | 0 | 0 | 0 | 0 | 0 | 0 | 0 | 0 | 0 | 0 | 0 | — | 0 | 0 | 0 | 0 |
| Morningglory | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Nutsedge | 0 | 0 | 0 | 0 | 0 | 0 | 0 | 0 | 0 | — | 0 | 0 | — | 0 | 0 | 0 | 0 | 0 | 0 | 0 | — | 0 | 0 | 0 |
| Rape | 0 | 0 | 0 | 0 | 0 | 0 | 0 | 0 | 0 | 0 | 0 | 0 | 0 | 0 | 0 | 0 | 0 | 0 | 0 | — | 0 | 0 | 0 | 0 |
| Rice | 0 | 0 | 0 | 0 | 0 | 0 | 0 | 0 | 0 | 0 | 0 | 0 | 2 | 0 | 0 | 0 | 0 | 0 | 0 | 0 | 0 | 0 | 0 | 0 |
| Sorghum | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Soybean | 0 | 0 | 0 | 0 | 0 | 0 | 0 | 0 | 0 | 0 | 0 | 0 | 2 | 0 | 0 | 0 | 0 | 0 | 0 | 0 | 0 | 0 | 0 | 2 |
| Sugar beet | 0 | 0 | 0 | 0 | 0 | 0 | 0 | 0 | 0 | 0 | 0 | 0 | 0 | 0 | 0 | 0 | 0 | 0 | 0 | — | 0 | 0 | 0 | 0 |
| Velvetleaf | 0 | 0 | 0 | 0 | 0 | 0 | 0 | 0 | 0 | 0 | 0 | 2 | 0 | 0 | 0 | 0 | 0 | 0 | 0 | 0 | 0 | 0 | 0 | 0 |
| Wheat | 0 | 0 | 0 | 0 | 0 | 0 | 0 | 0 | 0 | 0 | 0 | 0 | 0 | 0 | 0 | 0 | 0 | 0 | 0 | — | 0 | 0 | 0 | 0 |
| Wild buckwheat | — | — | 0 | 0 | 0 | 0 | 0 | 0 | 0 | 0 | — | — | — | — | — | — | — | 0 | 0 | — | — | — | — | 0 |
| Wild oat | 0 | 0 | 0 | 0 | 0 | 0 | 0 | 0 | 0 | 0 | 0 | 0 | 0 | 0 | 0 | 0 | 0 | 0 | 0 | — | 0 | 0 | 0 | 0 |

PREEMERGENCE

| | Rate (1000 g/ha) | | Rate (400 g/ha) | | | | | | | | | | Rate (200 g/ha) | | | | | | | | |
|---|---|---|---|---|---|---|---|---|---|---|---|---|---|---|---|---|---|---|---|---|---|---|
| COMPOUND | 2 | 3 | 1 | 4 | 5 | 6 | 19 | 20 | 21 | 22 | 23 | 24 | 2 | 3 | 7 | 8 | 9 | 10 | 11 | 12 | 13 |
| Barley | 0 | 0 | 0 | 0 | 0 | 0 | 0 | 0 | 0 | 0 | 0 | 0 | 0 | 0 | 0 | 2 | 0 | 0 | 0 | 0 | 2 |
| Barnyardgrass | 10 | 9 | 9 | 10 | 10 | 10 | 10 | 0 | 8 | 9 | 9 | 7 | 2 | 3 | 10 | 10 | 10 | 10 | 10 | 9 | 9 |
| Bedstraw | 4 | 4 | 0 | 0 | 2 | 4 | 2 | 0 | 0 | 0 | 0 | 0 | 2 | 0 | 0 | 4 | 0 | 2 | 2 | 2 | 0 |
| Blackgrass | 6 | 3 | 3 | 10 | 10 | 10 | 9 | 2 | 1 | 0 | 3 | 3 | 0 | 0 | 9 | 9 | 8 | 9 | 7 | 7 | 7 |
| Cheatgrass | 2 | 2 | 2 | 7 | 3 | 7 | 2 | 0 | 2 | 0 | 0 | 2 | 0 | 0 | 9 | 3 | 5 | 6 | 2 | 10 | 2 |
| Chickweed | 5 | 0 | 4 | 2 | 0 | 5 | 3 | 3 | 2 | 2 | 0 | 2 | 0 | 0 | 3 | 2 | 0 | 2 | 0 | 6 | 0 |
| Cocklebur | 0 | 0 | 0 | — | — | — | 0 | — | — | — | — | — | 0 | 0 | 9 | 0 | 7 | 5 | 0 | 0 | 0 |
| Corn | 2 | 0 | 7 | 2 | 4 | 10 | 0 | 0 | 1 | 0 | 3 | 2 | 0 | 0 | 8 | 9 | 2 | 8 | 2 | 2 | 0 |
| Cotton | 0 | 0 | 0 | 0 | 0 | 0 | 0 | 0 | 0 | 0 | 0 | 3 | 0 | 0 | 8 | 2 | 0 | 0 | 0 | 0 | 0 |
| Crabgrass | 9 | 7 | 2 | 10 | 8 | 10 | 9 | 5 | 4 | 1 | 9 | 5 | 9 | 1 | 10 | 10 | 10 | 9 | 6 | 6 | 10 |
| Giant foxtail | 9 | 7 | 6 | 6 | 2 | 6 | 9 | 6 | 2 | 2 | 6 | 6 | 7 | 0 | 10 | 10 | 2 | 6 | 2 | 3 | 3 |
| Lambsquarters | 7 | 6 | 5 | 0 | 0 | 5 | 3 | 0 | — | 0 | 0 | — | 0 | 0 | 3 | 5 | 0 | 5 | 8 | 0 | 0 |
| Morningglory | 0 | 0 | 0 | 0 | 0 | 0 | 0 | 2 | 0 | 1 | 0 | 0 | 0 | 0 | 0 | 2 | 0 | 0 | 0 | 0 | 0 |
| Nutsedge | 0 | 0 | 0 | 0 | 0 | 0 | 0 | 2 | — | — | 0 | — | 0 | 0 | 10 | 10 | 0 | 10 | 9 | 0 | — |
| Rape | 6 | 0 | 0 | 0 | 0 | 0 | 3 | 0 | 0 | 0 | 0 | 0 | 0 | 0 | 0 | 0 | 0 | 0 | 0 | 0 | 0 |
| Rice | 0 | 0 | 0 | 2 | 0 | 0 | 0 | 0 | 0 | 0 | 0 | 0 | 0 | 0 | 1 | 1 | 0 | 0 | 0 | 0 | 2 |
| Sorghum | 2 | 0 | 0 | 4 | 2 | 9 | 0 | 0 | 0 | 0 | 0 | 2 | 0 | 0 | 7 | 2 | 4 | 3 | 1 | 0 | 0 |
| Soybean | 0 | 0 | 0 | 0 | 0 | 3 | 0 | 0 | 0 | 0 | 2 | 3 | 0 | 0 | 1 | 2 | 0 | 0 | 1 | 0 | 2 |
| Sugar beet | 0 | 3 | 2 | 1 | 0 | 1 | 2 | 0 | 2 | 0 | 0 | 0 | 0 | 0 | 2 | 1 | 1 | 1 | 1 | 0 | 0 |
| Velvetleaf | 6 | 0 | 0 | 1 | 1 | 2 | 6 | 0 | 2 | 0 | 0 | 0 | 0 | 0 | 6 | 3 | 0 | 5 | 6 | 0 | 0 |
| Wheat | 0 | 0 | 0 | 0 | 0 | 1 | 0 | 0 | 0 | 0 | 2 | 0 | 0 | 0 | 1 | 0 | 0 | 2 | 0 | 0 | 0 |
| Wild buckwheat | 3 | 0 | 0 | 0 | 0 | 0 | 0 | 0 | — | — | — | — | 0 | 0 | 4 | 3 | 2 | 0 | 2 | 3 | 0 |
| Wild oat | 0 | 0 | 0 | 4 | 0 | 6 | 3 | 0 | 3 | 0 | 2 | 0 | 0 | 0 | 6 | 6 | 2 | 6 | 0 | 3 | 2 |

| | Rate (200 g/ha) | | | | | | | | | | | | | | | | | | | |
|---|---|---|---|---|---|---|---|---|---|---|---|---|---|---|---|---|---|---|---|---|
| COMPOUND | 14 | 15 | 16 | 17 | 18 | 25 | 26 | 29 | 30 | 31 | 32 | 33 | 34 | 35 | 36 | 37 | 38 | 39 | 40 | 41 | 42 | 43 |
| Barley | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Barnyardgrass | 5 | 10 | 10 | 9 | 10 | 10 | 10 | 9 | 2 | 0 | 0 | 0 | 0 | 0 | 8 | 9 | 8 | 10 | 3 | 10 | 10 | 10 |
| Bedstraw | 0 | 2 | 4 | 2 | 0 | 3 | 2 | 0 | 0 | 7 | 2 | 0 | 0 | 0 | 0 | 0 | 0 | 0 | 0 | 0 | 0 | 0 |
| Blackgrass | 3 | 9 | 9 | 8 | 8 | 4 | 9 | 3 | 0 | 2 | 0 | 0 | 0 | 6 | 2 | 7 | 3 | 0 | 0 | 3 | 2 | 6 |
| Cheatgrass | 2 | 3 | 2 | 5 | 2 | 3 | 7 | 0 | 2 | 0 | 0 | 0 | 0 | 0 | 0 | 0 | 0 | 0 | 0 | 2 | 0 | 0 |
| Chickweed | 0 | 7 | 3 | 0 | 2 | 4 | 4 | 8 | 6 | 3 | 0 | 0 | 0 | 0 | 0 | 2 | 0 | 0 | 2 | 2 | 0 | 0 |
| Cocklebur | — | — | 0 | — | — | 0 | 0 | 0 | 0 | 0 | 0 | 0 | 0 | 0 | — | — | 1 | 0 | 0 | 0 | 0 | 0 |
| Corn | 0 | 0 | 0 | 0 | 0 | 4 | 5 | 0 | 0 | 0 | 0 | 0 | 0 | 0 | 5 | 0 | 0 | 0 | 0 | 3 | 0 | 3 |
| Cotton | 0 | 0 | 2 | 2 | 0 | 0 | 8 | 0 | 0 | 0 | 0 | 0 | 0 | 0 | 0 | 0 | 0 | 0 | 0 | 0 | 0 | 0 |
| Crabgrass | 5 | 7 | 10 | 5 | 10 | 7 | 9 | 7 | 5 | 2 | 2 | 0 | 2 | 4 | 9 | 4 | 7 | 0 | 8 | 9 | 9 | 9 |
| Giant foxtail | 5 | 2 | 7 | 2 | 10 | 7 | 9 | 6 | 5 | 2 | 2 | 0 | 0 | 2 | 5 | 6 | 5 | 4 | 9 | 9 | 9 | 9 |
| Lambsquarters | 0 | 3 | 10 | 0 | 0 | — | 5 | 0 | 10 | 5 | 0 | — | 0 | — | 2 | 2 | 0 | 0 | 0 | 3 | 3 | — |
| Morningglory | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Nutsedge | — | — | 0 | — | 4 | 7 | 0 | 0 | 0 | 0 | 0 | 0 | 0 | 0 | 0 | — | 0 | 0 | 4 | 0 | 0 | 0 |
| Rape | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Rice | 0 | 0 | 0 | 0 | 0 | 2 | 2 | 1 | 0 | 0 | 0 | 0 | 0 | 0 | 0 | 0 | 0 | 0 | 0 | 1 | 0 | 0 |
| Sorghum | 0 | 0 | 4 | 2 | 0 | 0 | 0 | 0 | 0 | 0 | 0 | 0 | 0 | 0 | 0 | 0 | 0 | 0 | 0 | 2 | 2 | 2 |
| Soybean | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Sugar beet | 0 | 2 | 2 | 0 | 0 | 0 | 2 | 0 | 0 | 0 | 0 | 0 | 0 | 0 | 0 | 0 | 0 | 0 | 0 | 0 | 0 | 0 |
| Velvetleaf | 3 | 2 | 3 | 0 | 0 | 0 | 0 | 0 | 1 | 0 | 0 | 0 | 0 | 0 | 1 | 0 | 0 | 0 | 0 | 0 | 3 | 0 |
| Wheat | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Wild buckwheat | 0 | 10 | 1 | 0 | 0 | — | — | — | — | — | — | 0 | 0 | — | 3 | — | 0 | — | 0 | — | — | — |
| Wild oat | 2 | 2 | 3 | 2 | 9 | 2 | 2 | 0 | 0 | 0 | 0 | 0 | 0 | 0 | 0 | 0 | 0 | 0 | 0 | 2 | 0 | 2 |

TABLE A-continued

| | Rate (200 g/ha) | | | | | | | | | | | | | | | | | | | | | | |
|---|---|---|---|---|---|---|---|---|---|---|---|---|---|---|---|---|---|---|---|---|---|---|---|
| COMPOUND | 44 | 45 | 46 | 47 | 48 | 49 | 51 | 52 | 53 | 54 | 55 | 56 | 57 | 58 | 59 | 60 | 61 | 62 | 63 | 64 | 65 | 66 |
| Barley | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Barnyardgrass | 1 | 0 | 0 | 0 | 9 | 0 | 10 | 7 | 2 | 0 | 2 | 0 | 0 | 7 | 4 | 9 | 0 | 9 | 7 | 10 | 10 | 8 |
| Bedstraw | 0 | 0 | 0 | 0 | 0 | 0 | 0 | 0 | 0 | 2 | 0 | 0 | 0 | 0 | 0 | 0 | 0 | 0 | 0 | 0 | 0 | 0 |
| Blackgrass | 0 | 0 | 0 | 0 | 3 | 3 | 3 | 0 | 2 | 0 | 0 | 0 | 0 | 4 | 0 | 2 | 0 | 2 | 4 | 7 | 5 | 0 |
| Cheatgrass | 0 | 0 | 0 | 0 | 1 | 0 | 0 | 0 | 0 | 0 | 0 | 0 | 0 | 0 | 0 | 0 | 2 | 0 | 0 | 0 | 0 | 0 |
| Chickweed | 0 | 0 | 0 | 0 | 0 | 0 | 0 | 0 | 0 | 3 | 6 | 0 | 0 | 0 | 3 | 0 | 9 | 6 | 0 | 5 | 0 | 0 |
| Cocklebur | 0 | 0 | 0 | 0 | 0 | 0 | 0 | 0 | — | 0 | 0 | — | 0 | 0 | 0 | 0 | 0 | 0 | 0 | 0 | 0 | 0 |
| Corn | 3 | 0 | 0 | 0 | 3 | 2 | 2 | 0 | 0 | 0 | 0 | 0 | 0 | 0 | 0 | 0 | 0 | 2 | 0 | 2 | 3 | 1 |
| Cotton | 0 | 0 | 0 | 0 | 0 | 0 | 0 | 0 | 0 | 0 | 0 | 0 | 0 | 0 | 0 | 0 | 0 | 0 | 0 | 0 | 0 | — |
| Crabgrass | 2 | 0 | 0 | 2 | 5 | 0 | 8 | 0 | 3 | 0 | 5 | 0 | 0 | 8 | 5 | 9 | 0 | 8 | 2 | 8 | 7 | 2 |
| Giant foxtail | 1 | 0 | 0 | 0 | 4 | 0 | 4 | 5 | 4 | 0 | 7 | 2 | 0 | 9 | 9 | 9 | 0 | 8 | 8 | 7 | 10 | 7 |
| Lambsquarters | 0 | 0 | — | 0 | 0 | 0 | 2 | 0 | 3 | 0 | 10 | — | — | 5 | 0 | 4 | 5 | 0 | 3 | 5 | — | — |
| Morningglory | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Nutsedge | 0 | 0 | 0 | 0 | 0 | 0 | 0 | 0 | 0 | 0 | 0 | — | 0 | 0 | 0 | 0 | 0 | 0 | 0 | 0 | 0 | 0 |
| Rape | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Rice | 2 | 0 | 0 | 0 | 0 | 0 | 2 | 0 | 0 | 0 | 0 | 1 | 0 | 0 | 0 | 0 | 0 | 0 | 0 | 0 | 0 | 0 |
| Sorghum | 0 | 0 | 0 | 0 | 0 | 0 | 0 | 0 | 0 | 0 | 0 | 0 | 0 | 0 | 0 | 0 | 0 | 0 | 0 | 0 | 2 | 1 |
| Soybean | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Sugar beet | 0 | 0 | 0 | 0 | 0 | 0 | 0 | 0 | 0 | 0 | 0 | 0 | 0 | 3 | 0 | 0 | 0 | 0 | 0 | 1 | 0 | 0 |
| Velvetleaf | 0 | 0 | 0 | 0 | 0 | 0 | 0 | 0 | 0 | 0 | 0 | 0 | 0 | 0 | 0 | 0 | 0 | 0 | 2 | 2 | 1 | 3 |
| Wheat | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Wild buckwheat | — | — | — | 0 | — | 0 | 0 | 0 | 0 | 0 | — | — | 0 | — | — | — | — | — | — | — | 0 | — |
| Wild oat | 0 | 0 | 0 | 0 | 0 | 0 | 0 | 0 | 0 | 0 | 0 | 0 | — | 0 | 0 | 0 | 0 | 0 | 0 | 2 | 5 | 0 |

| | Rate (100 g/ha) | | | | | | | | | | Rate (50 g/ha) | | | | | | | | | | | |
|---|---|---|---|---|---|---|---|---|---|---|---|---|---|---|---|---|---|---|---|---|---|---|
| COMPOUND | 1 | 4 | 5 | 6 | 19 | 20 | 21 | 22 | 23 | 24 | 7 | 8 | 9 | 10 | 11 | 12 | 13 | 14 | 15 | 16 | 17 | 18 |
| Barley | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Barnyardgrass | 0 | 9 | 10 | 10 | 8 | 1 | 4 | 1 | 2 | 1 | 10 | 9 | 10 | 9 | 9 | 7 | 0 | 0 | 6 | 9 | 2 | 6 |
| Bedstraw | 0 | 0 | 0 | 1 | 0 | 0 | 0 | 0 | 0 | 2 | 0 | 1 | 0 | 0 | 8 | 2 | 0 | 0 | 0 | 1 | 0 | 0 |
| Blackgrass | 0 | 9 | 7 | 10 | 2 | 0 | 0 | 0 | 1 | 3 | 8 | 7 | 3 | 3 | 0 | 5 | 0 | 0 | 0 | 3 | 0 | 3 |
| Cheatgrass | 0 | 0 | 0 | 5 | 0 | 0 | 0 | 0 | 0 | 2 | 4 | 3 | 0 | 3 | 2 | 0 | 0 | 0 | 0 | 2 | 0 | 2 |
| Chickweed | 2 | 0 | 0 | 0 | 0 | 0 | 0 | 0 | 0 | 0 | 0 | 2 | 0 | 0 | 0 | 0 | 0 | 0 | 0 | 0 | 0 | 0 |
| Cocklebur | — | — | — | — | — | — | 0 | — | — | — | 0 | 0 | 0 | — | 0 | 0 | — | — | — | — | — | — |
| Corn | 0 | 0 | 0 | 0 | 0 | 0 | 0 | 0 | 0 | 0 | 3 | 2 | 2 | 2 | 1 | 0 | 0 | 0 | 0 | 0 | 0 | 0 |
| Cotton | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Crabgrass | 0 | 6 | 4 | 9 | 7 | 0 | 0 | 0 | 1 | 0 | 9 | 7 | 2 | 7 | 2 | 0 | 2 | 0 | 2 | 5 | 2 | 3 |
| Giant foxtail | 0 | 2 | 0 | 2 | 6 | 0 | 0 | 2 | 2 | 2 | 3 | 3 | 0 | 3 | 2 | 0 | 2 | 2 | 2 | 4 | 2 | 3 |
| Lambsquarters | — | 0 | 0 | 2 | 0 | 0 | 0 | 0 | 0 | 0 | 0 | 0 | 0 | 0 | 5 | 0 | 0 | 0 | 0 | 2 | 0 | 0 |
| Morningglory | 0 | 0 | 0 | 0 | 0 | 0 | 0 | 1 | 0 | 0 | 0 | 2 | 0 | 0 | 0 | 0 | 0 | 0 | 0 | 0 | 0 | 0 |
| Nutsedge | 0 | — | 0 | 0 | 0 | 0 | 0 | 0 | 0 | — | 0 | 0 | 0 | 0 | 0 | 0 | — | — | — | 3 | — | 0 |
| Rape | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Rice | 0 | 0 | 0 | 0 | 0 | 0 | 0 | 0 | 0 | 0 | 0 | 1 | 0 | 0 | 0 | 0 | 0 | 0 | 0 | 0 | 0 | 0 |
| Sorghum | 0 | 0 | 0 | 3 | 0 | 0 | 0 | 0 | 0 | 0 | 2 | 0 | 0 | 0 | 0 | 0 | 0 | 0 | 0 | 0 | 0 | 0 |
| Soybean | 0 | 0 | 0 | 0 | 0 | 0 | 0 | 0 | 0 | 3 | 1 | 0 | 0 | 0 | 0 | 0 | 0 | 0 | 0 | 0 | 0 | 0 |
| Sugar beet | 2 | 0 | 0 | 0 | 0 | 0 | 0 | 0 | 0 | 0 | 1 | 1 | 0 | 0 | 2 | 0 | 0 | 0 | 0 | 0 | 0 | 0 |
| Velvetleaf | 0 | 0 | 0 | 1 | 4 | 0 | 0 | 0 | 0 | 0 | 2 | 0 | 0 | 3 | 0 | 0 | 0 | 0 | 0 | 0 | 0 | 0 |
| Wheat | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Wild buckwheat | 0 | 0 | 0 | 0 | 0 | 0 | — | — | 2 | — | 3 | 2 | 2 | 0 | 2 | 2 | 0 | 0 | 2 | 0 | 0 | 0 |
| Wild oat | 0 | 0 | 0 | 0 | 0 | 0 | 0 | 0 | 0 | 0 | 2 | 0 | 0 | 0 | 0 | 0 | 0 | 0 | 0 | 2 | 0 | 3 |

| | Rate (50 g/ha) | | | | | | | | | | | | | | | | | | | | | | |
|---|---|---|---|---|---|---|---|---|---|---|---|---|---|---|---|---|---|---|---|---|---|---|---|
| COMPOUND | 25 | 26 | 29 | 30 | 31 | 32 | 33 | 34 | 35 | 36 | 37 | 38 | 39 | 40 | 41 | 42 | 43 | 44 | 45 | 46 | 47 | 48 | 49 |
| Barley | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Barnyardgrass | 3 | 9 | 1 | 0 | 0 | 0 | 0 | 0 | 0 | 0 | 6 | 1 | 0 | 0 | 2 | 9 | 8 | 0 | 0 | 0 | 0 | 1 | 0 |
| Bedstraw | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Blackgrass | 0 | 3 | 0 | 0 | 0 | 0 | 0 | 0 | 0 | 0 | 2 | 0 | 0 | 0 | 0 | 0 | 0 | 0 | 0 | 0 | 0 | 0 | 2 |
| Cheatgrass | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Chickweed | 0 | 0 | 0 | 4 | 0 | 0 | 0 | 0 | 0 | 0 | 1 | 0 | 0 | 0 | 0 | 0 | 0 | 0 | 0 | 0 | 0 | 0 | 0 |
| Cocklebur | 0 | 0 | 0 | 0 | 0 | 0 | 0 | 0 | 0 | — | — | 0 | 0 | 0 | 0 | 0 | 0 | 0 | 0 | 0 | 0 | 0 | 0 |
| Corn | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Cotton | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Crabgrass | 3 | 7 | 1 | 1 | 0 | 0 | 0 | 0 | 0 | 0 | 3 | 0 | 0 | 0 | 3 | 6 | 5 | 0 | 0 | 0 | 0 | 0 | 0 |
| Giant foxtail | 6 | 2 | 2 | 1 | 0 | 0 | 0 | 0 | 0 | 0 | 0 | 0 | 0 | 0 | 3 | 5 | 7 | 0 | 0 | 0 | 0 | 0 | 0 |
| Lambsquarters | 0 | 0 | 3 | 0 | 4 | 0 | — | — | — | 0 | 2 | — | 0 | 0 | 0 | 0 | 0 | 0 | 0 | 0 | 0 | 0 | 0 |
| Morningglory | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Nutsedge | 3 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Rape | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Rice | 0 | 2 | 0 | 0 | 0 | 0 | 0 | 0 | 0 | 0 | 0 | 0 | 0 | 0 | 0 | 0 | 0 | 0 | 0 | 0 | 0 | 0 | 0 |
| Sorghum | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Soybean | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Sugar beet | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |

TABLE A-continued

| | | | | | | | | | | | | | | | | | | | | | | |
|---|---|---|---|---|---|---|---|---|---|---|---|---|---|---|---|---|---|---|---|---|---|---|
| Velvetleaf | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Wheat | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Wild buckwheat | — | — | — | — | — | — | 0 | 0 | 0 | 0 | — | — | — | — | — | — | — | — | — | 0 | 0 | 0 |
| Wild oat | 0 | 0 | 0 | 0 | 0 | 0 | 0 | 0 | 0 | 0 | 0 | 0 | 0 | 0 | 0 | 0 | 0 | 0 | 0 | 0 | 0 | 0 |

| | Rate (50 g/ha) | | | | | | | | | | | | | | | |
|---|---|---|---|---|---|---|---|---|---|---|---|---|---|---|---|---|
| COMPOUND | 51 | 52 | 53 | 54 | 55 | 56 | 57 | 58 | 59 | 60 | 61 | 62 | 63 | 64 | 65 | 66 |
| Barley | 0 | 0 | 0 | 0 | 0 | 0 | 0 | 0 | 0 | 0 | 0 | 0 | 0 | 0 | 0 | 0 |
| Barnyardgrass | 1 | 0 | 0 | 0 | 0 | 0 | 0 | 0 | 0 | 0 | 0 | 0 | 1 | 9 | 4 | 0 |
| Bedstraw | 0 | 0 | 0 | 0 | 0 | 0 | 0 | 0 | 0 | 0 | 0 | 0 | 0 | — | 0 | 0 |
| Blackgrass | 0 | 0 | 0 | 0 | 0 | 0 | 0 | 0 | 0 | 0 | 0 | 0 | 2 | 0 | 2 | 0 |
| Cheatgrass | 0 | 0 | 0 | 0 | 0 | 0 | 0 | 0 | 0 | 0 | 0 | 0 | 0 | 0 | 0 | 0 |
| Chickweed | 0 | 0 | 0 | — | 0 | 0 | — | 0 | 0 | 0 | 0 | 0 | 0 | 0 | 0 | 0 |
| Cocklebur | 0 | 0 | — | 0 | — | 0 | 0 | 0 | 0 | 0 | 0 | 0 | 0 | 0 | — | 0 |
| Corn | 1 | 0 | 0 | 0 | 0 | 0 | 0 | 0 | 0 | 0 | 0 | 0 | — | 0 | 0 | 0 |
| Cotton | 0 | 0 | 0 | 0 | 0 | 0 | 0 | 0 | 0 | 0 | 0 | 0 | 0 | 0 | 0 | 0 |
| Crabgrass | 2 | 0 | 2 | 0 | 1 | 0 | 0 | 0 | 0 | 0 | 0 | 3 | 1 | 3 | 2 | 0 |
| Giant foxtail | 0 | 0 | 2 | 0 | 0 | 0 | 0 | 0 | 0 | 0 | 0 | 0 | 1 | 8 | 4 | 5 |
| Lambsquarters | 0 | 0 | — | 0 | 0 | — | — | 0 | 0 | 0 | — | 0 | — | — | — | — |
| Morningglory | 0 | 0 | 0 | 0 | 0 | 0 | 0 | 0 | 0 | 0 | 0 | 0 | 0 | 0 | 0 | 0 |
| Nutsedge | 0 | 0 | — | 0 | 0 | 0 | 0 | 0 | 0 | 0 | 0 | 0 | 0 | 0 | 0 | 0 |
| Rape | 0 | 0 | 0 | 0 | 0 | 0 | 0 | 0 | 0 | 0 | 0 | 0 | 0 | 0 | 0 | 0 |
| Rice | 0 | 0 | 0 | 0 | 0 | 0 | 0 | 0 | 0 | 0 | 0 | 0 | 0 | 0 | 0 | 0 |
| Sorghum | 0 | 0 | 0 | 0 | 0 | 0 | 0 | 0 | 0 | 0 | 0 | 0 | 0 | 0 | 0 | 0 |
| Soybean | 0 | 0 | 0 | 0 | 0 | 0 | 0 | 0 | 0 | 0 | 0 | 0 | 0 | 0 | 0 | 0 |
| Sugar beet | 0 | 0 | 0 | 0 | 0 | 0 | 0 | 0 | 0 | 0 | 0 | 0 | 0 | 0 | 0 | 0 |
| Velvetleaf | 0 | 0 | 0 | 0 | 0 | 0 | 0 | 0 | 0 | 0 | 0 | 0 | 0 | 0 | 0 | 0 |
| Wheat | 0 | 0 | 0 | 0 | 0 | 0 | 0 | 0 | 0 | 0 | 0 | 0 | 0 | 0 | 0 | 0 |
| Wild buckwheat | 0 | 0 | 0 | 0 | — | 0 | 0 | — | — | — | — | — | — | 0 | 0 | — |
| Wild oat | 0 | 0 | 0 | 0 | 0 | 0 | 0 | 0 | 0 | 0 | 0 | 0 | 0 | 0 | 0 | 0 |

TEST B

The compounds evaluated in this test were formulated in a non-phytoxic solvent and applied to the soil surface before plant seedlings emerged (preemergence application), to water that covered the soil surface (paddy application), and to plants that were in the one-to-four stage (postemergence application). A sandy loam soil was used for the preemergence and postemergence tests, while a silt loam soil was used in the paddy test. Water depth was approximately 2.5 cm for the paddy test and was maintained at this level for the duration of the test.

Plant species in the preemergence and postemergence tests consisted of barley (*Hordeum vulgare*), bedstraw (*Galium aparine*), blackgrass (*Alopecurus myosuroides*), chickweed (*Stellaria media*), corn (*Zea mays*), cotton (*Gossypium hirsutum*), crabgrass (*Digitaria sanguinalis*), downy brome (*Bromus tectorum*), duck salad (*Heteranthera limosa*), giant foxtail (*Setaria faberii*), lambsquarters (*Chenopodium album*), morningglory (*Ipomoea hederacea*), pigweed (*Amaranthusretro flexus*), rape (*Lolium multiflorum*), rice (*Oryza sativa*), ryegrass (*Lolium multiflorum*), sorghum (*Sorghum bicolor*), soybean (*Glycine max*), speedwell (*Veronica persica*), sugar beet (*Beta vulgaris*), velvetleaf (*Abutilon theophrasti*), wheat (*Triticum aestivum*), wild buckwheat (*Polygonum convolvulus*) and wild oat (*Avena fatua*). All plant species were planted one day before application of the compound for the preemergence portion of this test. Plantings of these species were adjusted to produce plants of appropriate size for the postemergence portion of the test. Plant species in the paddy test consisted of barnyardgrass (*Echinochloa crus-galli*), rice (*Oryza sativa*), and umbrella sedge (*Cyperus difformis*).

All plant species were grown using normal greenhouse practices. Visual evaluations of injury expressed on treated plants, when compared to untreated controls, were recorded approximately fourteen to twenty-one days after application of the test compound. Plant response ratings, summarized in Table B, were recorded on a 0 to 10 scale where 0 is no injury and 10 is complete control. A dash (—) response means no test result.

TABLE B

| | COMPOUND | |
|---|---|---|
| | 4  6  7  8 | 18 | 19 |
| | POSTEMERGENCE | |
| Rate (500 g/ha) | | |
| Barley Igri | | 2 | 0 |
| Bedstraw | | 2 | 7 |
| Blackgrass | | 6 | 9 |
| Chickweed | | 0 | 5 |
| Corn | | 2 | 3 |
| Cotton | | 1 | 4 |
| Crabgrass | | 4 | 8 |
| Downy brome | | 0 | 2 |
| Duck salad | | 2 | 9 |
| Giant foxtail | | 2 | 8 |
| Lambsquarters | | 5 | 4 |
| Morningglory | | 0 | 0 |
| Pigweed | | 4 | 5 |
| Rape | | 4 | 3 |
| Ryegrass | | 0 | 0 |
| Sorghum | | 3 | 2 |
| Soybean | | 0 | 2 |
| Speedwell | | 3 | 4 |
| Sugar beet | | 5 | 6 |
| Velvetleaf | | 2 | 4 |
| Wheat | | 3 | 2 |
| Wild buckwheat | | 0 | 9 |
| Wild oat | | 0 | 0 |
| Barnyardgrass | | 10 | 10 |
| Rice Japonica | | 8 | 3 |
| Umbrella sedge | | 9 | 9 |
| Rate (250 g/ha) | | |

TABLE B-continued

| | COMPOUND | | | | | |
|---|---|---|---|---|---|---|
| | 4 | 6 | 7 | 8 | 18 | 19 |
| Barley Igri | 0 | 5 | 3 | 0 | 0 | 0 |
| Bedstraw | 0 | 0 | 0 | 0 | 0 | 6 |
| Blackgrass | 8 | 9 | — | 6 | 5 | 6 |
| Chickweed | 0 | 6 | 2 | 0 | 0 | 4 |
| Corn | 0 | 3 | 0 | 0 | 0 | 2 |
| Cotton | 0 | 0 | 0 | 0 | 0 | 3 |
| Crabgrass | 0 | 0 | 3 | 3 | 3 | 4 |
| Downy brome | 0 | 5 | 2 | 0 | 0 | 0 |
| Duck salad | 3 | 3 | 9 | 9 | 0 | 9 |
| Giant foxtail | 0 | 0 | 3 | 4 | 0 | 7 |
| Lambsquarters | 0 | 0 | — | 3 | 3 | 3 |
| Morningglory | 0 | 0 | 0 | 0 | 0 | 0 |
| Pigweed | 0 | 0 | 0 | 0 | 4 | 3 |
| Rape | 0 | 2 | 0 | 0 | 3 | 2 |
| Ryegrass | 5 | 5 | 7 | 0 | 0 | 0 |
| Sorghum | 0 | 0 | 0 | 0 | 2 | 2 |
| Soybean | 0 | 0 | 0 | 0 | 0 | 2 |
| Speedwell | 0 | 4 | 0 | 0 | 0 | 3 |
| Sugar beet | 0 | 6 | 2 | 0 | 3 | 5 |
| Velvetleaf | 0 | 0 | 0 | 0 | 0 | 2 |
| Wheat | 2 | 5 | 0 | 0 | 0 | 0 |
| Wild buckwheat | 0 | 0 | 0 | 0 | 0 | 5 |
| Wild oat | 0 | 3 | 0 | 0 | 0 | 0 |
| Barnyardgrass | 9 | 9 | 10 | 10 | 9 | 10 |
| Rice Japonica | 8 | 8 | 9 | 8 | 7 | 0 |
| Umbrella sedge | 9 | 9 | 9 | 9 | 9 | 9 |
| Rate (125 g/ha) | | | | | | |
| Barley Igri | 0 | 3 | 1 | 0 | 0 | 0 |
| Bedstraw | 0 | 0 | 0 | 0 | 0 | 5 |
| Blackgrass | 3 | 5 | 8 | 3 | 5 | 5 |
| Chickweed | 0 | 4 | 0 | 0 | 0 | 2 |
| Corn | 0 | 0 | 0 | 0 | 0 | 0 |
| Cotton | 0 | 0 | 0 | 0 | 0 | 2 |
| Crabgrass | 0 | 0 | 0 | 2 | 2 | 3 |
| Downy brome | 0 | 2 | 0 | 0 | 0 | 0 |
| Duck salad | 0 | 2 | 8 | 9 | 0 | 7 |
| Giant foxtail | 0 | 0 | 0 | 3 | 0 | 4 |
| Lambsquarters | 0 | 0 | 5 | 0 | 0 | 0 |
| Morningglory | 0 | 0 | 0 | 0 | 0 | 0 |
| Pigweed | 0 | 0 | 0 | 0 | 4 | 2 |
| Rape | 0 | 0 | 0 | 0 | 0 | 2 |
| Ryegrass | 0 | 3 | 5 | 0 | 0 | 0 |
| Sorghum | 0 | 0 | 0 | 0 | 0 | 0 |
| Soybean | 0 | 0 | 0 | 0 | 0 | 0 |
| Speedwell | 0 | 4 | 0 | 0 | 0 | 2 |
| Sugar beet | 0 | 0 | 0 | 0 | 0 | 5 |
| Velvetleaf | 0 | 0 | 0 | 0 | 0 | 2 |
| Wheat | 0 | 3 | 0 | 0 | 0 | 0 |
| Wild buckwheat | 0 | 0 | 0 | 0 | 0 | 5 |
| Wild oat | 0 | 0 | 0 | 0 | 0 | 0 |
| Barnyardgrass | 9 | 9 | 10 | 10 | 9 | 10 |
| Rice Japonica | 2 | 8 | 9 | 7 | 5 | 0 |
| Umbrella sedge | 7 | 9 | 9 | 9 | 7 | 8 |
| Rate (62 g/ha) | | | | | | |
| Barley Igri | 0 | 2 | 0 | 0 | 0 | 0 |
| Bedstraw | 0 | 0 | 0 | 0 | 0 | 5 |
| Blackgrass | 0 | 4 | 7 | 2 | 2 | 2 |
| Chickweed | 0 | 0 | 0 | 0 | 0 | 0 |
| Corn | 0 | 0 | 0 | 0 | 0 | 0 |
| Cotton | 0 | 0 | 0 | 0 | 0 | 0 |
| Crabgrass | 0 | 0 | 0 | 0 | 2 | 0 |
| Downy brome | 0 | 0 | 0 | 0 | 0 | 0 |
| Duck salad | 0 | 0 | 8 | 4 | 0 | 2 |
| Giant foxtail | 0 | 0 | 0 | 0 | 0 | 3 |
| Lambsquarters | 0 | 0 | 0 | 0 | 0 | 0 |
| Morningglory | 0 | 0 | 0 | 0 | 0 | 0 |
| Pigweed | 0 | 0 | 0 | 0 | 2 | 0 |
| Rape | 0 | 0 | 0 | 0 | 0 | 0 |
| Ryegrass | 0 | 0 | 2 | 0 | 0 | 0 |
| Sorghum | 0 | 0 | 0 | 0 | 0 | 0 |
| Soybean | 0 | 0 | 0 | 0 | 0 | 0 |
| Speedwell | 0 | 0 | 0 | 0 | 0 | 0 |
| Sugar beet | 0 | 0 | 0 | 0 | 0 | 2 |
| Velvetleaf | 0 | 0 | 0 | 0 | 0 | 2 |
| Wheat | 0 | 2 | 0 | 0 | 0 | 0 |
| Wild buckwheat | 0 | 0 | 0 | 0 | 0 | 4 |
| Wild oat | 0 | 0 | 0 | 0 | 0 | 0 |
| Barnyardgrass | 7 | 9 | 10 | 10 | 9 | 10 |
| Rice Japonica | 0 | 5 | 8 | 0 | 0 | 0 |
| Umbrella sedge | 7 | 9 | 9 | 9 | 7 | 7 |
| Rate (31 g/ha) | | | | | | |
| Barley Igri | 0 | 0 | 0 | 0 | 0 | 0 |
| Bedstraw | 0 | 0 | 0 | 0 | 0 | 4 |
| Blackgrass | 0 | 0 | 4 | 0 | 0 | 0 |
| Chickweed | 0 | 0 | 0 | 0 | 0 | 0 |
| Corn | 0 | 0 | 0 | 0 | 0 | 0 |
| Cotton | 0 | 0 | 0 | 0 | 0 | 0 |
| Crabgrass | 0 | 0 | 0 | 0 | 2 | 0 |
| Downy brome | 0 | 0 | 0 | 0 | 0 | 0 |
| Duck salad | 0 | 0 | 5 | 3 | 0 | 0 |
| Giant foxtail | 0 | 0 | 0 | 0 | 0 | 0 |
| Lambsquarters | 0 | 0 | 0 | 0 | 0 | 0 |
| Morningglory | 0 | 0 | 0 | 0 | 0 | 0 |
| Pigweed | 0 | 0 | 0 | 0 | 0 | 0 |
| Rape | 0 | 0 | 0 | 0 | 0 | 0 |
| Ryegrass | 0 | 0 | 0 | 0 | 0 | 0 |
| Sorghum | 0 | 0 | 0 | 0 | 0 | 0 |
| Soybean | 0 | 0 | 0 | 0 | 0 | 0 |
| Speedwell | 0 | 0 | 0 | 0 | 0 | 0 |
| Sugar beet | 0 | 0 | 0 | 0 | 0 | 0 |
| Velvetleaf | 0 | 0 | 0 | 0 | 0 | 0 |
| Wheat | 0 | 0 | 0 | 0 | 0 | 0 |
| Wild buckwheat | 0 | 0 | 0 | 0 | 0 | 2 |
| Wild oat | 0 | 0 | 0 | 0 | 0 | 0 |
| Barnyardgrass | 2 | 8 | 9 | 9 | 4 | 9 |
| Rice Japonica | 0 | 0 | 0 | 0 | 0 | 0 |
| Umbrella sedge | 3 | 4 | 8 | 7 | 0 | 2 |
| Rate (16 g/ha) | | | | | | |
| Barley Igri | 0 | 0 | 0 | 0 | | |
| Bedstraw | 0 | 0 | 0 | 0 | | |
| Blackgrass | 0 | 0 | 0 | 0 | | |
| Chickweed | 0 | 0 | 0 | 0 | | |
| Corn | 0 | 0 | 0 | 0 | | |
| Cotton | 0 | 0 | 0 | 0 | | |
| Crabgrass | 0 | 0 | 0 | 0 | | |
| Downy brome | 0 | 0 | 0 | 0 | | |
| Duck salad | 0 | 0 | 0 | 0 | | |
| Giant foxtail | 0 | 0 | 0 | 0 | | |
| Lambsquarters | 0 | 0 | 0 | 0 | | |
| Morningglory | 0 | 0 | 0 | 0 | | |
| Pigweed | 0 | 0 | 0 | 0 | | |
| Rape | 0 | 0 | 0 | 0 | | |
| Ryegrass | 0 | 0 | 0 | 0 | | |
| Sorghum | 0 | 0 | 0 | 0 | | |
| Soybean | 0 | 0 | 0 | 0 | | |
| Speedwell | 0 | 0 | 0 | 0 | | |
| Sugar beet | 0 | 0 | 0 | 0 | | |
| Velvetleaf | 0 | 0 | 0 | 0 | | |
| Wheat | 0 | 0 | 0 | 0 | | |
| Wild buckwheat | 0 | 0 | 0 | 0 | | |
| Wild oat | 0 | 0 | 0 | 0 | | |
| Barnyardgrass | 0 | 6 | 9 | 8 | | |
| Rice Japonica | 0 | 0 | 0 | 0 | | |
| Umbrella sedge | 3 | 0 | 0 | 2 | | |

PREEMERGENCE

Rate (500 g/ha)

| | COMPOUND | |
|---|---|---|
| | 18 | 19 |
| Barley Igri | 0 | 0 |
| Bedstraw | 0 | 4 |
| Blackgrass | 10 | 10 |
| Chickweed | 5 | 8 |
| Corn | 2 | 0 |
| Cotton | 0 | 3 |
| Crabgrass | 9 | 10 |

TABLE B-continued

| | COMPOUND | | | | | |
|---|---|---|---|---|---|---|
| | 4 | 6 | 7 | 8 | 18 | 19 |
| Downy brome | | | | | 6 | 0 |
| Duck salad | | | | | — | — |
| Giant foxtail | | | | | 9 | 10 |
| Lambsquarters | | | | | 6 | 5 |
| Morningglory | | | | | 3 | 0 |
| Pigweed | | | | | 4 | 5 |
| Rape | | | | | 0 | 5 |
| Ryegrass | | | | | 10 | 3 |
| Sorghum | | | | | 4 | 3 |
| Soybean | | | | | 2 | 0 |
| Speedwell | | | | | 6 | 3 |
| Sugar beet | | | | | 6 | 8 |
| Velvetleaf | | | | | 4 | 8 |
| Wheat | | | | | 3 | 4 |
| Wild buckwheat | | | | | 7 | 5 |
| Wild oat | | | | | 5 | 2 |
| Rate (125 g/ha) | | | | | | |
| Barley Igri | 3 | 2 | 0 | 0 | 0 | 0 |
| Bedstraw | 0 | — | 0 | 0 | 0 | 2 |
| Blackgrass | 10 | 10 | 10 | 10 | 9 | 8 |
| Chickweed | 3 | 7 | 7 | 0 | 0 | 6 |
| Corn | 4 | 3 | 4 | 4 | 2 | 0 |
| Cotton | 0 | 3 | 0 | 0 | 0 | 1 |
| Crabgrass | 4 | 5 | 7 | 10 | 8 | 10 |
| Downy brome | 5 | 10 | 5 | 0 | 3 | 0 |
| Duck salad | — | — | — | — | — | — |
| Giant foxtail | 3 | 0 | 3 | 6 | 8 | 9 |
| Lambsquarters | 4 | 9 | 6 | 4 | 2 | 5 |
| Morningglory | 0 | 0 | 0 | 0 | 0 | 0 |
| Pigweed | 0 | 0 | 5 | 0 | 2 | 5 |
| Rape | 0 | 0 | 0 | 0 | 0 | 3 |
| Ryegrass | 8 | 9 | 10 | 7 | 9 | 3 |
| Sorghum | 3 | 4 | 0 | 4 | 2 | 2 |
| Soybean | 0 | 0 | 2 | 0 | 0 | 0 |
| Speedwell | 7 | 9 | 8 | 0 | 0 | 2 |
| Sugar beet | 0 | 5 | 4 | 4 | 5 | 5 |
| Velvetleaf | 5 | 2 | 5 | 4 | 2 | 7 |
| Wheat | 3 | 4 | 0 | 0 | 0 | 0 |
| Wild buckwheat | 0 | 2 | 6 | 5 | 2 | 3 |
| Wild oat | 2 | 3 | 6 | 0 | 0 | 0 |
| Rate (62 g/ha) | | | | | | |
| Barley Igri | 2 | 0 | 0 | 0 | 0 | 0 |
| Bedstraw | 0 | 0 | 0 | 0 | 0 | 0 |
| Blackgrass | 8 | 10 | 10 | 9 | 8 | 5 |
| Chickweed | 0 | 4 | 7 | 0 | 0 | 3 |
| Corn | 1 | 2 | 3 | 0 | 0 | 0 |
| Cotton | 0 | 0 | 0 | 0 | 0 | 0 |
| Crabgrass | 0 | 3 | 7 | 10 | 7 | 10 |
| Downy brome | 2 | 5 | 4 | 0 | 2 | 0 |
| Duck salad | — | — | — | — | — | — |
| Giant foxtail | 2 | 0 | 3 | 3 | 6 | 9 |
| Lambsquarters | 4 | 3 | 5 | 3 | 0 | 2 |
| Morningglory | 0 | 0 | 0 | 0 | 0 | 0 |
| Pigweed | 0 | 0 | 4 | 0 | 0 | 3 |
| Rape | 0 | 0 | 0 | 0 | 0 | 2 |
| Ryegrass | 5 | 9 | 7 | 7 | 4 | 0 |
| Sorghum | 2 | 0 | 0 | 3 | 0 | 0 |
| Soybean | 0 | 0 | 0 | 0 | 0 | 0 |
| Speedwell | 3 | 8 | 7 | 0 | 0 | 0 |
| Sugar beet | 0 | 5 | 3 | 3 | 0 | 0 |
| Velvetleaf | 1 | 0 | 3 | 0 | 0 | 7 |
| Wheat | 3 | 0 | 0 | 0 | 0 | 0 |
| Wild buckwheat | 0 | 0 | 5 | 5 | 0 | 0 |
| Wild oat | 0 | 2 | 5 | 0 | 0 | 0 |
| Rate (62 g/ha) | | | | | | |
| Barley Igri | 0 | 0 | 0 | 0 | 0 | 0 |
| Bedstraw | 0 | — | 0 | 0 | 0 | 0 |
| Blackgrass | 3 | 7 | 8 | 7 | 5 | 4 |
| Chickweed | 0 | 3 | 5 | 0 | 0 | 0 |
| Corn | 0 | 0 | 0 | 0 | 0 | 0 |
| Cotton | 0 | 0 | 0 | 0 | 0 | 0 |
| Crabgrass | 0 | 0 | 3 | 10 | 4 | 9 |

TABLE B-continued

| | COMPOUND | | | | | |
|---|---|---|---|---|---|---|
| | 4 | 6 | 7 | 8 | 18 | 19 |
| Downy brome | 0 | 3 | 0 | 0 | 0 | 0 |
| Duck salad | — | — | — | — | — | — |
| Giant foxtail | 0 | 0 | 0 | 0 | 4 | 6 |
| Lambsquarters | 3 | 0 | 3 | 0 | 0 | 2 |
| Morningglory | 0 | 0 | 0 | 0 | 0 | 0 |
| Pigweed | 0 | 0 | 3 | 0 | 0 | 2 |
| Rape | 0 | 0 | 0 | 0 | 0 | 0 |
| Ryegrass | 3 | 5 | 7 | 3 | 0 | 0 |
| Sorghum | 0 | 0 | 0 | 0 | 0 | 0 |
| Soybean | 0 | 0 | 0 | 0 | 0 | 0 |
| Speedwell | 3 | 3 | 5 | 0 | 0 | 0 |
| Sugar beet | 0 | 3 | 2 | 0 | 0 | 0 |
| Velvetleaf | 0 | 0 | 0 | 0 | 0 | 2 |
| Wheat | 0 | 0 | 0 | 0 | 0 | 0 |
| Wild buckwheat | 0 | 0 | 4 | 4 | 0 | 0 |
| Wild oat | 0 | 0 | 0 | 0 | 0 | 0 |
| Rate (31 g/ha) | | | | | | |
| Barley Igri | 0 | 0 | 0 | 0 | 0 | 0 |
| Bedstraw | 0 | 0 | 0 | 0 | 0 | 0 |
| Blackgrass | 2 | 4 | 5 | 4 | 2 | 0 |
| Chickweed | 0 | 0 | 3 | 0 | 0 | 0 |
| Corn | 0 | 0 | 0 | 0 | 0 | 0 |
| Cotton | 0 | 0 | 0 | 0 | 0 | 0 |
| Crabgrass | 0 | 0 | 0 | 7 | 2 | 5 |
| Downy brome | 0 | 0 | 0 | 0 | 0 | 0 |
| Duck salad | — | — | — | — | — | — |
| Giant foxtail | 0 | 0 | 0 | 0 | 2 | 3 |
| Lambsquarters | 2 | 0 | 0 | 0 | 0 | 0 |
| Morningglory | 0 | 0 | 0 | 0 | 0 | 0 |
| Pigweed | 0 | 0 | 0 | 0 | 0 | 2 |
| Rape | 0 | 0 | 0 | 0 | 0 | 0 |
| Ryegrass | 0 | 2 | 5 | 0 | 0 | 0 |
| Sorghum | 0 | 0 | 0 | 0 | 0 | 0 |
| Soybean | 0 | 0 | 0 | 0 | 0 | 0 |
| Speedwell | 0 | 3 | 3 | 0 | 0 | 0 |
| Sugar beet | 0 | 0 | 0 | 0 | 0 | 0 |
| Velvetleaf | 0 | 0 | 0 | 0 | 0 | 0 |
| Wheat | 0 | 0 | 0 | 0 | 0 | 0 |
| Wild buckwheat | 0 | 0 | 3 | 3 | 0 | 0 |
| Wild oat | 0 | 0 | 0 | 0 | 0 | 0 |
| Rate (16 g/ha) | | | | | | |
| Barley Igri | 0 | 0 | 0 | 0 | | |
| Bedstraw | 0 | 0 | 0 | 0 | | |
| Blackgrass | 0 | 0 | 4 | 0 | | |
| Chickweed | 0 | 0 | 0 | 0 | | |
| Corn | 0 | 0 | 0 | 0 | | |
| Cotton | 0 | 0 | 0 | 0 | | |
| Crabgrass | 0 | 0 | 0 | 3 | | |
| Downy brome | 0 | 0 | 0 | 0 | | |
| Duck salad | — | — | — | — | | |
| Giant foxtail | 0 | 0 | 0 | 0 | | |
| Lambsquarters | — | 0 | 0 | 0 | | |
| Morningglory | 0 | 0 | 0 | 0 | | |
| Pigweed | 0 | 0 | 0 | 0 | | |
| Rape | 0 | 0 | 0 | 0 | | |
| Ryegrass | 0 | 0 | 0 | 0 | | |
| Sorghum | 0 | 0 | 0 | 0 | | |
| Soybean | 0 | 0 | 0 | 0 | | |
| Speedwell | 0 | 2 | 0 | 0 | | |
| Sugar beet | 0 | 0 | 0 | 0 | | |
| Velvetleaf | 0 | 0 | 0 | 0 | | |
| Wheat | 0 | 0 | 0 | 0 | | |
| Wild buckwheat | 0 | 0 | 3 | 3 | | |
| Wild oat | 0 | 0 | 0 | 0 | | |

TEST C

Plastic pots were partially filled with silt loam soil. The soil was then saturated with water. Japonica rice (*Oryza sativa*) seedlings at the 2.0 to 2.5 leaf stage, seeds selected from barnyardgrass (*Echinochloa crus-galli*), duck salad (*Heteranthera limosa*), umbrella sedge (*Cyperus difformis*), and tubers selected from arrowhead (Sagittaria spp.) and waterchestnut (Eleocharis spp.), were planted into this soil. After planting, water levels were raised to 3 cm above the soil surface and maintained at this level throughout the test. Chemical treatments were formulated in a non-phytotoxic solvent and applied directly to the paddy water. Treated plants and controls were maintained in a greenhouse for approximately 21 days, after which all species were compared to controls and visually evaluated. Plant response ratings, summarized in Table C, are reported on a 0 to 10 scale where 0 is no effect and 10 is complete control. A dash (—) response means no test result.

TABLE C

| | COMPOUND | | | | | |
|---|---|---|---|---|---|---|
| | 4 | 6 | 7 | 8 | 18 | 19 |
| Rate (1000 g/ha) PADDY | | | | | | |
| Arrowhead | | 5 | 5 | 3 | 3 | |
| Barnyardgrass | | 10 | 10 | 10 | 10 | |
| Japonica rice | | 6 | 5 | 3 | 2 | |
| Umbrella sedge | | 9 | 9 | 9 | 8 | |
| Waterchestnut | | 7 | 6 | 7 | 8 | |
| Rate (500 g/ha) PADDY | | | | | | |
| Arrowhead | — | 4 | 5 | 2 | 2 | 3 |
| Barnyardgrass | 10 | 10 | 9 | 10 | 10 | 10 |
| Duck salad | 10 | 10 | — | — | — | — |
| Japonica rice | 3 | 5 | 5 | 3 | 1 | 1 |
| Umbrella sedge | 10 | 9 | 9 | 9 | 7 | 9 |
| Waterchestnut | 6 | 6 | 6 | 6 | 6 | 7 |
| Rate (250 g/ha) PADDY | | | | | | |
| Arrowhead | — | 3 | 2 | 1 | 0 | 2 |
| Barnyardgrass | 10 | 10 | 10 | 10 | 9 | 9 |
| Duck salad | 10 | 10 | — | — | — | — |
| Japonica rice | 2 | 4 | 3 | 2 | 0 | 0 |
| Umbrella sedge | 9 | 9 | 9 | 9 | 7 | 9 |
| Waterchestnut | 4 | 7 | 6 | 4 | 6 | 3 |
| Rate (125 g/ha) PADDY | | | | | | |
| Arrowhead | — | 3 | 2 | 1 | 0 | 0 |
| Barnyardgrass | 8 | 10 | 10 | 10 | 8 | 7 |
| Duck salad | 9 | 8 | — | — | — | — |
| Japonica rice | 1 | 2 | 1 | 1 | 0 | 0 |
| Umbrella sedge | 8 | 9 | 8 | 8 | 6 | 7 |
| Waterchestnut | 2 | 3 | 5 | 4 | 4 | 2 |
| Rate (64 g/ha) PADDY | | | | | | |
| Arrowhead | — | 1 | 0 | 0 | 0 | 0 |
| Barnyardgrass | 4 | 7 | 9 | 9 | 2 | 5 |
| Duck salad | 8 | 5 | — | — | — | — |
| Japonica rice | 0 | 1 | 1 | 0 | 0 | 0 |
| Umbrella sedge | 6 | 8 | 8 | 6 | 4 | 7 |
| Waterchestnut | 0 | 2 | 4 | 0 | 0 | 3 |
| Rate (32 g/ha) PADDY | | | | | | |
| Arrowhead | — | — | | | | 0 |
| Barnyardgrass | 0 | 4 | | | | 1 |
| Duck salad | 0 | 0 | | | | — |
| Japonica rice | 0 | 1 | | | | 0 |
| Umbrella sedge | 1 | 0 | | | | 5 |
| Waterchestnut | 0 | 0 | | | | 3 |

TEST D

Plastic pots were partially filled with silt loam soil. The soil was then flooded with water, Japonica rice (*Oryza sativa*) sprouted seeds and 1.5 leaf transplants were planted in the soil. Seeds of barnyardgrass (*Echinochloa crus-galli*) were planted in saturated soil and plants grown to the 1 leaf, 2 leaf and 3 leaf stages for testing. At testing, the water level for all plantings was raised to 2 cm above the soil surface. Chemical treatments were formulated in a non-phytotoxic solvent and applied directly to the paddy water. Treated plants and controls were maintained in a greenhouse for approximately 21 days, after which all species were compared to controls and visually evaluated. Plant response ratings, summarized in Table D are reported on a 0 to 10 scale where 0 is no effect and 10 is complete control. A dash (—) response means no test result.

TABLE D

| | COMPOUND | | | | | |
|---|---|---|---|---|---|---|
| | 4 | 6 | 7 | 8 | 18 | 19 |
| Rate (1000 g/ha) Flood | | | | | | |
| 1-LF B.Y.Grass | 10 | | | | | |
| 2-LF B.Y.Grass | 9 | | | | | |
| 3-lf B.Y.Grass | 9 | | | | | |
| Jap Direct Seed | 9 | | | | | |
| Jap Price Eff | 7 | | | | | |
| Rate (500 g/ha) Flood | | | | | | |
| 1-LF B.Y.Grass | 9 | 10 | | 10 | 10 | 10 |
| 2-LF B.Y.Grass | 8 | 10 | | 10 | 8 | 8 |
| 3-lf B.Y.Grass | 8 | 9 | | 9 | 7 | 9 |
| Jap Direct Seed | 10 | 10 | | 9 | 6 | 0 |
| Jap Rice Eff | 5 | 5 | | 2 | 0 | 0 |
| Rate (250 g/ha) Flood | | | | | | |
| 1-LF B.Y.Grass | 9 | 10 | 10 | 10 | 9 | 10 |
| 2-LF B.Y.Grass | 8 | 9 | 10 | 10 | 7 | 7 |
| 3-lf B.Y.Grass | 7 | 9 | 8 | 9 | 7 | 6 |
| Jap Direct Seed | 9 | 9 | 10 | 9 | 6 | 0 |
| Jap Rice Eff | 4 | 4 | 7 | 2 | 0 | 0 |
| Rate (125 g/ha) Flood | | | | | | |
| 1-LF B.Y.Grass | 9 | 10 | 10 | 10 | 9 | 10 |
| 2-LF B.Y.Grass | 8 | 7 | 9 | 9 | 7 | 3 |
| 3-lf B.Y.Grass | 7 | 7 | 7 | 9 | 2 | 2 |
| Jap Direct Seed | 6 | 8 | 9 | 8 | 3 | 1 |
| Jap Rice Eff | 5 | 1 | 6 | 0 | 0 | 0 |
| Rate (64 g/ha) Flood | | | | | | |
| 1-LF B.Y.Grass | 6 | 8 | 10 | 10 | 6 | 8 |
| 2-LF B.Y.Grass | 2 | 5 | 7 | 7 | 7 | 0 |
| 3-lf B.Y.Grass | 3 | 3 | 5 | 7 | 0 | 0 |
| Jap Direct Seed | 3 | 7 | 9 | 7 | 1 | 0 |
| Jap Rice Eff | 0 | 2 | 4 | 0 | 0 | 0 |
| Rate (32 g/ha) Flood | | | | | | |
| 1-LF B.Y.Grass | 0 | 8 | 10 | 9 | 5 | 3 |
| 2-LF B.Y.Grass | 1 | 2 | 8 | 3 | 0 | 0 |
| 3-lf B.Y.Grass | 0 | 0 | 5 | 3 | 0 | 0 |
| Jap Direct Seed | 0 | 4 | 9 | 3 | 1 | 0 |
| Jap Rice Eff | 0 | 2 | 2 | 1 | 0 | 0 |
| Rate (16 g/ha) Flood | | | | | | |
| 1-LF B.Y.Grass | | 6 | 0 | | | |
| 2-LF B.Y.Grass | | 3 | 0 | | | |
| 3-lf B.Y.Grass | | 2 | 0 | | | |
| Jap Direct Seed | | 4 | 1 | | | |
| Jap Rice Eff | | 0 | 0 | | | |

TEST E

Compounds evaluated in this test were formulated in a non-phytotoxic solvent and applied to the soil surface before plant seedlings emerged (preemergence application) and to plants that were in the one-to-four leaf stage (postemergence application). A sandy loam soil was used for the preemergence test while a mixture of sandy loam soil and greenhouse potting mix in a 60:40 ratio was used for the postemergence test. Test compounds were applied within approximately one day after planting seeds for the preemergence test. Plantings of these crops and weed species were adjusted to produce plants of appropriate size for the postemergence test. All plant species were grown using normal greenhouse practices. Crop and weed species include winter barley (*Hordeum vulgare* cv. 'Igri'), bedstraw (*Galium aparine*), blackgrass (*Alopecures myosuroides*), chickweed (*Stellaria media*), downy brome (*Bromus tectorum*), field violet (*Viola arvensis*), green foxtail (*Setaria viridis*), kochia (*Kochia scoparia*), lambsquarters (*Chenopodium album*), Persian speedwell (*Veronica persica*), rape (*Brassica napus* cv. 'Jet Neuf'), ryegrass (*Lolium multiflorum*), sugar beet (*Beta vulgaris* cv. 'US1'), sunflower (*Helianthus annuus* cv. 'Russian Giant'), spring wheat (*Triticum aestivum* cv. 'ERA'), winter wheat (*Triticum aestivum* cv. 'Talent'), wild buckwheat (*Polygonum convolvulus*), wild mustard (*Sinapis arvensis*), wild oat (*Avena fatua*), and wild radish (*Raphanus raphanistrum*). Blackgrass and wild oat were treated postemergence at two growth stages. The first stage (1) was when the plants had two to three leaves. The second stage (2) was when the plants had approximately four leaves or in the initial stages of tillering. Treated plants and untreated controls were maintained in a greenhouse for approximately 21 to 28 days, after which all treated plants were compared to untreated controls and visually evaluated. Plant response ratings, summarized in Table E, are based upon a 0 to 10 scale where 0 is no effect and 10 is complete control. A dash response (–) means no test result.

TABLE E

| | COMPOUND | | | | |
|---|---|---|---|---|---|
| | 4 | 5 | 6 | 7 | 18 |
| POSTEMERGENCE | | | | | |
| Rate (2000 g/ha) | | | | | |
| Blackgrass (1) | 0 | 0 | 5 | | |
| Blackgrass (2) | 0 | 0 | 6 | | |
| Chickweed | 0 | 0 | 0 | | |
| Downy brome | 0 | 0 | 0 | | |
| Field violet | 0 | 0 | 0 | | |
| Galium (1) | 0 | 0 | 0 | | |
| Green foxtail | 0 | 0 | 0 | | |
| Lambsquarters | 0 | 0 | 0 | | |
| Persn Speedwell | 0 | 0 | 0 | | |
| Rape | 0 | 0 | 0 | | |
| Ryegrass | 0 | 0 | 2 | | |
| Sugar beet | 0 | 0 | 0 | | |
| Sunflower | 0 | 0 | 0 | | |
| Wheat (Spring) | 0 | 0 | 0 | | |
| Wheat (Winter) | 0 | 0 | 0 | | |
| Wild buckwheat | 0 | 0 | 0 | | |
| Wild mustard | 0 | 0 | 0 | | |
| Wild oat (1) | 0 | 0 | 0 | | |
| Wild oat (2) | 0 | 0 | 0 | | |
| Wild radish | 0 | 0 | 0 | | |
| Winter Barley | 0 | 0 | 0 | | |
| Rate (1000 g/ha) | | | | | |
| Blackgrass (1) | 0 | 0 | 2 | | |
| Blackgrass (2) | 0 | 0 | 3 | | |
| Chickweed | 0 | 0 | 0 | | |
| Downy brome | 0 | 0 | 0 | | |
| Field violet | 0 | 0 | 0 | | |
| Galium (1) | 0 | 0 | 0 | | |
| Green foxtail | 0 | 0 | 0 | | |
| Lambsquarters | 0 | 0 | 0 | | |
| Persn Speedwell | 0 | 0 | 0 | | |
| Rape | 0 | 0 | 0 | | |
| Ryegrass | 0 | 0 | 0 | | |
| Sugar beet | 0 | 0 | 0 | | |
| Sunflower | 0 | 0 | 0 | | |
| Wheat (Spring) | 0 | 0 | 0 | | |
| Wheat (Winter) | 0 | 0 | 0 | | |
| Wild buckwheat | 0 | 0 | 0 | | |
| Wild mustard | 0 | 0 | 0 | | |
| Wild oat (1) | 0 | 0 | 0 | | |
| Wild oat (2) | 0 | 0 | 0 | | |
| Wild radish | 0 | 0 | 0 | | |
| Winter Barley | 0 | 0 | 0 | | |
| Rate (500 g/ha) | | | | | |
| Blackgrass (1) | 0 | 0 | 0 | 6 | 0 |
| Blackgrass (2) | 0 | 0 | 0 | 8 | 0 |
| Chickweed | 0 | 0 | 0 | 0 | 0 |
| Downy brome | 0 | 0 | 0 | 0 | 0 |
| Field violet | 0 | 0 | 0 | 0 | 0 |
| Galium (1) | 0 | 0 | 0 | 0 | 0 |
| Galium (2) | — | — | — | 0 | — |
| Green foxtail | 0 | 0 | 0 | 0 | 0 |
| Kochia | — | — | — | 0 | 0 |
| Lambsquarters | 0 | 0 | 0 | 0 | 0 |
| Persn Speedwell | 0 | 0 | 0 | 0 | 0 |
| Rape | 0 | 0 | 0 | 0 | 0 |
| Ryegrass | 0 | 0 | 0 | 2 | 0 |
| Sugar beet | 0 | 0 | 0 | 0 | 0 |
| Sunflower | 0 | 0 | 0 | 0 | 0 |
| Wheat (Spring) | 0 | 0 | 0 | 0 | 0 |
| Wheat (Winter) | 0 | 0 | 0 | 0 | 0 |
| Wild buckwheat | 0 | 0 | 0 | 0 | 0 |
| Wild mustard | 0 | 0 | 0 | 0 | 0 |
| Wild oat (1) | 0 | 0 | 0 | 0 | 0 |
| Wild oat (2) | 0 | 0 | 0 | 0 | 0 |
| Wild radish | 0 | 0 | 0 | 0 | 0 |
| Winter Barley | 0 | 0 | 0 | 0 | 0 |
| Rate (250 g/ha) | | | | | |
| Blackgrass (1) | 0 | 0 | 0 | 3 | 0 |
| Blackgrass (2) | 0 | 0 | 0 | 4 | 0 |
| Chickweed | 0 | 0 | 0 | 0 | 0 |
| Downy brome | 0 | 0 | 0 | 0 | 0 |
| Field violet | 0 | 0 | 0 | 0 | 0 |
| Galium (1) | 0 | 0 | 0 | 0 | 0 |
| Galium (2) | — | — | — | 0 | — |
| Green foxtail | 0 | 0 | 0 | 0 | 0 |
| Kochia | — | — | — | 0 | 0 |
| Lambsquarters | 0 | 0 | 0 | 0 | 0 |
| Persn Speedwell | 0 | 0 | 0 | 0 | 0 |
| Rape | 0 | 0 | 0 | 0 | 0 |
| Ryegrass | 0 | 0 | 0 | 0 | 0 |
| Sugar beet | 0 | 0 | 0 | 0 | 0 |
| Sunflower | 0 | 0 | 0 | 0 | 0 |
| Wheat (Spring) | 0 | 0 | 0 | 0 | 0 |
| Wheat (Winter) | 0 | 0 | 0 | 0 | 0 |
| Wild buckwheat | 0 | 0 | 0 | 0 | 0 |
| Wild mustard | 0 | 0 | 0 | 0 | 0 |
| Wild oat (1) | 0 | 0 | 0 | 0 | 0 |
| Wild oat (2) | 0 | 0 | 0 | 0 | 0 |
| Wild radish | 0 | 0 | 0 | 0 | 0 |
| Winter Barley | 0 | 0 | 0 | 0 | 0 |
| Rate (125 g/ha) | | | | | |
| Blackgrass (1) | 0 | 0 | 0 | 0 | 0 |
| Blackgrass (2) | 0 | 0 | 0 | 0 | 0 |
| Chickweed | 0 | 0 | 0 | 0 | 0 |
| Downy brome | 0 | 0 | 0 | 0 | 0 |
| Field violet | 0 | 0 | 0 | 0 | 0 |
| Galium (1) | 0 | 0 | 0 | 0 | 0 |
| Galium (2) | — | — | — | 0 | — |
| Green foxtail | 0 | 0 | 0 | 0 | 0 |
| Kochia | — | — | — | 0 | 0 |
| Lambsquarters | 0 | 0 | 0 | 0 | 0 |
| Persn Speedwell | 0 | 0 | 0 | 0 | 0 |

TABLE E-continued

| | COMPOUND | | | | |
|---|---|---|---|---|---|
| | 4 | 5 | 6 | 7 | 18 |
| Rape | 0 | 0 | 0 | 0 | 0 |
| Ryegrass | 0 | 0 | 0 | 0 | 0 |
| Sugar beet | 0 | 0 | 0 | 0 | 0 |
| Sunflower | 0 | 0 | 0 | 0 | 0 |
| Wheat (Spring) | 0 | 0 | 0 | 0 | 0 |
| Wheat (Winter) | 0 | 0 | 0 | 0 | 0 |
| Wild buckwheat | 0 | 0 | 0 | 0 | 0 |
| Wild mustard | 0 | 0 | 0 | 0 | 0 |
| Wild oat (1) | 0 | 0 | 0 | 0 | 0 |
| Wild oat (2) | 0 | 0 | 0 | 0 | 0 |
| Wild radish | 0 | 0 | 0 | 0 | 0 |
| Winter Barley | 0 | 0 | 0 | 0 | 0 |
| Rate (64 g/ha) | | | | | |
| Blackgrass (1) | | | | 0 | |
| Blackgrass (2) | | | | 0 | |
| Chickweed | | | | 0 | |
| Downy brome | | | | 0 | |
| Field violet | | | | 0 | |
| Galium (1) | | | | 0 | |
| Galium (2) | | | | 0 | |
| Green foxtail | | | | 0 | |
| Kochia | | | | 0 | |
| Lambsquarters | | | | 0 | |
| Persn Speedwell | | | | 0 | |
| Rape | | | | 0 | |
| Ryegrass | | | | 0 | |
| Sugar beet | | | | 0 | |
| Sunflower | | | | 0 | |
| Wheat (Spring) | | | | 0 | |
| Wheat (Winter) | | | | 0 | |
| Wild buckwheat | | | | 0 | |
| Wild mustard | | | | 0 | |
| Wild oat (1) | | | | 0 | |
| Wild oat (2) | | | | 0 | |
| Wild radish | | | | 0 | |
| Winter Barley | | | | 0 | |
| Rate (32 g/ha) | | | | | |
| Blackgrass (1) | | | | 0 | |
| Blackgrass (2) | | | | 0 | |
| Chickweed | | | | 0 | |
| Downy brome | | | | 0 | |
| Field violet | | | | 0 | |
| Galium (1) | | | | 0 | |
| Galium (2) | | | | 0 | |
| Green foxtail | | | | 0 | |
| Kochia | | | | 0 | |
| Lambsquarters | | | | 0 | |
| Persn Speedwell | | | | 0 | |
| Rape | | | | 0 | |
| Ryegrass | | | | 0 | |
| Sugar beet | | | | 0 | |
| Sunflower | | | | 0 | |
| Wheat (Spring) | | | | 0 | |
| Wheat (Winter) | | | | 0 | |
| Wild buckwheat | | | | 0 | |
| Wild mustard | | | | 0 | |
| Wild oat (1) | | | | 0 | |
| Wild oat (2) | | | | 0 | |
| Wild radish | | | | 0 | |
| Winter Barley | | | | 0 | |
| Rate (16 g/ha) | | | | | |
| Blackgrass (1) | | | | 0 | |
| Blackgrass (2) | | | | 0 | |
| Chickweed | | | | 0 | |
| Downy brome | | | | 0 | |
| Field violet | | | | 0 | |
| Galium (1) | | | | 0 | |
| Galium (2) | | | | 0 | |
| Green foxtail | | | | 0 | |
| Kochia | | | | 0 | |
| Lambsquarters | | | | 0 | |
| Persn Speedwell | | | | 0 | |

TABLE E-continued

| | COMPOUND | | | | |
|---|---|---|---|---|---|
| | 4 | 5 | 6 | 7 | 18 |
| Rape | | | | 0 | |
| Ryegrass | | | | 0 | |
| Sugar beet | | | | 0 | |
| Sunflower | | | | 0 | |
| Wheat (Spring) | | | | 0 | |
| Wheat (Winter) | | | | 0 | |
| Wild buckwheat | | | | 0 | |
| Wild mustard | | | | 0 | |
| Wild oat (1) | | | | 0 | |
| Wild oat (2) | | | | 0 | |
| Wild radish | | | | 0 | |
| Winter Barley | | | | 0 | |
| | PREEMERGENCE | | | | |
| Rate (2000 g/ha) | | | | | |
| Blackgrass (1) | 10 | 10 | 10 | | |
| Blackgrass (2) | 10 | 10 | 10 | | |
| Chickweed | 7 | 4 | 8 | | |
| Downy brome | 9 | 9 | 10 | | |
| Field violet | 0 | 0 | 4 | | |
| Galium (1) | 6 | 8 | 9 | | |
| Green foxtail | 8 | 9 | 10 | | |
| Lambsquarters | — | — | — | | |
| Persn Speedwell | 7 | 0 | 4 | | |
| Rape | 0 | 2 | 4 | | |
| Ryegrass | 10 | 10 | 10 | | |
| Sugar beet | 2 | 2 | 6 | | |
| Sunflower | 0 | 0 | 0 | | |
| wheat (spring) | 6 | 5 | 6 | | |
| Wheat (Winter) | 6 | 8 | 7 | | |
| Wild buckwheat | 4 | 0 | 3 | | |
| Wild mustard | 2 | 0 | 0 | | |
| Wild oat (1) | 5 | 4 | 5 | | |
| Wild oat (2) | 5 | 5 | 7 | | |
| Wild radish | 0 | 0 | 5 | | |
| Winter Barley | 6 | 5 | 6 | | |
| Rate (1000 g/ha) | | | | | |
| Blackgrass (1) | 10 | 8 | 10 | | |
| Blackgrass (2) | 10 | 9 | 10 | | |
| Chickweed | 3 | 2 | 6 | | |
| Downy brome | 7 | 7 | 10 | | |
| Field violet | 0 | 0 | 2 | | |
| Galium (1) | 3 | 3 | 6 | | |
| Green foxtail | 6 | 6 | 9 | | |
| Lambsquarters | — | — | — | | |
| Persn Speedwell | 4 | 0 | 2 | | |
| Rape | 0 | 0 | 2 | | |
| Ryegrass | 10 | 9 | 10 | | |
| Sugar beet | 0 | 0 | 3 | | |
| Sunflower | 0 | 0 | 0 | | |
| Wheat (Spring) | 4 | 2 | 3 | | |
| Wheat (Winter) | 4 | 3 | 5 | | |
| Wild buckwheat | 2 | 0 | 0 | | |
| Wild mustard | 0 | 0 | 0 | | |
| Wild oat (1) | 3 | 2 | 2 | | |
| Wild oat (2) | 3 | 2 | 4 | | |
| Wild radish | 0 | 0 | 3 | | |
| Winter Barley | 4 | 2 | 4 | | |
| Rate (500 g/ha) | | | | | |
| Blackgrass (1) | 10 | 5 | 10 | 10 | 10 |
| Blackgrass (2) | 10 | 6 | 10 | 10 | 10 |
| Chickweed | 0 | 0 | 4 | 8 | 0 |
| Downy brome | 5 | 3 | 8 | 7 | 0 |
| Field violet | 0 | 0 | 0 | 4 | 0 |
| Galium (1) | 0 | 0 | 4 | 2 | 0 |
| Galium (2) | — | — | — | 3 | — |
| Green foxtail | 3 | 4 | 8 | 7 | 10 |
| Kochia | — | — | — | 0 | 0 |
| Lambsquarters | — | — | — | 2 | 0 |
| Persn Speedwell | 2 | 0 | 0 | 8 | 0 |
| Rape | 0 | 0 | 0 | — | 0 |
| Ryegrass | 8 | 6 | 10 | 10 | 9 |

TABLE E-continued

| | COMPOUND | | | | |
|---|---|---|---|---|---|
| | 4 | 5 | 6 | 7 | 18 |
| Sugar beet | 0 | 0 | 0 | 5 | 0 |
| Sunflower | 0 | 0 | 0 | 0 | 0 |
| Wheat (Spring) | 2 | 0 | 0 | 6 | 0 |
| Wheat (Winter) | 2 | 0 | 3 | 6 | 0 |
| Wild buckwheat | 0 | 0 | 0 | 0 | 0 |
| Wild mustard | 0 | 0 | 0 | 0 | 0 |
| Wild oat (1) | 0 | 0 | 0 | 5 | 0 |
| Wild oat (2) | 0 | 0 | 0 | 6 | 0 |
| Wild radish | 0 | 0 | 0 | 2 | 0 |
| Winter Barley | 2 | 0 | 1 | 7 | 0 |
| Rate (250 g/ha) | | | | | |
| Blackgrass (1) | 6 | 2 | 10 | 10 | 8 |
| Blackgrass (2) | 7 | 3 | 10 | 10 | 9 |
| Chickweed | 0 | 0 | 2 | 6 | 0 |
| Downy brome | 3 | 0 | 6 | 5 | 0 |
| Field violet | 0 | 0 | 0 | 2 | 0 |
| Galium (1) | 0 | 0 | 2 | 0 | 0 |
| Galium (2) | — | — | — | 0 | — |
| Green foxtail | 0 | 2 | 7 | 5 | 4 |
| Kochia | — | — | — | 0 | 0 |
| Lambsquarters | — | — | — | 0 | 0 |
| Persn Speedwell | 0 | 0 | 0 | 6 | 0 |
| Rape | 0 | 0 | 0 | — | 0 |
| Ryegrass | 4 | 2 | 8 | 10 | 7 |
| Sugar beet | 0 | 0 | 0 | 2 | 0 |
| Sunflower | 0 | 0 | 0 | 0 | 0 |
| Wheat (Spring) | 0 | 0 | 0 | 3 | 0 |
| Wheat (Winter) | 0 | 0 | 0 | 3 | 0 |
| Wild buckwheat | 0 | 0 | 0 | 0 | 0 |
| Wild mustard | 0 | 0 | 0 | 0 | 0 |
| Wild oat (1) | 0 | 0 | 0 | 3 | 0 |
| Wild oat (2) | 0 | 0 | 0 | 4 | 0 |
| Wild radish | 0 | 0 | 0 | 0 | 0 |
| Winter Barley | 0 | 0 | 0 | 5 | 0 |
| Rate (125 g/ha) | | | | | |
| Blackgrass (1) | 4 | 0 | 8 | 10 | 6 |
| Blackgrass (2) | 5 | 0 | 8 | 10 | 6 |
| Chickweed | 0 | 0 | 0 | 2 | 0 |
| Downy brome | 0 | 0 | 2 | 2 | 0 |
| Field violet | 0 | 0 | 0 | 0 | 0 |
| Galium (1) | 0 | 0 | 0 | 0 | 0 |
| Galium (2) | — | — | — | 0 | — |
| Green foxtail | 0 | 0 | 5 | 3 | 0 |
| Kochia | — | — | — | 0 | 0 |
| Lambsquarters | — | — | — | 0 | 0 |
| Persn Speedwell | 0 | 0 | 0 | 3 | 0 |
| Rape | 0 | 0 | 0 | — | 0 |
| Ryegrass | 2 | 0 | 5 | 9 | 4 |
| Sugar beet | 0 | 0 | 0 | 0 | 0 |
| Sunflower | 0 | 0 | 0 | 0 | 0 |
| Wheat (Spring) | 0 | 0 | 0 | 0 | 0 |
| Wheat (Winter) | 0 | 0 | 0 | 0 | 0 |
| Wild buckwheat | 0 | 0 | 0 | 0 | 0 |
| Wild mustard | 0 | 0 | 0 | 0 | 0 |
| Wild oat (1) | 0 | 0 | 0 | 0 | 0 |
| Wild oat (2) | 0 | 0 | 0 | 0 | 0 |
| Wild radish | 0 | 0 | 0 | 0 | 0 |
| Winter Barley | 0 | 0 | 0 | 2 | 0 |
| Rate (64 g/ha) | | | | | |
| Blackgrass (1) | 2 | 0 | 3 | 7 | 3 |
| Blackgrass (2) | 2 | 0 | 4 | 8 | 4 |
| Chickweed | 0 | 0 | 0 | 0 | 0 |
| Downy brome | 0 | 0 | 0 | 0 | 0 |
| Field violet | 0 | 0 | 0 | 0 | 0 |
| Galium (1) | 0 | 0 | 0 | 0 | 0 |
| Galium (2) | — | — | — | 0 | — |
| Green foxtail | 0 | 0 | 2 | 0 | 0 |
| Kochia | — | — | — | 0 | 0 |
| Lambsquarters | — | — | — | 0 | 0 |
| Persn Speedwell | 0 | 0 | 0 | 0 | 0 |
| Rape | 0 | 0 | 0 | — | 0 |
| Ryegrass | 0 | 0 | 2 | 8 | 2 |
| Sugar beet | 0 | 0 | 0 | 0 | 0 |
| Sunflower | 0 | 0 | 0 | 0 | 0 |
| Wheat (Spring) | 0 | 0 | 0 | 0 | 0 |
| Wheat (Winter) | 0 | 0 | 0 | 0 | 0 |
| Wild buckwheat | 0 | 0 | 0 | 0 | 0 |
| Wild mustard | 0 | 0 | 0 | 0 | 0 |
| Wild oat (1) | 0 | 0 | 0 | 0 | 0 |
| Wild oat (2) | 0 | 0 | 0 | 0 | 0 |
| Wild radish | 0 | 0 | 0 | 0 | 0 |
| Winter Barley | 0 | 0 | 0 | 0 | 0 |
| Rate (32 g/ha) | | | | | |
| Blackgrass (1) | 0 | 0 | 0 | 3 | 0 |
| Blackgrass (2) | 0 | 0 | 2 | 4 | 0 |
| Chickweed | 0 | 0 | 0 | 0 | 0 |
| Downy brome | 0 | 0 | 0 | 0 | 0 |
| Field violet | 0 | 0 | 0 | 0 | 0 |
| Galium (1) | 0 | 0 | 0 | 0 | 0 |
| Galium (2) | — | — | — | 0 | — |
| Green foxtail | 0 | 0 | 0 | 0 | 0 |
| Kochia | — | — | — | 0 | 0 |
| Lambsquarters | — | — | — | 0 | 0 |
| Persn Speedwell | 0 | 0 | 0 | 0 | 0 |
| Rape | 0 | 0 | 0 | — | 0 |
| Ryegrass | 0 | 0 | 0 | 5 | 0 |
| Sugar beet | 0 | 0 | 0 | 0 | 0 |
| Sunflower | 0 | 0 | 0 | 0 | 0 |
| Wheat (Spring) | 0 | 0 | 0 | 0 | 0 |
| Wheat (Winter) | 0 | 0 | 0 | 0 | 0 |
| Wild buckwheat | 0 | 0 | 0 | 0 | 0 |
| Wild mustard | 0 | 0 | 0 | 0 | 0 |
| Wild oat (1) | 0 | 0 | 0 | 0 | 0 |
| Wild oat (2) | 0 | 0 | 0 | 0 | 0 |
| Wild radish | 0 | 0 | 0 | 0 | 0 |
| Winter Barley | 0 | 0 | 0 | 0 | 0 |
| Rate (16 g/ha) | | | | | |
| Blackgrass (1) | | | | | 0 |
| Blackgrass (2) | | | | | 0 |
| Chickweed | | | | | 0 |
| Downy brome | | | | | 0 |
| Field violet | | | | | 0 |
| Galium (1) | | | | | 0 |
| Galium (2) | | | | | 0 |
| Green foxtail | | | | | 0 |
| Kochia | | | | | 0 |
| Lambsquarters | | | | | 0 |
| Persn Speedwell | | | | | 0 |
| Rape | | | | | — |
| Ryegrass | | | | | 2 |
| Sugar beet | | | | | 0 |
| Sunflower | | | | | 0 |
| Wheat (Spring) | | | | | 0 |
| Wheat (Winter) | | | | | 0 |
| Wild buckwheat | | | | | 0 |
| Wild mustard | | | | | 0 |
| Wild oat (1) | | | | | 0 |
| Wild oat (2) | | | | | 0 |
| Wild radish | | | | | 0 |
| Minter Barley | | | | | 0 |

What is claimed is:

1. A compound selected from

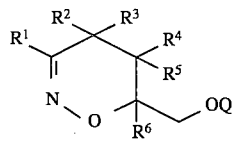

wherein:

$R^1$ is $C_1$–$C_6$ alkyl optionally substituted with a substituent selected from halogen, phenyl and $C_1$–$C_3$ alkoxy optionally substituted with 1–3 halogens; $C_3$–$C_6$ cycloalkyl; phenyl optionally substituted with one to two groups selected from halogen, $SCH_3$, CN, $C_1$–$C_2$ alkyl optionally substituted with 1–3 halogens and $C_1$–$C_2$ alkoxy optionally substituted with 1–3 halogens; and $CR^9R^{10}X$;

X is CN, $CO_2R^{13}$, $C(O)R^{14}$, CHO, $OR^{15}$ or $CR^{11}R^{12}Y$;

Y is $OR^{16}$;

$R^2$, $R^3$, $R^4$, $R^5$, $R^{13}$, $R^{14}$, $R^{15}$, $R^{16}$, $R^{20}$ and $R^{21}$ are independently H or $C_1$–$C_3$ alkyl;

$R^6$ is H, $C_1$–$C_3$ alkyl or $C_2$–$C_4$ alkenyl;

$R^1$ and $R^2$ may be taken together to form a 5–6 membered ring substituted with $R^{20}$ and $R^{21}$ and optionally fused to a benzene ring;

$R^9$ and $R^{11}$ are independently H or $CH_3$;

$R^{10}$ and $R^{12}$ are independently H, $CH_3$ or $OCH_3$;

Q is $CH_2W$; and

W is phenyl optionally substituted with 1–3 substituents selected from halogen, $C_1$–$C_3$ alkyl, $C_1$–$C_3$ alkoxy, OH, CN, $C_1$–$C_3$ haloalkyl, $C_1$–$C_3$ haloalkoxy, $C_1$–$C_3$ alkylthio, $C_2$–$C_4$ alkenyl and $C_2$–$C_4$ alkynyl.

2. A compound of claim 1 wherein W is phenyl optionally substituted by 1–2 substituents selected from halogen, $CH_3$ and $OCH_3$.

3. A compound of claim 1 wherein:

$R^1$ is $C_1$–$C_6$ alkyl; $C_3$–$C_6$ cycloalkyl; phenyl optionally substituted with one to two halogens; and $CR^9R^{10}X$;

$R^2$, $R^3$, $R^4$ and $R^5$ are independently H; and $R^6$ is $C_1$–$C_3$ alkyl and $C_2$–$C_4$ alkenyl.

4. A compound of claim 1 wherein:

W is phenyl optionally substituted with 1–2 halogens.

5. A compound of claim 3 wherein:

$R^1$ is $C_3$–$C_5$ alkyl, $C_3$–$C_6$ cycloalkyl or phenyl optionally substituted with one to two halogens.

6. The compound of claim 1 which is:

3-(1,1-dimethylethyl)-6-[[(2-fluorophenyl)-methoxy]methyl]-5,6-dihydro-6-methyl-4H-1,2-oxazine.

7. The compound of claim 1 which is:

6-[[(2,6-difluorophenyl)methoxy]methyl]-3-(1,1-dimethylethyl)-5,6-dihydro-6-methyl-4H-1,2-oxazine.

8. The compound of claim 1 which is:

6-[[(2,6-difluorophenyl)methoxy]methyl]-3-(1,1-dimethylethyl)-6-ethyl-5,6-dihydro-4H-1,2-oxazine.

9. The compound of claim 1 which is:

6-[[(2,6-difluorophenyl)methoxy]methyl]-6-ethyl-5,6-dihydro-3-phenyl-4H-1,2-oxazine.

10. A Compound of claim 3 wherein $R^1$ is $C_3$–$C_5$ alkyl, $C_3$–$C_6$ cycloalkyl or phenyl optionally substituted with one to two halogens.

11. A method for controlling the growth of undesired vegetation which comprises applying to the locus to be protected an effective amount of a compound of claim 1.

12. A method for controlling the growth of undesired vegetation which comprises applying to the locus to be protected an effective amount of a compound of claim 1.

13. A method for controlling the growth of undesired vegetation which comprises applying to the locus to be protected an effective amount of a compound of claim 3.

14. A method for controlling the growth of undesired vegetation which comprises applying to the locus to be protected an effective amount of a compound of claim 4.

15. A method for controlling the growth of undesired vegetation which comprises applying to the locus to be protected an effective amount of a compound of claim 5.

16. A composition suitable for controlling the growth of undesired vegetation which comprises an effective amount of a compound of claim 1 and at least one of the following: surfactant, solid or liquid diluent.

17. A composition suitable for controlling the growth of undesired vegetation which comprises an effective amount of a compound of claim 1 and at least one of the following: surfactant, solid or liquid diluent.

18. A composition suitable for controlling the growth of undesired vegetation which comprises an effective amount of a compound of claim 3 and at least one of the following: surfactant, solid or liquid diluent.

19. A composition suitable for controlling the growth of undesired vegetation which comprises an effective amount of a compound of claim 4 and at least one of the following: surfactant, solid or liquid diluent.

20. A composition suitable for controlling the growth of undesired vegetation which comprises an effective amount of a compound of claim 5 and at least one of the following: surfactant, solid or liquid diluent.

\* \* \* \* \*